United States Patent
Wong et al.

(10) Patent No.: US 11,959,074 B2
(45) Date of Patent: Apr. 16, 2024

(54) SYSTEM AND METHOD FOR AUTOMATED REPEAT SEQUENCING

(71) Applicant: LIFE TECHNOLOGIES CORPORATION, Carlsbad, CA (US)

(72) Inventors: Chiu Tai Andrew Wong, Orange, CT (US); Kylan Szeto, East Lyme, CT (US); Shanti Shankar, Cheshire, CT (US); Mark Beauchemin, S. Glastonbury, CT (US)

(73) Assignee: Life Technologies Corporation

( * ) Notice: Subject to any disclaimer, the term of this patent is extended or adjusted under 35 U.S.C. 154(b) by 90 days.

(21) Appl. No.: 17/525,737

(22) Filed: Nov. 12, 2021

(65) Prior Publication Data

US 2022/0154176 A1 May 19, 2022

Related U.S. Application Data

(60) Provisional application No. 63/113,869, filed on Nov. 14, 2020.

(51) Int. Cl.
| | | |
|---|---|---|
| *C12N 15/10* | (2006.01) | |
| *C12Q 1/6825* | (2018.01) | |
| *C12Q 1/6874* | (2018.01) | |
| *G01N 35/10* | (2006.01) | |

(52) U.S. Cl.
CPC ....... *C12N 15/1065* (2013.01); *C12Q 1/6825* (2013.01); *C12Q 1/6874* (2013.01); *G01N 35/1081* (2013.01)

(58) Field of Classification Search
None
See application file for complete search history.

(56) References Cited

U.S. PATENT DOCUMENTS

| | | | |
|---|---|---|---|
| 9,139,665 B2 * | 9/2015 | Fonnum | C08F 230/085 |
| 10,273,540 B2 * | 4/2019 | Davey | G16B 30/00 |

FOREIGN PATENT DOCUMENTS

| | | | |
|---|---|---|---|
| WO | WO-03102212 A2 * | 12/2003 | ......... C12Q 1/6811 |
| WO | WO-2007120859 A2 | 10/2007 | |
| WO | WO-2011156707 A2 | 12/2011 | |
| WO | WO-2014144092 A1 | 9/2014 | |

OTHER PUBLICATIONS

PCT/US2021/059242, International Search Report and Written Opinion, dated Feb. 4, 2022, 10 pages.

* cited by examiner

*Primary Examiner* — Nancy J Leith
*Assistant Examiner* — Jessica D Parisi

(57) ABSTRACT

A method for sequencing a target polynucleotide includes detecting a first series of nucleotide incorporations complementary to at least a portion of the target polynucleotide. The first series of nucleotide incorporations forms a first complementary polynucleotide. The target nucleotide is secured to a substrate disposed in a sequencing zone of an assembly. The method further includes moving the substrate to which the target nucleotide is secured to a templating zone of the assembly; removing the first complementary polynucleotide when the substrate is disposed at the templating zone of the assembly, the target polynucleotide remaining secured to the substrate; following the removing, moving the substrate to which the target polynucleotide is secured to the sequencing zone; and detecting a second series of nucleotide incorporations complementary to at least a portion of the target polynucleotide, the second series of nucleotide incorporations forming a second complementary polynucleotide.

20 Claims, 35 Drawing Sheets

SYSTEM AND METHOD FOR AUTOMATED REPEAT SEQUENCING

CROSS-REFERENCE TO RELATED APPLICATION(S)

This application claims benefit of U.S. Provisional Application No. 63/113,869, filed Nov. 14, 2020, which is incorporated herein by reference in its entirety.

FIELD OF THE DISCLOSURE

This disclosure, in general, relates to systems and methods for sequencing target polynucleotides.

BACKGROUND

Increasingly, genetic sequencing is being used as a tool in both research and clinical settings. For example, research into the origins of disease, differentiations of species, characteristics of microbiomes, and the study of both bacterial and viral pathogens is being performed using genetic sequencing. In another example, genetic testing is increasingly being used to detect cancers, trace viral infections, prescribed diets, and modify prescription formularies. Such research and testing often relies on the detection of small deviations or variance in genetic samples. As such, accuracy is a factor in determining the applicability of a sequencing technique.

Furthermore, the availability of testing is often driven by factors that affect cost, such as the cost of equipment, reagents, and hands-on time by technicians. Conventional methods to increase accuracy also increased hands-on time by a technician and the use of costly reagents.

As such, accurate, low-cost solutions would be desirable.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an embodiment, the method includes detecting a series of nucleotide incorporations characteristic of a target polynucleotide. For example, a primer hybridized to a target polynucleotide can be extended and the series of nucleotide incorporations can be detected utilizing techniques associated with sequencing-by-synthesis. The target polynucleotide can be associated with a substrate disposed in a sequencing zone of an instrument. Following detection of the series of nucleotide incorporations, the substrate with which the target polynucleotide is associated can be moved to a templating zone within the instrument. For example, the substrate can be moved automatically using a mechanical subsystem to the templating zone from the sequencing zone. In the templating zone, the target polynucleotide hybridized to an extended primer can be denatured, resulting in the removal of the extended primer, leaving the single-stranded target polynucleotide associated with the substrate. In an example, the extended primer can be dehybridized by melt-off, for example, by increasing the temperature of the solution surrounding the hybridized target polynucleotide. In another example, the target polynucleotide and extended primer can be dehybridized utilizing a change in ionic strength. Following denaturing, a new primer can be hybridized to the polynucleotide and enzymes, such as a polymerase enzyme, can be associated with the primer/target polynucleotide hybrid. The substrate, including the target polynucleotide, can be automatically moved to the sequencing zone of the instrument. Optionally, the hybridization of the new primer or the association of the enzyme can occur in the templating zone or can occur after moving the substrate to the sequencing zone. In the sequencing zone, a second series of nucleotide incorporations can be detected, for example, as the primer is extended complementary to the target polynucleotide using sequencing-by-synthesis techniques.

Signals derived from the detection of nucleotide incorporations can be used to determine the order of nucleotides in the target polynucleotide. For example, a first set of signal can be derived from detection of the first series of nucleotide incorporations, and a second set of signals can be derived from detection of the second series of nucleotide incorporations. In an example, corresponding signals can be averaged before performing base calling. In a particular example, a weighted average can be used.

Figure 1:
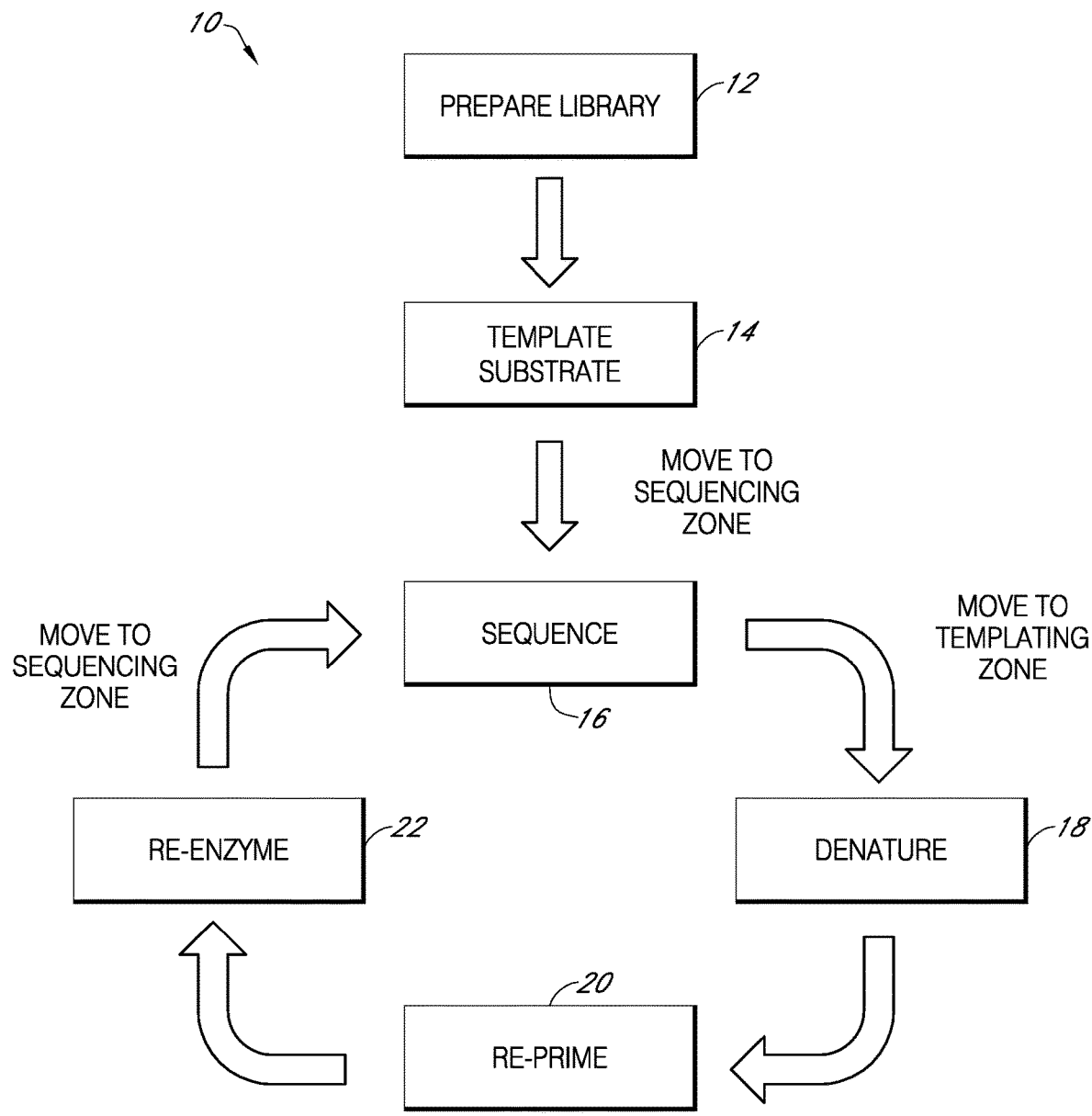
FIG. 1 includes a block flow diagram illustrating an example method for improved genetic sequencing.

FIG. 1 includes a block flow diagram illustrating an example method 10 for determining a genetic sequence of a target polynucleotide. The method 10 includes preparing a library, as illustrated at block 12. Libraries can be prepared from random fragmenting of DNA samples. In another example, targeted libraries can be prepared using, for example, ION Ampliseq™ or ION Ampliseq HD™. In general, the library includes a plurality of polynucleotides to be tested through genetic sequencing.

The polynucleotides can be applied to a substrate. In an example, polynucleotides can be directly attached to the substrate. In another example, the polynucleotide may be copied onto a bead or particle that is then applied to the substrate. In a further example, the substrate may include a polymer matrix to which polynucleotides are attached or copied. Such techniques are referred to herein as templating and result in a plurality of target polynucleotides attached, directly or indirectly, to the substrate. In an example, templating the substrate can occur in the templating zone of the instrument, as illustrated at block 14.

Depending on the nature of the sequencing technique, the substrate can be transparent. Alternatively, the substrate can include a semiconductor circuitry, such as an ion sensitive field-effect transistor for detecting changes in ion concentration or electrodes for detecting resistance or induction. Further, the substrate may include confinement regions, such as openings, holes, wells, or grooves. The confinement regions can be cooperatively coupled to sensors, such as ion-sensitive field-effect transistors.

A primer can be hybridized to the target polynucleotides. At least a portion of an oligonucleotide primer is fully or partially complementary to a primer binding region on the target polynucleotide. An oligonucleotide primer may comprise: a single-stranded or double-stranded polynucleotide; DNA, RNA, chimeric DNA/RNA, or nucleic acid analogs; polymers of deoxyribonucleotides, ribonucleotides, or analogs thereof; or a plurality of different polynucleotides comprising naturally-occurring, synthetic, recombinant, cloned, amplified, unamplified or archived (e.g., preserved) forms. In some embodiments, at least a portion of an oligonucleotide primer comprises a sequence having no sequence identity or complementarity to a region on the target polynucleotide (e.g., tailed primers).

In addition, an enzyme can be associated with the hybridized primer/polynucleotide. For example, a polymerase may include any enzyme, or fragment or subunit of thereof, that can catalyze the polymerization of nucleotides or nucleotide analogs. The polymerase may be a DNA polymerase, which may include bacterial DNA polymerases, eukaryotic DNA polymerases, archaeal DNA polymerases, viral DNA polymerases, and phage DNA polymerases; a DNA-dependent polymerase; a replicase; a primase; an RNA-dependent polymerase (including RNA-dependent DNA polymerases such as, for example, reverse transcriptases); a T3, T5, T7, or SP6 RNA polymerase; a thermo-labile polymerase, or a thermo-stable polymerase. The polymerase may be selected from low or high fidelity polymerases, which may include naturally occurring polymerases and any subunits and truncations thereof; mutant polymerases; variant polymerases; recombinant, fusion or otherwise engineered polymerases; chemically modified polymerases; and synthetic molecules or assemblies, and any analogs, derivatives or fragments thereof that retain the ability to catalyze nucleotide polymerization. Typically, a polymerase comprises one or more active sites at which nucleotide binding or catalysis of nucleotide polymerization can occur. In some embodiments, a polymerase includes or lacks other enzymatic activities, such as, e.g., 3' to 5' exonuclease activity or 5' to 3' exonuclease activity. In some embodiments, sequencing reactions may be conducted with a single type of polymerase or a mixture of polymerases or ligases. In some embodiments, the polymerase may be an *E. coli* large fragment DNA polymerase I (e.g., Klenow).

The templated substrate can be moved to a sequencing zone within the instrument, for example, automatically using a mechanical subsystem. Once in the sequencing zone, the target polynucleotides can be sequenced, indicated by block 16. For example, a series of nucleotide incorporations can be detected. In an example, a primer hybridized to the target polynucleotide can be extended using sequencing-by-synthesis techniques. During sequencing-by-synthesis, nucleotides may be sequentially added to growing polynucleotide molecules or strands at positions complementary to template polynucleotide molecules or strands. The addition of the nucleotides to the growing complementary strands, which may be detected using a variety of methods (e.g., pyrosequencing, fluorescence detection, and label-free electronic detection), may be used to identify the sequence composition of the target polynucleotide. This process may be iterated until a complete or selected sequence length complementary to the template has been synthesized.

In electronic or charged-based sequencing (such as, e.g., pH-based sequencing), a nucleotide incorporation event may be determined by detecting ions (e.g., hydrogen ions) generated as natural byproducts of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc.

The reagents may be delivered for predetermined durations, at predetermined flow rates, and may measure physical or chemical parameters providing information about the status of one or more reactions taking place in defined spaces or reaction confinement regions. The predetermined ordering may be based on a cyclical, repeating pattern consisting of consecutive repeats of a short pre-determined reagent flow ordering (e.g., consecutive repeats of pre-determined sequence of four nucleotide reagents such as, for example, "ACTG . . . "), may be based in whole or in part on some other pattern of reagent flows (such as, e.g., any of the various reagent flow orderings discussed in Hubble et al., U.S. Pat. No. 10,329,608 or in Hubbell et al., U.S. Pat. Appl. Publ. No. 2012/0264621, published Oct. 18, 2012, which are incorporated by reference herein in their entirety), and may also be based on some combination thereof.

Upon completion of the detection of the series of nucleotide additions, the substrate can be moved to the templating zone using the mechanical subsystem. As illustrated at block 18, extended primers hybridized to the target polynucleotide can be dehybridized or denatured utilizing, for example, an increase in temperature or a change in ionic strength. For example, when the substrate is in the templating zone, the temperature of the solution associated with or surrounding the hybridized polynucleotide and extended primer can be heated to dehybridized the extended primer from the target polynucleotide and the extended primer can be washed from the system. In another example, an ionic strength in the solution surrounding the target polynucleotide can be changed, resulting in the dehybridization of the extended primer, which can then be washed from the system.

In some embodiments, denaturing or dehybridizing includes removing an extension product using physical, chemical, or enzymatic reactions. For example, a primer extension product may be denatured/melted from a target polynucleotide using an elevated temperature (e.g., about 75-100° C. without formamide or about 45-90° C. with formamide) or a chemical denaturant (e.g., a compound known to dissociate double-stranded nucleic acid molecules, such as formamide, urea, DMSO, alkali conditions, low salt or very-low salt conditions, or water). A primer extension product may also be degraded using a nuclease enzyme. In some embodiments, an extension product may be degraded using a nucleic acid degrading enzyme, such as a 5'→3' or 3'→5' exonuclease (e.g., exonuclease I, exonuclease III, or T7 gene 6 exonuclease).

As illustrated at block 20, new primer can be hybridized to the target polynucleotide or complement thereof. The primer can be the same as the primer hybridized to the target polynucleotide during the first sequencing run. Alternatively, a different primer can be used.

As illustrated at block 22, a new enzyme can be associated with the target polynucleotide hybridized to the new primer. For example, a polymerase can be added that associates with the primer/target polynucleotide. The enzyme can be the same species of enzyme as utilized during the prior sequencing. Alternatively, a new species enzyme can be associated with the target/primer hybrid.

The substrate can be moved automatically to the sequencing zone from the templating zone utilizing a mechanical subsystem, and the target polynucleotide can again be sequenced by detecting a subsequent series of nucleotide incorporations. Alternatively, the substrate can be moved to the sequencing zone prior to the addition of the new primer and enzyme. When in the sequencing zone, the subsequent series of nucleotide incorporations can be detected by extending the primer complementary to the target polynucleotide, for example, using sequencing-by-synthesis techniques. Reagents can be provided in the same flow order as the first sequencing run. In another example, a different flow order can be used. The flow order can be selected from those described above.

Upon detecting the first and second series of nucleotide incorporations, data from the detected series can be utilized to determine the sequence of the target polynucleotide. For example, detecting the first and second series of nucleotide incorporations can provide first and second sets of signals that can be used for base calling. See, for example, U.S. Pat. No. 10,329,608B2, incorporated herein by references.

In an embodiment, a sequencing system includes an automated sequencing instrument adapted to determine sequences of polynucleotides and variant calls from a set of sample polynucleotides. The system can utilize a targeted assay to generate a library of amplicons or target polynucleotides that are sequenced to provide an aligned sequence listing and optionally, variant calls within a desirable time.

Embodiments of the automated sequencing instruments include a preparation deck for preparing libraries of targeted polynucleotides. In an example, the targeted polynucleotides are seeded onto a substrate, such as a polymeric or hydrogel bead. The automated sequencing instrument can further include a loading device to apply the seeded substrate onto a sensor device and can include a sequencer, for example, to perform sequencing-by-synthesis reactions by detecting nucleotide incorporations. The automated sequencing instrument can further include computational devices to utilize the data from the sequencer to determine base calls, aligned reads, and variant calls. In addition, the system can include user interfaces or network interfaces to communicate reports associated with the base calls, aligned reads, or variant calls to a user.

While the above description includes detecting first and second series of nucleotide incorporations, the cyclical method can be performed more than once, providing several series of nucleotide incorporations and associated sets of signals that can be used to perform base calling.

Definitions

As used herein, the term "nucleic acid" and its variants, which is used interchangeably herein with the term "polynucleotide," refers to a polymer of nucleotides and includes, for example, deoxyribonucleic acid and ribonucleic acid. Nucleic acids include, but are not limited to, DNA, cDNA, RNA, chimeric RNA/DNA, and nucleic acid analogs.

As used herein, a primer is any single-stranded nucleic acid molecule (e.g., an oligonucleotide) that, once hybridized to a complementary nucleic acid sequence, can prime, or initiate, nucleic acid synthesis. Typically, such nucleic acid synthesis occurs in a template-dependent fashion, and nucleotides are polymerized onto at least one end of the primer during such nucleic acid synthesis. Primers typically have a free 3' hydroxyl, however in some embodiments, a primer end is blocked (e.g., to prevent extension from the 3' end) or the primer is a fusion primer in which different portions of the primer are designed to bind to different partners. In a reaction that involves primer extension (e.g., pre-seeding amplification), a blocking moiety at the 3' end of a blocked fusion primer can reduce the level of primer-dimer formation. In some embodiments, blocked or unblocked primers are tailed primers wherein the 5' end includes a sequence that is non-complementary to a target nucleic acid to which the rest of the primer is complementary. This 5' tail can be used as a template for primer extension. In various embodiments of methods provided herein, nucleic acid molecules include a first primer binding sequence and optionally a second primer binding sequence. In some embodiments, reactions described herein include a population of first primers and optionally a population of second primers that bind the forward primer binding and reverse primer binding sequences, respectively, or vice versa. In some embodiments, the first and second primers are referred to as a primer pair. In some embodiments, the first primers or the second primers are universal primers. The first primer can bind to either the forward primer binding sequence or the reverse primer binding sequence and the second primer can bind to either the forward primer binding sequence or the reverse primer binding sequence. Accordingly, the terms "first" and "second" when used herein with reference to a primer are relative terms, and each can refer to a forward or reverse primer depending on the context in which they are used.

As used herein, nucleic acid amplification refers to a process in which a new strand of a nucleic acid is synthesized through nucleotide polymerization and involves one or more cycles of the following: separation, e.g., denaturation or dissociation, of double-stranded nucleic acids into single strands, annealing, e.g., hybridization, of a primer to single strands of the separated double-stranded nucleic acids and extension of the hybridized primers. The term "primer extension" and its variants, as used herein, relates to any method for catalyzing nucleotide incorporation onto a terminal end of a nucleic acid molecule. In some embodiments, a cycle of amplification includes (a) partial, incomplete, or complete denaturation or dissociation of the strands of a double-stranded nucleic acid, (b) hybridization or annealing of a primer to a partially or completely single-stranded nucleic acid, and (c) primer extension to form an extended primer strand. In some embodiments, a cycle of amplification optionally includes (a) hybridization of a first primer to a template nucleic acid strand, (b) primer extension to form a first extended nucleic acid strand, and (c) partial or incomplete denaturation of the extended strand from the template strand. Optionally, the denatured portion of the template strand from step (c) is free to hybridize with a different primer in the next amplification cycle. In some embodiments, primer extension in an amplification cycle involves displacement of one strand of a duplex nucleic from the other strand of the duplex or displacement of the first extended strand from the template strand. A second primer can be included which hybridizes to the 3' end of the first extended strand.

Numerous methods of nucleic acid amplification are known in the art. Some examples include recombinase-polymerase amplification (RPA), template walking and polymerase chain reaction (PCR) amplification. In an RPA reaction, nucleic acid molecules are amplified using a recombinase, polymerase, and optionally a recombinase accessory protein in the presence of primers and nucleotides. The recombinase and optionally the recombinase accessory protein can dissociate at least a portion of a double-stranded template nucleic acid molecules to allow primers to hybridize that the polymerase can then bind to initiate replication. An example of a recombinase accessory protein is a single-stranded binding protein (SSB) that prevents the re-hybridization of dissociated nucleic acid molecules. Typically, RPA reactions are isothermal and performed at isothermal temperatures. In some instances, an RPA reaction can be performed within an emulsion. In a template walking reaction, template nucleic acid molecules are amplified using a polymerase in the presence of primers and nucleotides in reaction conditions that allow at least a portion of double-stranded template nucleic acid molecules to dissociate such that primers can hybridize and the polymerase can then bind to initiate replication. In PCR, the double-stranded template nucleic acid molecules are typically dissociated by thermal cycling. After cooling, primers bind to complementary sequences and can be used for replication by the polymerase. In some of the embodiments of methods provided herein, a pre-seeding or templating reaction is performed in a reaction mixture formed with the components necessary for amplification of the template nucleic acid molecules. In any of the disclosed aspects, the reaction mixture includes some or all of the following: a population of template nucleic acid molecules, a polymerase, one or more supports or surfaces (e.g., solid supports) with a population of attached first primers, nucleotides, or a cofactor such as a divalent cation. In some embodiments, the reaction mixture further includes a second primer and optionally a diffusion-limiting agent. In some embodiments, the population of template nucleic acid molecules comprise template nucleic acid molecules joined to at least one adaptor sequence which hybridizes to the first or second primers. In some embodiments, the reaction mixture forms an emulsion, as in emulsion RPA or emulsion PCR. In reactions involving RPA, the reaction mixture includes a recombinase and optionally a recombinase accessory protein. The various components of the reaction mixture are discussed in further detail herein.

As used herein, the terms "identity" and "identical" and their variants, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window or designated region. Sequences are said to be "substantially identical" when there is at least about 80%, or at least about 85%, identity at the amino acid level or at the nucleotide level. In some instances, sequences are "substantially identical" when there is at least 90% identity, at least 91% identity, at least 92% identity, at least 93% identity, at least 94% identity, at least 95% identity, at least 96% identity, at least 97% identity, at least 98% identity, at least 99% identity at the amino acid level or at the nucleotide level. Preferably, the identity exists over a region that is at least about 20, 25, 50, or 100 residues in length, or across the entire length of at least one compared sequence. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences or primers) that can undergo cumulative base pairing at two or more individual corresponding positions in antiparallel orientation, as in a hybridized duplex. Such base pairing can proceed according to any set of established rules, for example according to Watson-Crick base pairing rules. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the sequences where two opposed nucleotides are not complementary. Complementary nucleotides include nucleotides that are efficiently incorporated by DNA polymerases opposite each other during DNA replication under physiological conditions.

As used herein, the term "monoclonal" and its variants, when used in reference to one or more polynucleotide populations, refers to a population of polynucleotides where at about 50-99%, or up to 100%, or 100% of the members of the population share at least 80% identity, or at least 85% identity, or at least 90% identity, or at least 95% identity, or at least 99% identity, or about 100% identity, or 100% identity at the nucleotide sequence level. As used herein, the phrase "substantially monoclonal" and its variants, when used in reference to one or more polynucleotide populations, refer to one or more polynucleotide populations wherein one polynucleotide molecule, e.g., an amplified template polynucleotide molecule, is the single most prevalent polynucleotide in the population. Accordingly, all members of a monoclonal or substantially monoclonal population need not be completely identical or complementary to each other. For example, different portions of a polynucleotide template can become amplified or replicated to produce the members of the resulting monoclonal population; similarly, a certain number of "errors" or incomplete extensions may occur during amplification of the original template, thereby generating a monoclonal or substantially monoclonal population whose individual members can exhibit sequence variability amongst themselves. In some embodiments, a low or insubstantial level of mixing of non-homologous polynucleotides may occur during nucleic acid amplification reactions, and thus a substantially monoclonal population may contain a minority of one or more polynucleotides (e.g., less than 50%, less than 40%, less than 30%, less than 20%, less than 10%, less than 5%, less than 1%, less than 0.5%, less than 0.1%, or less than 0.001%, of diverse polynucleotides). In certain examples, at least 90% of the polynucleotides in the population are at least 90% identical to the original single template used as a basis for amplification to produce the substantially monoclonal population. In certain embodiments, amplifying of a template polynucleotide yields a population of polynucleotides wherein at least 50%, 60%, 70%, 75%, 80%, 85%, 90%, 91%, 92%, 93%, 94%, 95%, 96%, 97%, 98%, 99%, or 100% of the members of a population of polynucleotides share at least 50%, 60%, 70%, 75%, 80%, 85%, 90%, 95%, 96%, 97%, 98%, 99%, or 100% sequence identity to the template nucleic acid from which the population was generated. In certain embodiments, amplifying of a template polynucleotide yields a population of polynucleotides in which a large enough fraction of the polynucleotides share enough sequence identity to allow sequencing of at least a portion of the amplified template using a high-throughput sequencing system.

In some embodiments, at least 50%, 60%, 70%, 75%, 80%, 90%, 95%, or 99%, of the members of the nucleic acid molecules attached to a templated support will share greater than 90%, 95%, 97%, 99%, or 100% identity with the template nucleic acid molecule. In some embodiments, members of a nucleic acid population which are produced using any of the amplification methods, hybridize to each other under high-stringency hybridization conditions.

In some embodiments, amplification methods provided herein, including, for example, amplification processes used in templating nucleic acids, as well as apparatuses, devices, systems, compositions and kits involving the methods, generate a substantially monoclonal population of nucleic acid molecules that includes sufficiently few polyclonal contaminants such that they can be successfully sequenced in a high-throughput sequencing method. For example, the amplification methods can generate a substantially monoclonal population of nucleic acid molecules that provides for the production of a signal (e.g., a sequencing signal, a nucleotide incorporation signal, and the like) that is detected using a particular sequencing system. Such signals include any detectable signal indicative of nucleotide polymerization, including, but are not limited to, optical or optically detectable signals, non-optical signals (or signals detectable by non-optical detection techniques), ion (e.g., hydrogen ion) concentration, pH, electrical signals, voltage, and changes of fluctuations in any such signal. Optionally, the signal can subsequently be analyzed to correctly determine the sequence or base identity of any one or more nucleotides present within any nucleic acid molecule of the population. Examples of suitable sequencing systems for detection or analysis of such signals include, but are not limited to, systems that include ionic sensors, e.g., a field effect transistor (FET), for example a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, is used for measuring ion concentrations in solution; when the ion concentration (such as $H^+$) changes, the current through the transistor changes accordingly. Non-limiting examples of systems that include FLT sensors are the Ion Torrent sequencing systems, such as the Ion Torrent PGM™ sequence systems, including the 314, 316 and 318 systems, the Ion Torrent Proton™ sequencing systems, including Proton I, (Thermo Fisher Scientific, Waltham, MA), the Ion Torrent S5™ sequencing systems, including Ion S5 and S5XL (Thermo Fisher Scientific, Waltham, MA), and the Ion Torrent Genexus™ sequencing systems (Thermo Fisher Scientific, Waltham, MA). In one embodiment, an ISFET-based sequencing system for detection or analysis of signals is described in detail herein. In some embodiments, a substantially monoclonal nucleic acid population permits the accurate sequencing of at least 5 contiguous nucleotide residues on a system incorporating FET sensors, e.g., an Ion Torrent sequencing system.

As used herein, the term "clonal amplification" and its variants refer to any process whereby a monoclonal, or substantially monoclonal, polynucleotide population is produced via amplification of a polynucleotide. In some embodiments of clonal amplification, two or more polynucleotides are amplified to produce at least two a monoclonal, or substantially monoclonal, polynucleotide populations.

As used herein, the term "pre-seeding," also referred to herein as "seeding," refers to a process involving the attachment of a polynucleotide to a surface or support. In some embodiments, pre-seeding involves attachment of one or more nucleic acids to a surface or support, or to one or more sites on a surface or support. Pre-seeded surfaces or supports are used, for example, in further manipulation or analysis, e.g., nucleic acid amplification (including, e.g., amplification in a templating process), sequencing or other processes, of the attached nucleic acids. In some embodiments, the pre-seeding process generates one or more surfaces or supports having one or more nucleic acid molecules attached thereto. In some embodiments, pre-seeding generates one or more surfaces or supports having a single polynucleotide attached thereto. The one or more surfaces or supports having one or more nucleic acid molecules attached thereto may be included in a population, plurality or collection of two or more surfaces or supports, in which some, a minority, a majority, or substantially all of the surfaces or supports have one or more nucleic acid molecules attached thereto. In some embodiments, the nucleic acid molecule or molecules attached to different surfaces or supports, or to different sites on a surface or support, are different. In some embodiments, multiple (or a plurality of) substantially identical copies of a nucleic acid molecule (or substantially monoclonal nucleic acids) are attached to a surface or support or multiple (or a plurality of) different nucleic acids are attached to one or more sites on a surface or support(s) in a pre-seeding process. In some embodiments, a limited number of substantially identical copies of a polynucleotide (or substantially monoclonal nucleic acids) is attached to a surface or support to generate a monoclonal, or substantially monoclonal, population of nucleic acids in a pre-seeding process. In some embodiments, pre-seeding of a surface or support includes attachment of a nucleic acid to a surface or support, for example, by hybridization of the nucleic acid to a complementary polynucleotide attached to the support, in a process that does not involve nucleic acid amplification. In some embodiments, pre-seeding of a surface or support includes nucleic acid amplification, e.g., one or more cycles of nucleic acid amplification (e.g., PCR) or isothermal amplification. For example, nucleic acid amplification may be used in a pre-seeding process to generate one or more copies of a nucleic acid that is capable of attaching (e.g., by hybridization) to a surface or support. Typically, pre-seeding that generates a surface or support having more than one nucleic acid, or multiple copies of a nucleic acid, attached thereto includes nucleic acid amplification. A surface or support generated in a pre-seeding or seeding process as provided herein is referred to as a "pre-seeded" or "seeded" support.

As used herein, a "limited number" when referring to a number of nucleic acids (or substantially identical copies of, or substantially monoclonal, nucleic acids) attached to a surface or support in a pre-seeding or templating method typically refers to a number of nucleic acids that is controlled for various purposes. A limited number of copies of a nucleic acid can be, for example, a number sufficient to provide a crowding effect in any subsequent larger scale amplification (e.g., templating) of the nucleic acids on the surface or support to generate a larger substantially monoclonal population of the nucleic acids in order to prevent or reduce polyclonal population formation by preventing or reducing migration of the templates between reaction sites. Such a limited number of template copies can be limited in order to use relatively short nucleic acid amplification times, for example, to prevent or reduce migration of templates between reaction sites but generate a sufficient number of template copies to provide a crowding effect in subsequent amplifications.

As used herein, the term "templating" refers to a process of generating two or more, or a plurality or population, of substantially identical polynucleotides, or of generating a substantially monoclonal population of nucleic acids, that can be used as templates in nucleic acid analysis methods, including, for example, nucleic acid sequencing, such as sequencing by synthesis, of the polynucleotides. The polynucleotides generated in a templating process are typically referred to as nucleic acid templates. In some embodiments, templating involves attachment of polynucleotide templates to a surface or support. In some embodiments, templating involves generating two or more, or a plurality, of separate surfaces or supports, or discrete sites on a surface or support, each having attached thereto two or more, or a plurality or population, of substantially identical polynucleotides, or a substantially monoclonal population of polynucleotides. In some embodiments, templating involves generating one or more surfaces or supports, or discrete sites on a surface or support, having a substantially monoclonal population of polynucleotides attached thereto. In some embodiments, templating generates one or more surfaces or supports having a substantially monoclonal population of at least 50,000, 75,000, 100,000, 125,000, 150,000, 200,000, 250,000, 300,000, 350,000, 400,000, 450,000, 500,000, 600,000, 700,000, 800,000, 900,000 or $10^6$ or more template nucleic acid molecules attached to each templated surface or support. In some embodiments, templating generates surfaces or supports having a substantially monoclonal population of between about 50,000 and 500,000 template nucleic acid molecules attached to each templated surface or support, or, for example, between about 50,000 and 400,000 template nucleic acid molecules, between about 50,000 and 300,000 template nucleic acid molecules, between about 50,000 and 200,000 template nucleic acid molecules, or between about 50,000 and 100,000 template nucleic acid molecules attached to each templated support. In some embodiments, templating generates one or more templated surfaces or supports having a substantially monoclonal population of between about 100,000 and 400,000 template nucleic acid molecules attached to each templated surface or support, between about 100,000 and 300,000 template nucleic acid molecules, between about 100,000 and 200,000 template nucleic acid molecules, or between about 150,000 and 300,000 template nucleic acid molecules attached to each templated support. In some embodiments, templating is performed starting with one or more pre-seeded or seeded surfaces or supports. In such embodiments, templating can generate one or more templated surfaces or supports including at least 1.5 times, at least 2 times, at least 2.5 times, at least 3 times, at least 3.5 times, at least 4 times, at least 4.5 times, at least 5 times, at least 5.5 times, at least 6 times, at least 6.5 times, at least 7 times, at least 7.5 times, at least 8 times, at least 8.5 times, at least 9 times, at least 9.5 times, at least 10 times, at least 25 times, at least 50 times, at least 100 times, at least 250 times, at least 500 times, at least 1000 times, at least 2500 times, at least 5000 times, at least 10,000 times, at least 25,000 times, at least 50,000 times, at least 100,000 times, at least 250,000 times, at least 5000,000 times, or at least $10^6$ times or more as many template nucleic acid molecules on the templated surfaces or supports as were present on the pre-seeded surfaces or supports. In some embodiments, only about 1 or only 1 nucleic acid molecule is present on a pre-seeded support. In some embodiments, at least 50,000, 75,000 or 100,000 substantially monoclonal template nucleic acid molecules or between about 25,000 and 1,000,000 substantially monoclonal template nucleic acid molecules are present on a surface or support, for example between about 25,000 and 500,000, between about 25,000 and 250,000, between about 25,000 and 125,000, or between about 25,000 and 100,000 substantially monoclonal template nucleic acid molecules are present on a surface or support, e.g., a solid surface or support.

In some embodiments, the methods, as well as apparatuses, devices, systems, compositions and kits for performing the methods, provided herein, include supports, e.g., solid supports or semi-solid supports, to confine, enrich, sequester, isolate, localize, amplify or transfer nucleic acids that can be used in analysis methods. A solid surface or support may include a polymeric, a glass, or a metallic material. Examples of solid supports include a membrane, a planar surface, a microtiter plate, a bead, a filter, a test strip, a slide, a cover slip, and a test tube. A solid surface or support means any solid phase material upon which an oligomer is synthesized, attached, ligated, or otherwise immobilized. A support can optionally include a "resin", "phase", "surface", and "support". A support may be composed of, for example, organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of, for example, beads, spheres, particles, granules, a gel, or a surface. Surfaces may be, for example, planar, substantially planar, or non-planar, as well as concave, convex, or any combination thereof. Supports may be porous, semi-porous or non-porous, and may have swelling or non-swelling characteristics. A support can be shaped to include one or more wells, depressions or other containers, vessels, features, or locations. One or more supports may be configured in an array at various locations. A support is optionally addressable (e.g., for robotic delivery of reagents), or by detection means including scanning by laser illumination and confocal or deflective light gathering. A support (e.g., a bead) can be placed within or on another support (e.g., within a well of a second support). Examples of bead materials include, but are not limited to, gels, hydrogels, or acrylamide polymers. In some embodiments, a support is an Ion Sphere Particle (Thermo Fisher Scientific, Waltham, MA). Examples of solid supports include, but are not limited to, a "microparticle," "bead," "microbead" (optionally but not necessarily spherical in shape) sphere, filter, flow cell, well, groove, channel reservoir, gel, or inner wall of a capillary. In some embodiments, a surface includes texture (e.g., etched, cavitated, pores, three-dimensional scaffolds, or bumps). Sizes of supports include, but are not limited to, supports having a smallest cross-sectional length (e.g., diameter) of 50 microns or less, 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Also included in surfaces or solid supports are magnetic or paramagnetic beads (e.g., magnetic or paramagnetic nanoparticles or microparticles). For example, paramagnetic microparticles include paramagnetic beads attached with streptavidin (e.g., Dynabeads™ M-270 from Invitrogen, Carlsbad, CA). Particles can have an iron core, or can be a hydrogel or agarose (e.g., Sepharose™) Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymethylmethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). A bead surface can be functionalized for attaching one, or more, or a plurality, or a population of primers. In some embodiments, a bead is any size that can fit into a reaction chamber. For example, one bead can fit in a reaction chamber. In some embodiments, more than one bead fit in a reaction chamber. In some embodiments, the methods, as well as apparatuses, devices, systems, compositions, and kits for performing the methods, provided herein, include supports or surfaces having one, two or more, a plurality or a population of oligonucleotides (e.g., primers) attached thereto. A support or surface can be coated with an acrylamide, carboxylic, or amine compound for attaching a nucleic acid molecule (e.g., a first primer or second primer). For example, an amino-modified nucleic acid molecule (e.g., primer) can be attached to a support that is coated with a carboxylic acid. A primer can be attached to an acrylamide compound coating on a surface. Particles can be coated with an avidin-like compound (e.g., streptavidin) for binding biotinylated nucleic acids. In some embodiments, the oligonucleotides attached to a support or surface are substantially identical or include a primer sequence that is substantially identical in all the oligonucleotides. In some embodiments, two or more different oligonucleotides are attached to a support or surface. In some embodiments, a surface has attached a population of first primers, the first primers of the population sharing a common first primer sequence. In some embodiments, a surface has attached a population of first primers and a population of second primers, the first primers of the population sharing a common first primer sequence and the second primers of the population of second primers sharing a common second primer sequence. In some embodiments, the surface has immobilized thereon a population of first primers. In other embodiments, the surface has immobilized thereon a population of first primers and a population of second primers.

Overview

The method of FIG. 1 can be performed using various sequencing technologies. For example, the method can be performed using optical or fluorescent technologies or electronic-based technologies. In particular, the method can be performed using electronic-based technologies, such as using transistors to detect changed in ionic strength or pH or using electrodes an associated circuitry to detect changes in impedance or inductance.

Figure 2:
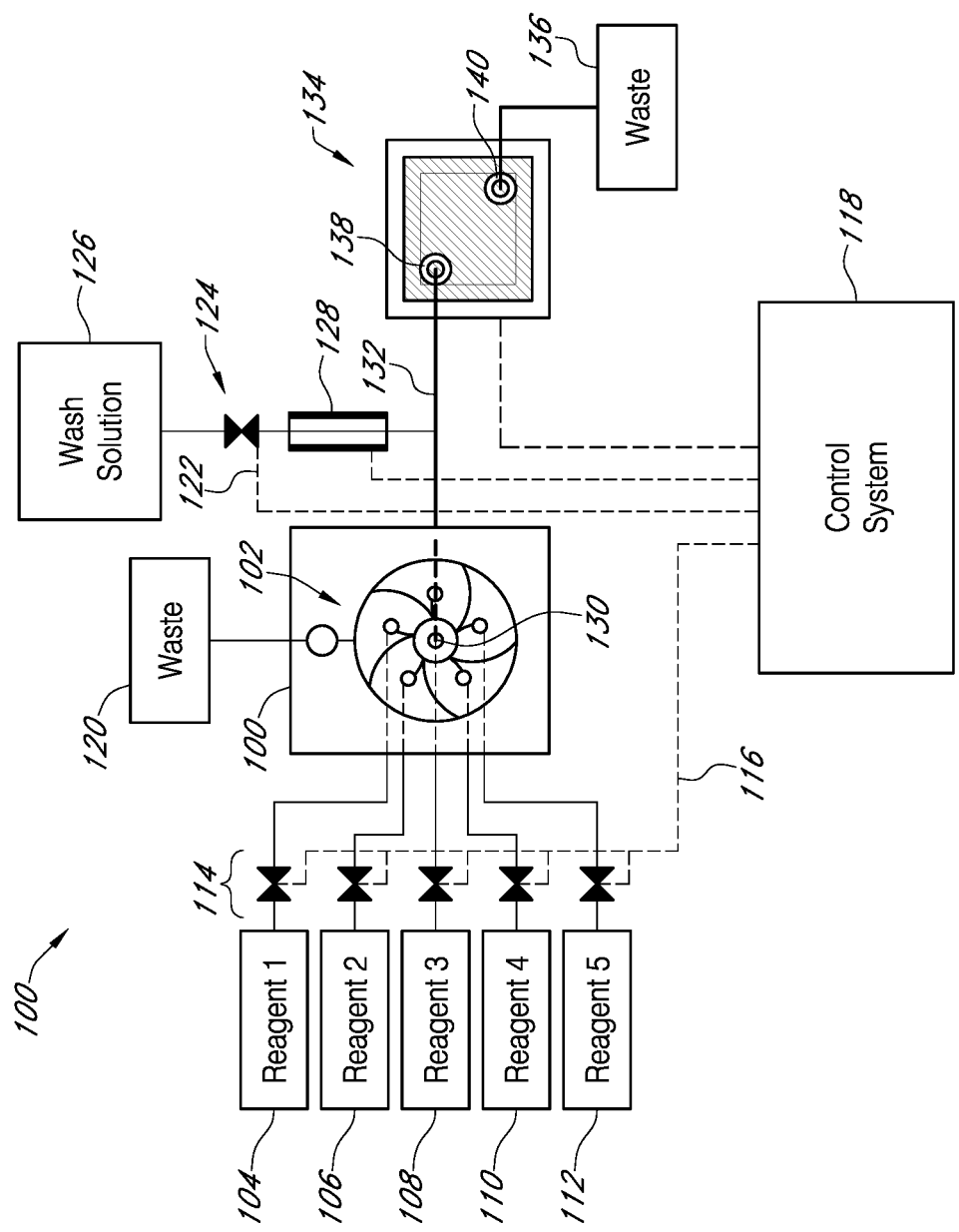
FIG. 2 includes an illustration of an example sequencing system.

In FIG. 2, a system 100 containing fluidics circuit 102 is connected by inlets to at least two reagent reservoirs (104, 106, 108, 110, or 112), to waste reservoir 120, and to biosensor 134 by fluid pathway 132 that connects fluidics node 130 to inlet 138 of biosensor 134 for fluidic communication. Reagents from reservoirs (104, 106, 108, 110, or 112) can be driven to fluidic circuit 102 by a variety of methods including pressure, pumps, such as syringe pumps, gravity feed, and the like, and are selected by control of valves 114. Reagents from the fluidics circuit 102 can be driven through the valves 114 receiving signals from control system 118 to waste container 120. Reagents from the fluidics circuit 102 can also be driven through the biosensor 134 to the waste container 136. The control system 118 includes controllers for valves 114, which generate signals for opening and closing via electrical connection 116.

The control system 118 also includes controllers for other components of the system, such as wash solution valve 124 connected thereto by electrical connection 122, and reference electrode 128. Control system 118 can also include control and data acquisition functions for biosensor 134. In one mode of operation, fluidic circuit 102 delivers a sequence of selected reagents 1, 2, 3, 4, or 5 to biosensor 134 under programmed control of control system 118, such that in between selected reagent flows, fluidics circuit 102 is primed and washed, and biosensor 134 is washed. Fluids entering biosensor 134 exit through outlet 140 and are deposited in waste container 136 via control of pinch valve regulator. The valve is in fluidic communication with the sensor fluid output 140 of the biosensor 134.

Figure 3:
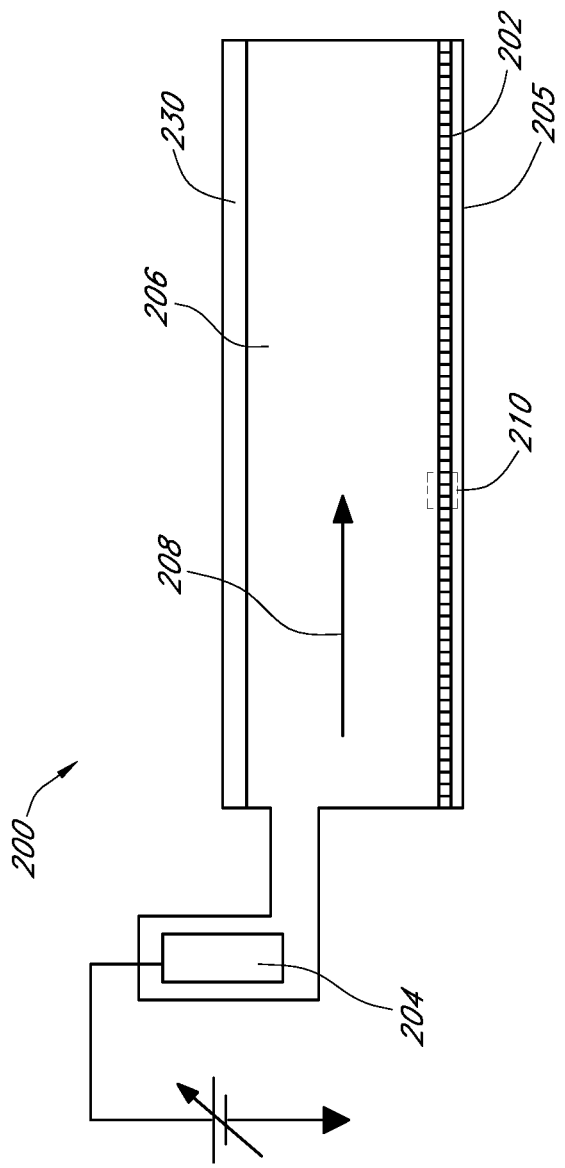
FIG. 3 includes an illustration of an example system including a sensor array.

In an embodiment, the biosensor can include a dielectric layer defining the well formed from the first access and second access and exposing a sensor pad. Such a biosensors finds particular use in detecting chemical reactions and byproducts, such as detecting the release of hydrogen ions in response to nucleotide incorporation, useful in genetic sequencing, among other applications. In a particular embodiment, a sequencing system includes a flow cell in which a sensory array is disposed, includes communication circuitry in electronic communication with the sensory array, and includes containers and fluid controls in fluidic communication with the flow cell. In an example, FIG. 3 illustrates an expanded and cross-sectional view of a flow cell 200 and illustrates a portion of a flow chamber 206. A reagent flow 208 flows across a surface of a well array 202, in which the reagent flow 208 flows over the open ends of wells of the well array 202. The well array 202 and a sensor array 205 together may form an integrated unit forming a lower wall (or floor) of flow cell 200. A reference electrode 204 may be fluidly coupled to flow chamber 206. Further, a flow cell cover 230 encapsulates flow chamber 206 to contain reagent flow 208 within a confined region.

Figure 4:
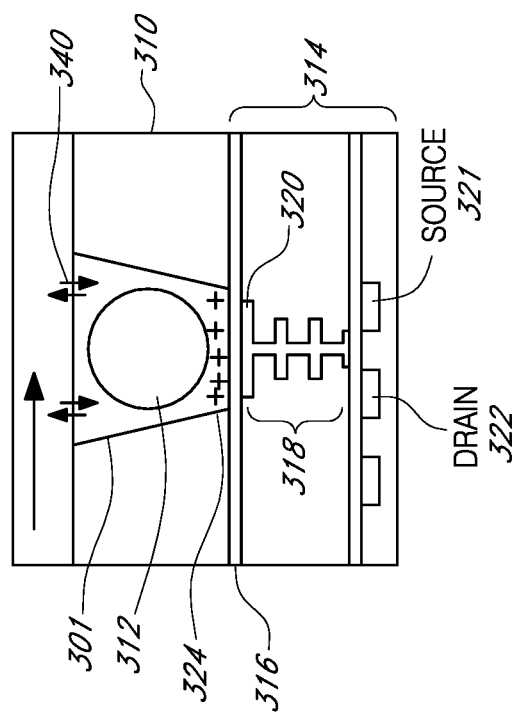
FIG. 4 includes an illustration of an example sensor and associated well.

FIG. 4 illustrates an expanded view of a well 301 and a sensor 314, as illustrated at 210 of FIG. 3. The volume, shape, aspect ratio (such as base width-to-well depth ratio), and other dimensional characteristics of the wells may be selected based on the nature of the reaction taking place, as well as the reagents, byproducts, or labeling techniques (if any) that are employed. The sensor 314 can be a chemical field-effect transistor (chemFET), more specifically an ion-sensitive FET (ISFET), with a floating gate 318 having a sensor plate 320 optionally separated from the well interior by a material layer 316. The sensor 314 can be responsive to (and generate an output signal related to) the amount of a charge 324 present on the material layer 316 opposite the sensor plate 320. The material layer 316 can be a ceramic layer, such as an oxide of zirconium, hafnium, tantalum, aluminum, or titanium, among others, or a nitride of titanium. Alternatively, the material layer 316 can be formed of a metal, such as titanium, tungsten, gold, silver, platinum, aluminum, copper, or a combination thereof. In an example, the material layer 316 can have a thickness in a range of 5 nm to 100 nm, such as a range of 10 nm to 70 nm, a range of 15 nm to 65 nm, or even a range of 20 nm to 50 nm.

While the material layer 316 is illustrated as extending beyond the bounds of the illustrated FET component, the material layer 316 can extend along the bottom of the well 301 and optionally along the walls of the well 301. The sensor 314 can be responsive to (and generate an output signal related to) the amount of a charge 324 present on the material layer 316 opposite the sensor plate 320. Changes in the charge 324 can cause changes in a current between a source 321 and a drain 322 of the chemFET. In turn, the chemFET can be used directly to provide a current-based output signal or indirectly with additional circuitry to provide a voltage-based output signal. Reactants, wash solutions, and other reagents may move in and out of the wells by a diffusion mechanism 340.

The well 301 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 301 of array 202 can have a characteristic diameter, defined as the square root of 4 times the cross-sectional area (A) divided by Pi (e.g., sqrt($4*A/\pi$)), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 301 can have a characteristic diameter of at least 0.01 micrometers. In a further example, the well 301 can define a volume in a range of 0.05 fL to 10 pL, such as a volume in a range of 0.05 fL to 1 pL, a range of 0.05 fL to 100 fL, a range of 0.05 fL to 10 fL, or even a range of 0.1 fL to 5 fL.

In an embodiment, reactions carried out in the well 301 can be analytical reactions to identify or determine characteristics or properties of an analyte of interest. Such reactions can generate directly or indirectly byproducts that affect the amount of charge adjacent to the sensor plate 320. If such byproducts are produced in small amounts or rapidly decay or react with other constituents, then multiple copies of the same analyte may be analyzed in the well 301 at the same time in order to increase the output signal generated. In an embodiment, multiple copies of an analyte may be attached to a solid phase support 312, either before or after deposition into the well 301. The solid phase support 312 may be microparticles, nanoparticles, beads, solid or porous comprising gels, or the like. For simplicity and ease of explanation, solid phase support 312 is also referred herein as a particle or bead. For a nucleic acid analyte, multiple, connected copies may be made by rolling circle amplification (RCA), exponential RCA, or like techniques, to produce an amplicon without the need of a solid support.

In particular, the solid phase support, such a bead support, can include copies of polynucleotides. In a particular example illustrated in FIG. 5, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

A bead support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Supports may be porous or non-porous, and may have swelling or non-swelling characteristics. In some embodiments, a support is an Ion Sphere Particle. Example bead supports are disclosed in U.S. Pat. No. 9,243,085, titled "Hydrophilic Polymeric Particles and Methods for Making and Using Same," and in U.S. Pat. No. 9,868,826, titled "Polymer Substrates Formed from Carboxy Functional Acrylamide," each of which is incorporated herein by reference.

In some embodiments, the solid support is a "microparticle," "bead," "microbead," etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). In an example, the support is at least 0.1 microns. Microparticles or bead supports may be made of a variety of inorganic or organic materials including, but not limited to, glass (e.g., controlled pore glass), silica, zirconia, cross-linked polystyrene, polyacrylate, polymethylmethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments, a population of microparticles having different shapes sizes or colors is used. The microparticles can optionally be encoded, e.g., with quantum dots such that each microparticle or group of microparticles can be individually or uniquely identified.

Magnetic beads (e.g., Dynabeads from Dynal, Oslo, Norway) can have a size in a range of 1 micron to 100 microns, such as 2 microns to 100 microns. The magnetic beads can be formed of inorganic or organic materials including, but not limited to, glass (e.g., controlled pore glass), silica, zirconia, cross-linked polystyrene, polystyrene, or a combination thereof.

In some embodiments, a bead support is functionalized for attaching a population of first primers. In some embodiments, a bead is any size that can fit into a reaction chamber. For example, one bead can fit in a reaction chamber. In some embodiments, more than one bead fit in a reaction chamber. In some embodiments, the smallest cross-sectional length of a bead (e.g., diameter) is about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In general, the bead support can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

Figure 5:
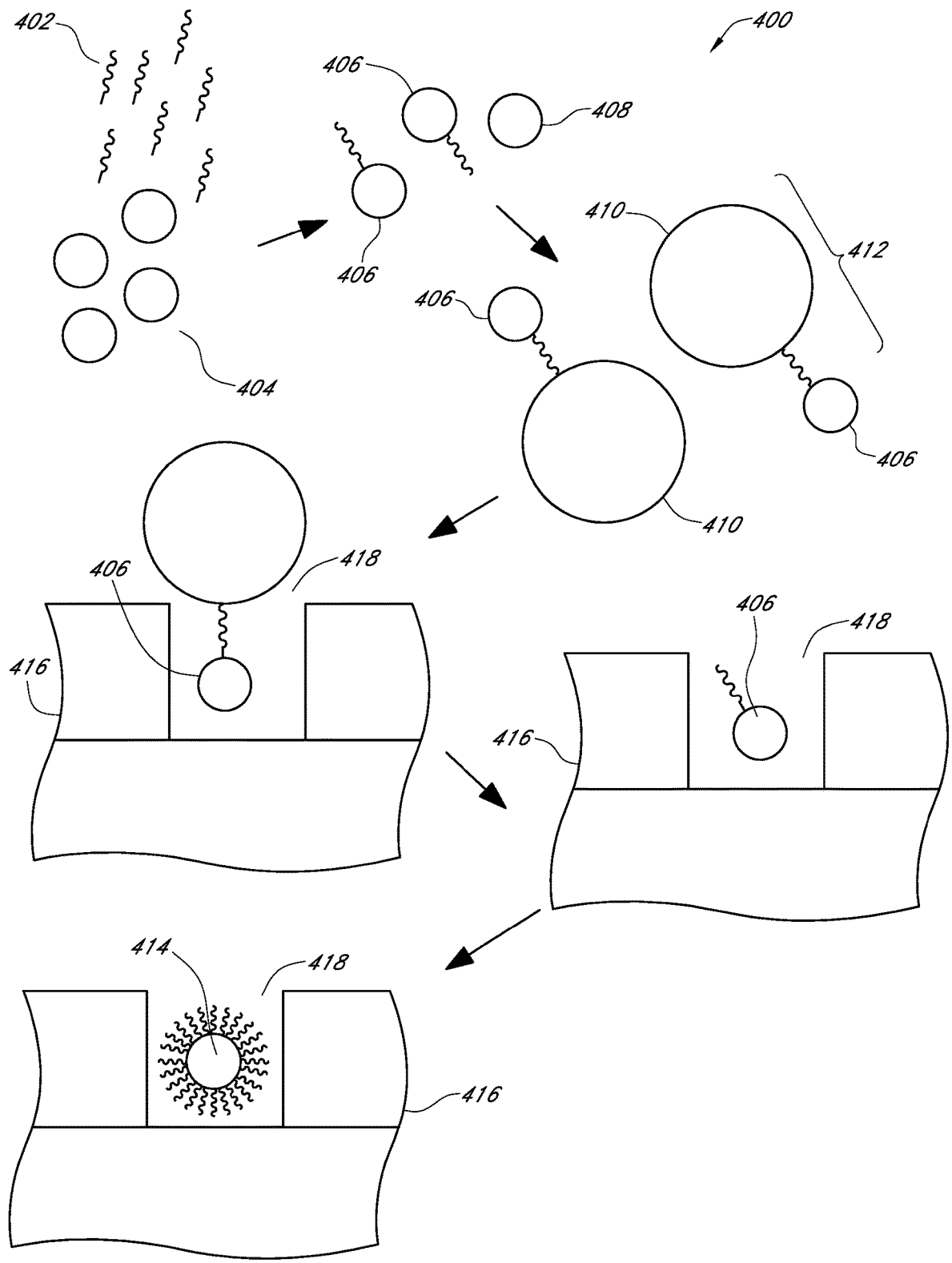
FIG. 5 includes an illustration of an example method for preparing a sequencing device.

As illustrated in FIG. 5, a plurality of bead supports 404 can be placed in a solution along with a plurality of polynucleotides 402 (target or template polynucleotides). The plurality of bead supports 404 can be activated or otherwise prepared to bind with the polynucleotides 402. For example, the bead supports 404 can include an oligonucleotide (capture primer) complementary to a portion of a polynucleotide of the plurality of polynucleotides 402. In another example, the bead supports 404 can be modified with target polynucleotides 402 using techniques such as biotin-streptavidin binding.

In some embodiments, the template nucleic acid molecules (template polynucleotides or target polynucleotides) can be derived from a sample that can be from a natural or non-natural source. The nucleic acid molecules in the sample can be derived from a living organism or a cell. Any nucleic acid molecule can be used, for example, the sample can include genomic DNA covering a portion of or an entire genome, mRNA, or miRNA from the living organism or cell. In other embodiments, the template nucleic acid molecules can be synthetic or recombinant. In some embodiments, the sample contains nucleic acid molecules having substantially identical sequences or having a mixture of different sequences. Illustrative embodiments are typically performed using nucleic acid molecules that were generated within and by a living cell. Such nucleic acid molecules are typically isolated directly from a natural source such as a cell or a bodily fluid without any in vitro amplification. Accordingly, the sample nucleic acid molecules are used directly in subsequent steps. In some embodiments, the nucleic acid molecules in the sample can include two or more nucleic acid molecules with different sequences.

The methods can optionally include a target enrichment step before, during, or after the library preparation and before a pre-seeding reaction. Target nucleic acid molecules, including target loci or regions of interest, can be enriched, for example, through multiplex nucleic acid amplification or hybridization A variety of methods can be used to perform multiplex nucleic acid amplification to generate amplicons, such as multiplex PCR, and can be used in an embodiment. Enrichment by any method can be followed by a universal amplification reaction before the template nucleic acid molecules are added to a pre-seeding reaction mixture. Any of the embodiments of the present teachings can include enriching a plurality of at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 target nucleic acid molecules, target loci, or regions of interest. In any of the disclosed embodiments, the target loci or regions of interest can be at least 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, 500, 600, 700, 800, 900, or 1,000 nucleotides in length and include a portion of or the entirety of the template nucleic acid molecule. In other embodiments, the target loci or regions of interest can be between about 1 and 10,000 nucleotides in length, for example between about 2 and 5,000 nucleotides, between about 2 and 3,000 nucleotides, or between about 2 and 2,000 nucleotides in length. In any of the embodiments of the present teachings, the multiplex nucleic acid amplification can include generating at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 copies of each target nucleic acid molecule, target locus, or region of interest.

In some embodiments, after the library preparation and optional enrichment step, the library of template nucleic acid molecules can be templated onto one or more supports. The one or more supports can be templated in two reactions, a seeding reaction to generate pre-seeded solid supports and a templating reaction using the one or more pre-seeded supports to further amplify the attached template nucleic acid molecules. The pre-seeding reaction is typically an amplification reaction and can be performed using a variety of methods. For example, the pre-seeding reaction can be performed in an RPA reaction, a template walking reaction, or a PCR. In an RPA reaction, template nucleic acid molecules are amplified using a recombinase, polymerase, and optionally a recombinase accessory protein in the presence of primers and nucleotides. The recombinase and optionally the recombinase accessory protein can dissociate at least a portion of a double stranded template nucleic acid molecules to allow primers to hybridize that the polymerase can then bind to initiate replication. In some embodiments, the recombinase accessory protein can be a single-stranded binding protein (SSB) that prevents the re-hybridization of dissociated template nucleic acid molecules. Typically, RPA reactions can be performed at isothermal temperatures. In a template walking reaction, template nucleic acid molecules are amplified using a polymerase in the presence of primers and nucleotides in reaction conditions that allow at least a portion of double-stranded template nucleic acid molecules to dissociate such that primers can hybridize and the polymerase can then bind to initiate replication. In PCR, the double-stranded template nucleic acid molecules are dissociated by thermal cycling. After cooling, primers bind to complementary sequences and can be used for replication by the polymerase. In any of the aspects of the present teachings, the pre-seeding reaction can be performed in a pre-seeding reaction mixture, which is formed with the components necessary for amplification of the template nucleic acid molecules. In any of the disclosed aspects, the pre-seeding reaction mixture can include some or all of the following: a population of template nucleic acid molecules, a polymerase, one or more solid supports with a population of attached first primers, nucleotides, and a cofactor such as a divalent cation. In some embodiments, the pre-seeding reaction mixture can further include a second primer and optionally a diffusion-limiting agent. In some embodiments, the population of template nucleic acid molecules comprise template nucleic acid molecules joined to at least one adaptor sequence which can hybridize to the first or second primers. In some embodiments, the reaction mixture can form an emulsion, as in emulsion RPA or emulsion PCR. In pre-seeding reactions carried out by RPA reactions, the pre-seeding reaction mixture can include a recombinase and optionally a recombinase accessory protein. The various components of the reaction mixture are discussed in further detail herein.

In a particular embodiment of seeding, the hydrophilic particles and polynucleotides are subjected to polymerase chain reaction (PCR) amplification or recombinase polymerase amplification (RPA). In an example, the particles 404 include a capture primer complementary to a portion of the template polynucleotide 402. The template polynucleotide can hybridize to the capture primer. The capture primer can be extended to form beads 406 that include a target polynucleotide attached thereto. Other beads may remain unattached to a target nucleic acid and other template polynucleotide can be free floating in solution.

In an example, the bead support 406 including a target polynucleotide can be attached to a magnetic bead 410 to form a bead assembly 412. In particular, the magnetic bead 410 is attached to the bead support 406 by a double stranded polynucleotide linkage In an example, a further probe including a linker moiety can hybridize to a portion of the target polynucleotide on the bead support 406. The linker moiety can be attached to a complementary linker moiety on the magnetic bead 410. In another example, the template polynucleotide used to form the target nucleic acid attached to beads 406 can include a linker moiety that attaches to the magnetic bead 410. In another example, the template polynucleotide complementary to target polynucleotide attached to the bead support 406 can be generated from a primer that is modified with a linker that attaches to the magnetic bead 410.

The linker moiety attached to the polynucleotide and the linker moiety attached to the magnetic bead can be complementary to and attach to each other. In an example, the linker moieties have affinity and can include: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement. In a particular example, the linker moiety attached to the polynucleotide includes biotin and the linker moiety attached to the magnetic bead includes streptavidin.

The bead assemblies 412 can be applied over a substrate 416 of a sequencing device that includes wells 418. In an example, a magnetic field can be applied to the substrate 416 to draw the magnetic beads 410 of the bead assembly 412 towards the wells 418. The bead support 406 enters the well 418. For example, a magnet can be moved in parallel to a surface of the substrate 416 resulting in the deposition of the bead support 406 in the wells 418.

The bead assembly 412 can be denatured to remove the magnetic bead 410 leaving the bead support 406 in the well 418. For example, hybridized double-stranded DNA of the bead assembly 412 can be denatured using thermal cycling or ionic solutions to release the magnetic bead 410 and template polynucleotides having a linker moiety attached to the magnetic bead 410. For example, the double-stranded DNA can be treated with low ion-content aqueous solutions, such as deionized water, to denature and separate the strands. In an example, a foam wash can be used to remove the magnetic beads.

Optionally, the target polynucleotides 406 can be amplified, referred to herein as templating, while in the well 418, to provide a bead support 414 with multiple copies of the target polynucleotides. In particular, the bead 414 has a monoclonal population of target polynucleotides. Such an amplification reactions can be performed using polymerase chain reaction (PCR) amplification, recombination polymerase amplification (RPA) or a combination thereof. Alternatively, amplification can be performed prior to depositing the bead support 414 in the well.

In a particular embodiment, an enzyme such as a polymerase is present, bound to, or is in close proximity to the particles or beads. In an example, a polymerase is present in solution or in the well to facilitate duplication of the polynucleotide. A variety of nucleic acid polymerase may be used in the methods described herein. In an example embodiment, the polymerase can include an enzyme, fragment, or subunit thereof, which can catalyze duplication of the polynucleotide. In another embodiment, the polymerase can be a naturally occurring polymerase, recombinant polymerase, mutant polymerase, variant polymerase, fusion or otherwise engineered polymerase, chemically modified polymerase, synthetic molecules, or analog, derivative or fragment thereof. Example enzymes, solutions, compositions, and amplification methods can be found in WO2019/094,524, titled "METHODS AND COMPOSITIONS FOR MANIPULATING NUCLEIC ACIDS", which is incorporated herein by reference in its entirety.

While the polynucleotides of bead support 414 are illustrated as being on a surface, the polynucleotides can extend within the bead support 414. Hydrogel and hydrophilic particles having a low concentration of polymer relative to water can include polynucleotide segments on the interior of and throughout the bead support 414 or polynucleotides can reside in pores and other openings. In particular, the bead support 414 can permit diffusion of enzymes, nucleotides, primers, and reaction products used to monitor the reaction. A high number of polynucleotides per particle produces a better signal.

In an example embodiment, the bead support 414 can be utilized in a sequencing device. For example, a sequencing device 416 can include an array of wells 418.

In an example, a sequencing primer can be added to the wells 418 or the bead support 414 can be pre-exposed to the primer prior to placement in the well 418. In particular, the bead support 414 can include bound sequencing primer. The sequencing primer and polynucleotide form a nucleic acid duplex including the polynucleotide (e.g., a template nucleic acid) hybridized to the sequencing primer. The nucleic acid duplex is an at least partially double-stranded polynucleotide. Enzymes and nucleotides can be provided to the well 418 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 416 and can migrate to the well 418. Excitation energy can be also provided to the well 418. When a nucleotide is captured by a polymerase and added to the end of an extending primer, a label of the nucleotide can fluoresce, indicating which type of nucleotide is added.

In an alternative example, solutions including a single type of nucleotide can be fed sequentially In response to nucleotide addition, the pH within the local environment of the well 418 can change. Such a change in pH can be detected by ion sensitive field effect transistors (ISFET). As such, a change in pH can be used to generate a signal indicating the order of nucleotides complementary to the polynucleotide of the particle 410.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FLT), or one or more polymeric particles loaded into a plurality of wells which are disposed over sensor pads of ionic sensors (e.g., FLT). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FLT may be a FET array. As used herein, an "array" is a planar arrangement of elements such as sensors or wells. The array may be one or two dimensional. A one-dimensional array can be an array having one column (or row) of elements in the first dimension and a plurality of columns (or rows) in the second dimension. The number of columns (or rows) in the first and second dimensions may or may not be the same. The FLT or array can comprise $10^2$, $10^3$, $10^4$, $10^5$, $10^6$, $10^7$ or more FETs.

In embodiments, one or more microfluidic structures can be fabricated above the FET sensor array to provide for containment or confinement of a biological or chemical reaction. For example, in one implementation, the microfluidic structure(s) can be configured as one or more wells (or wells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FLT sensors and reaction wells.

Returning to FIG. 5, in another example, a well 418 of the array of wells can be operatively connected to measuring devices. For example, for fluorescent emission methods, a well 418 can be operatively coupled to a light detection device. In the case of ionic detection, the lower surface of the well 418 may be disposed over a sensor pad of an ionic sensor, such as a field effect transistor.

One example system involving sequencing via detection of ionic byproducts of nucleotide incorporation is the Ion Torrent PGM™, Proton™, S5™, or Genexus™ sequencer (Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™, Proton™, S5™, or Genexus™ sequencer detects the nucleotide incorporations by detecting the hydrogen ion byproducts of the nucleotide incorporations. The Ion Torrent PGM™, Proton™, S5™, or Genexus™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

Figure 6:
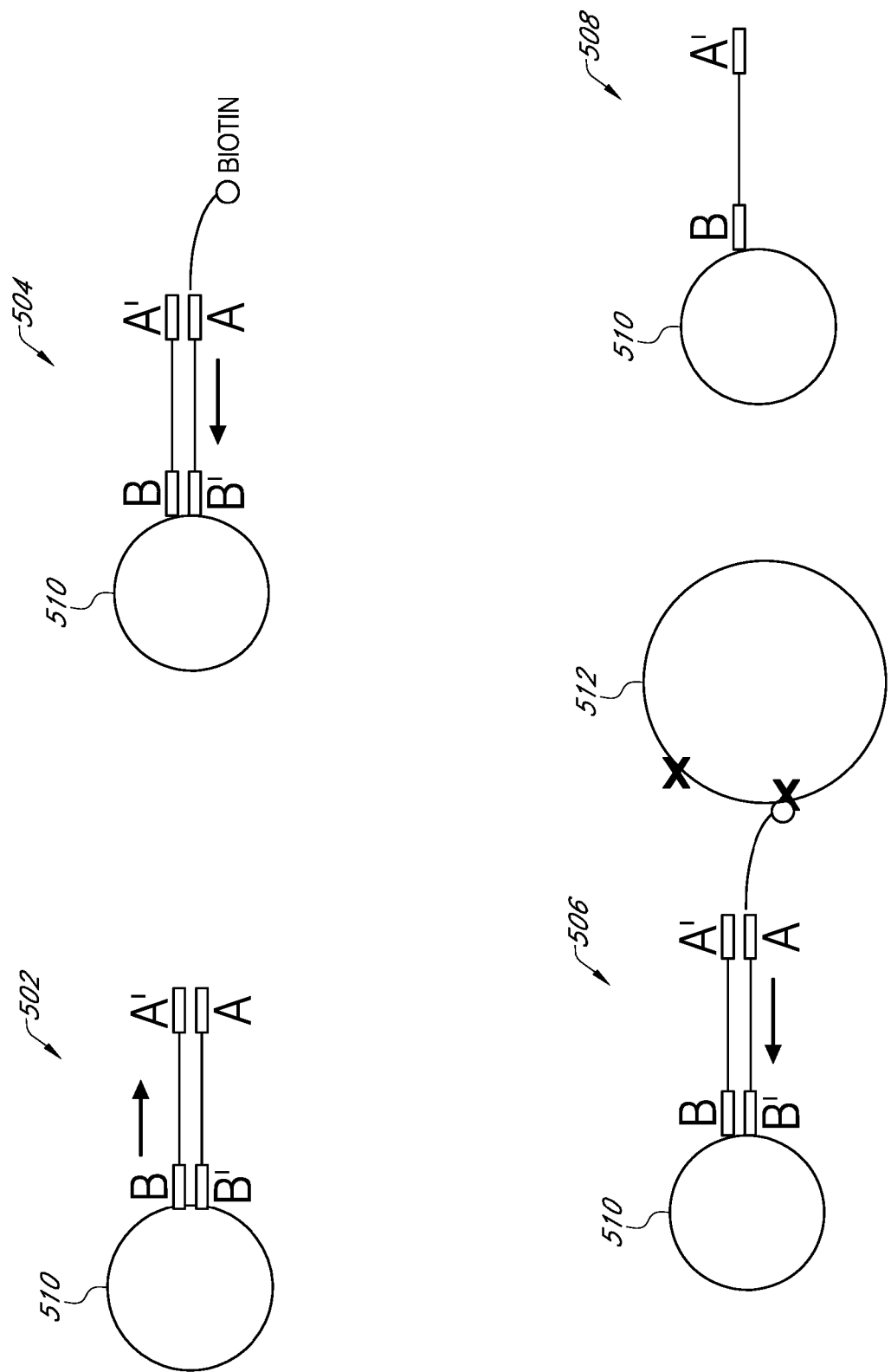
FIG. 6 illustrates example schema for preparing a bead assembly.

Seeding the bead supports and capture by the magnetic beads can be performed through various methods. For example, turning to FIG. 6 at 502, a template polynucleotide (B'-A) can be captured by a capture probe (B) attached to a bead support 510. The capture probe (B) can be extended complementary to the template polynucleotide. Optionally, the resultant double-stranded polynucleotide can be denatured removing the template nucleic acid (B'-A) and leaving a single-stranded (B-A') attached to the bead support 510. As illustrated at 504, a primer (A) modified with a linker moiety, such as biotin, can be hybridized to a portion (A') of the nucleic acid (B-A') attached to the bead support 510. Optionally, the primer (A) can be extended to form a complementary nucleic acid (A-B').

As illustrated 506, a magnetic bead 512 can be introduced to the solution. The magnetic bead 512 can include a linker complementary to the linker moiety attached to the primer (A). For example, the linker attached to the primer (A) can be biotin and the magnetic bead 512 can be coated with streptavidin. As described above, the magnetic bead 512 can be utilized to clean the solution and to assist with deposition of the bead support 510 and the attached nucleic acid (B-A') into a well of a sequencing device. As illustrated 508, double-stranded polynucleotide can be denatured, resulting in the dehybridization of the nucleic acid (B'-A) from the nucleic acid (B-A') attached to the bead support 510. As such, the bead support 510 is deposited into the wells of the sequencing device and has a single stranded target nucleic acid (B-A'). Alternatively, the linker modified probe (A) may not be extended to form a complementary polynucleotide with a length the polynucleotide (B-A'). Extension reactions can be carried out using polymerase chain reaction (PCR), recombinase polymerase amplification (RPA), or other amplification reactions.

Instrument

Figure 7:
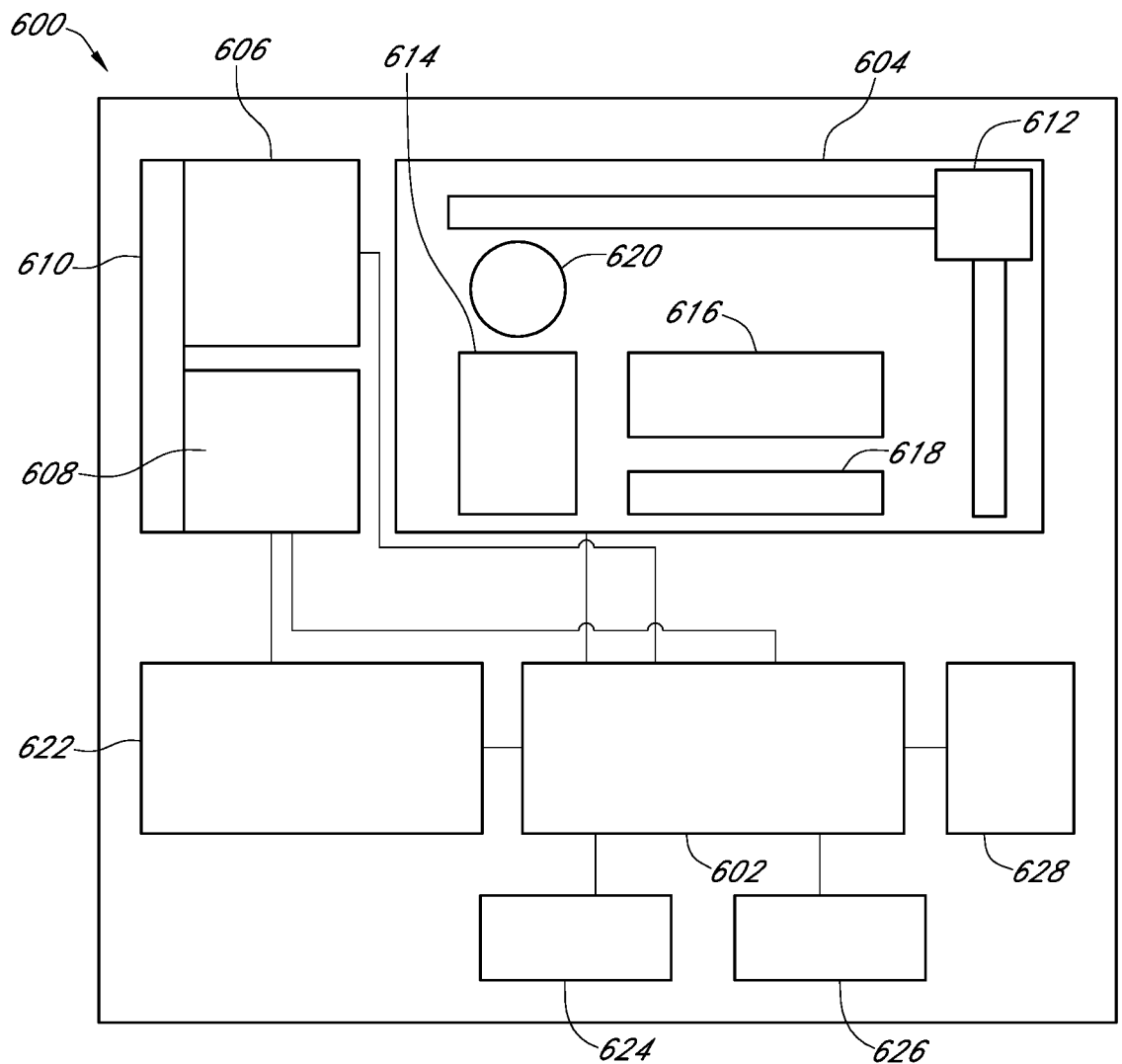
FIG. 7 includes an illustration of an example sequencing system.

FIG. 7 includes an illustration of an exemplary sequencing instrument system 600, which includes a controller 602 in communication with a preparation deck 604, a loading station 606, and a sequencing station 608. The preparation deck 604 can include a pipetting robot 612 that can access samples 614, reagents and solutions 616, a thermocycler 618 and other devices 620, such as a magnetic separator or a centrifuge. Target sequences prepared at the preparation deck 604 can be provided to the templating zone, such as loading station 606. For example, the preparation deck 604 can provide seeded substrates including target sequences that are provided to the loading station 606 to be loaded onto a sensor device.

Once loaded, the sensor device including the target sequences can be transported to the sequencing zone, such as sequencing station 608, utilizing the slide mechanism 610. The sequencing station 608 can include fluidics and an electronic interface to interact with the sensor device to sense the addition of nucleotides during a sequencing-by-synthesis reaction. Data gathered from the sensing device can be provided to a sequencing computer 622 which can perform base calling, read alignment, and variant calling.

The controller 602 can further communicate with a user interface 624 such as a monitor, keyboard, mouse, touchscreen, or any combination thereof, among other interfaces. Further, the controller 602 can communicate with a network interface that may access a local area network, wide area network, or global network. The network interface 626 can be a wired interface or a wireless interface using various standard communication protocols. Further, the system can be powered by a power source 628.

Figure 8:
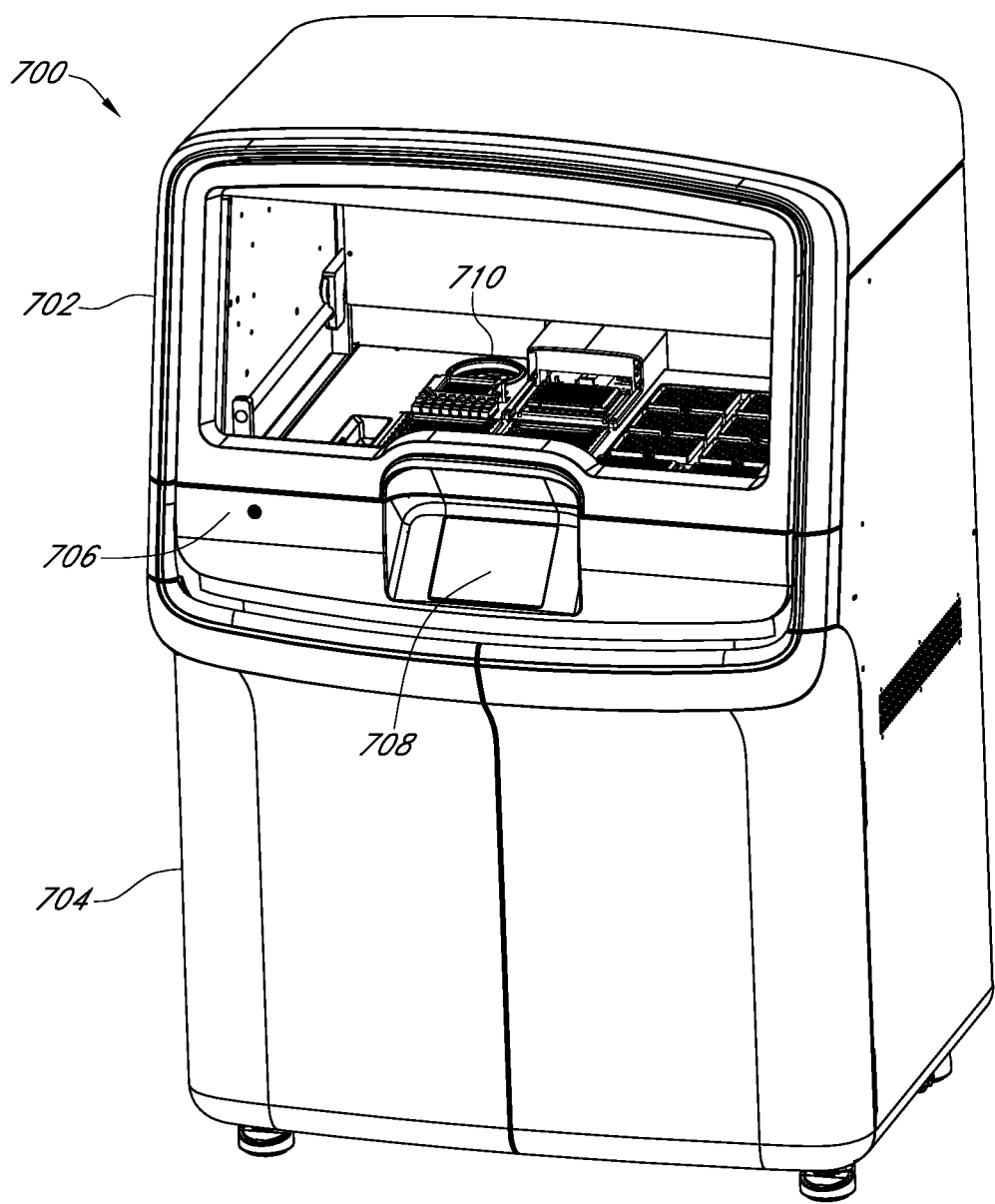
FIG. 8 includes an illustration of an example instrument.

FIG. 8 includes an illustration of an example instrument 700 incorporating a three-axis pipetting robot. In an example, the instrument 700 can be a sequencer incorporating a sample prep preparation platform. For example, the instrument 700 can include an upper portion 702 and a lower portion 704. The upper portion can include a door 706 to access a deck 710 on which samples, reagent containers, and other consumables are placed. The lower portion can include a cabinet for storing additional reagent solutions and other parts of the instrument 700. In addition, the instrument can include a user interface, such as a touchscreen display 708.

In a particular example, the instrument 700 can be a sequencing instrument. In some embodiments, the sequencing instrument includes a top section, a display screen, and a bottom section. In some embodiments, the top section may include a deck supporting components of the sequencing instrument and consumables, including a sample preparation section, a sequencing chip and reagent strip tubes and carriers. In some embodiments, the bottom section may house reagent bottles used for sequencing and a waste container.

Figure 9:
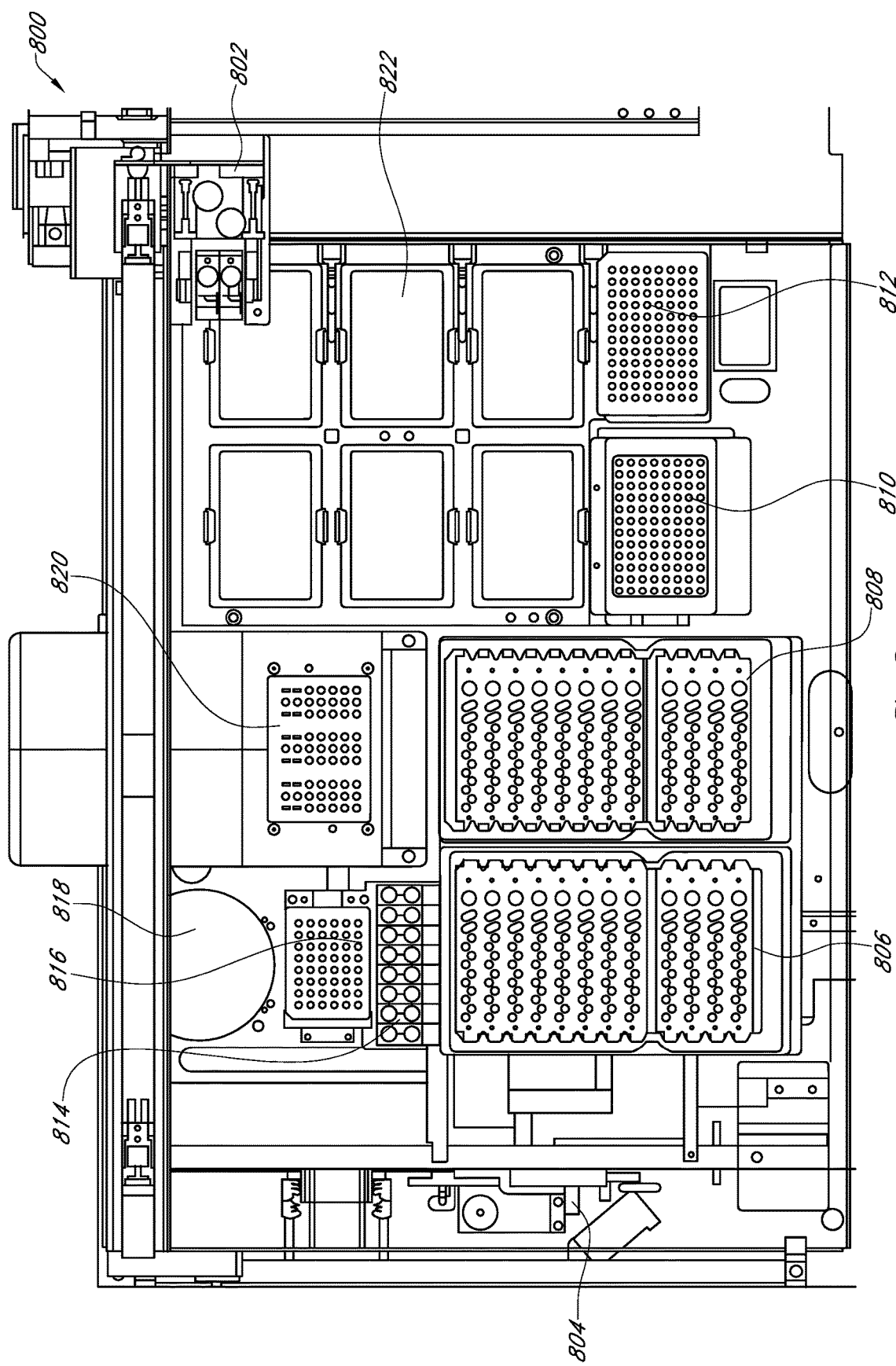
FIG. 9 includes an illustration of an example deck of an instrument.

An example instrument deck 710 is illustrated in FIG. 9 as instrument deck 800. The deck 800 is housed in the top section of the instrument in the view of the camera or cameras. The sample preparation deck may include a plurality of locations configured to receive reagent strips, supplies, a sequencing chip, and other consumables. As used herein, consumables are components used by the instrument that are replaced periodically as they are used. For example, consumables include reagent and solution strips or containers, pipette tips, microwell arrays, and flow cells and associated sensors, among other disposable components not part of the permanent components of the instrument.

In an example, the system 800 includes a pipetting robot 802 that accesses various reagent strips and containers, pipette tips, microwell arrays, and other consumables to implement a test. Further, the system can include mechanisms 804 for carrying out testing. Example mechanisms 804 include mechanical conveyors or slides and fluidic systems.

In an example, the deck 800 includes trays 806 or 808 to receive solution or reagent strips of a particular configuration. In an example of a sequencing instrument, the tray 806 can be used for library and template solutions in appropriately configured strips, and the tray 808 can receive library and template reagents in the appropriate configuration.

Further, the instrument can be configured to receive microwell arrays 810 and 812 at particular locations on the deck. For example, a sample can be supplied in an array of wells, such as microwell array 812. In another example, the system can be configured to receive additional reagents 814 in a different strip configuration. In another example, reagent solutions can be provided in an array 816. In a further example, container arrays 820 can be provided in conjunction with instrumentation, such as a thermocycler. Further, the system can include other instrumentation, such as a centrifuge, that may be supplied with consumables, such as tubes. Further, trays can be provided to receive pipetting tips 822.

Chip and Slide Mechanism

Figure 10:
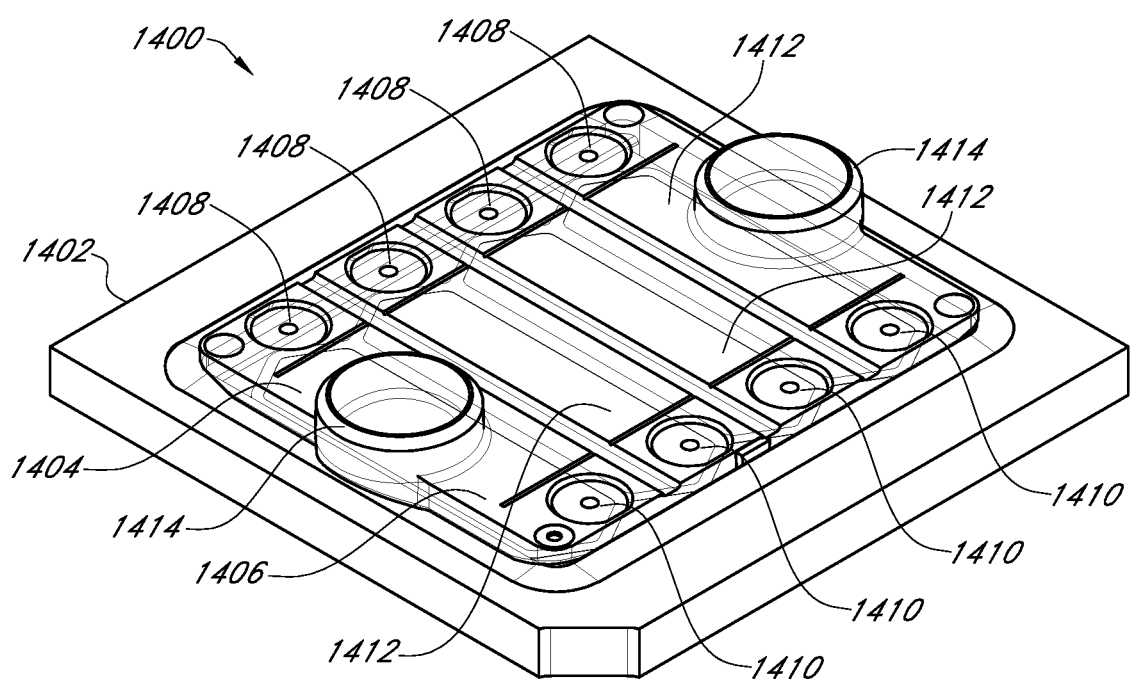
FIG. 10 and FIG. 11 include illustrations of an example sensor device.
Figure 11:
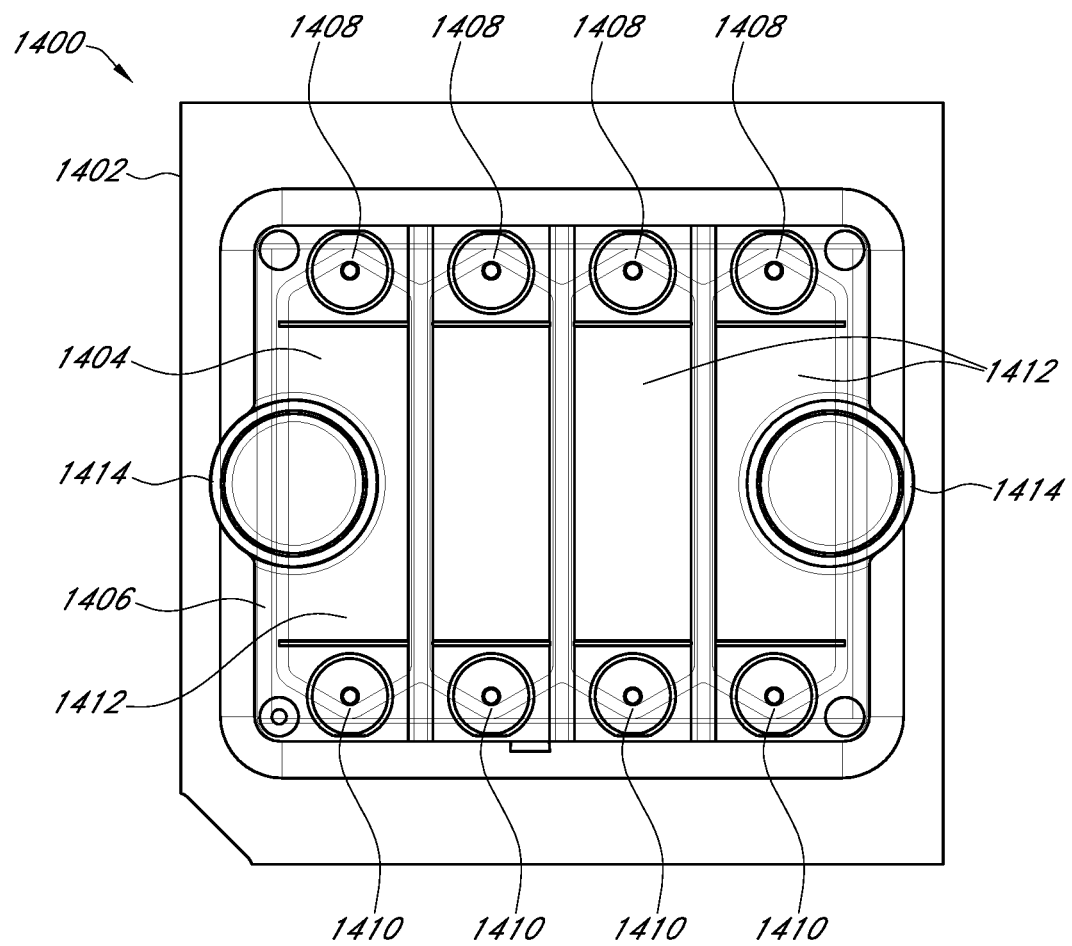

In an example, the biosensor and flow cell are an example of a sensor device. FIG. 10 and FIG. 11 illustrate an example sensor device 1400, such as a microchip including a flow cell. For example, the sensor device 1400 includes a substrate 1402 securing a die 1404 that has a plurality of microwells in fluid communication with a sensor array. A flow cell 1406 is secured over the substrate, providing a volume over the die 1404.

In an example, the flow cell 1406 includes a set of fluid inlets 1408 and a set of fluid outlets 1410. In particular, the flow cell 1406 can be divided into lanes 1412. Each lane is individually accessed by a respective fluid inlet 1408 and fluid outlet 1410. Alternatively, the flow cell can include a single set of flow inlets and have a single lane.

As illustrated, the sensor device 1400 includes four lanes 1412. Alternatively, the sensor device 1400 can include less than four lanes or more than four lanes. For example, the sensor device 1400 can include between 1 and 10 lanes, such as between 2 and 8 lanes, or 4 to 6 lanes. The lanes 1412 can be fluidically isolated from each other. As such, the lanes 1412 can be used at separate times, concurrently, or simultaneously, depending upon aspects of a run plan.

The sensor device 1400 can further include guides structures 1414, for example, formed as part of the flow cell 1406, to engage complementary structures on a fluidic coupler. Such guide structures 1414 assist with aligning the fluid inlets 1408 and fluid outlet 1410 with associated ports on a fluidic coupler.

Figure 12:
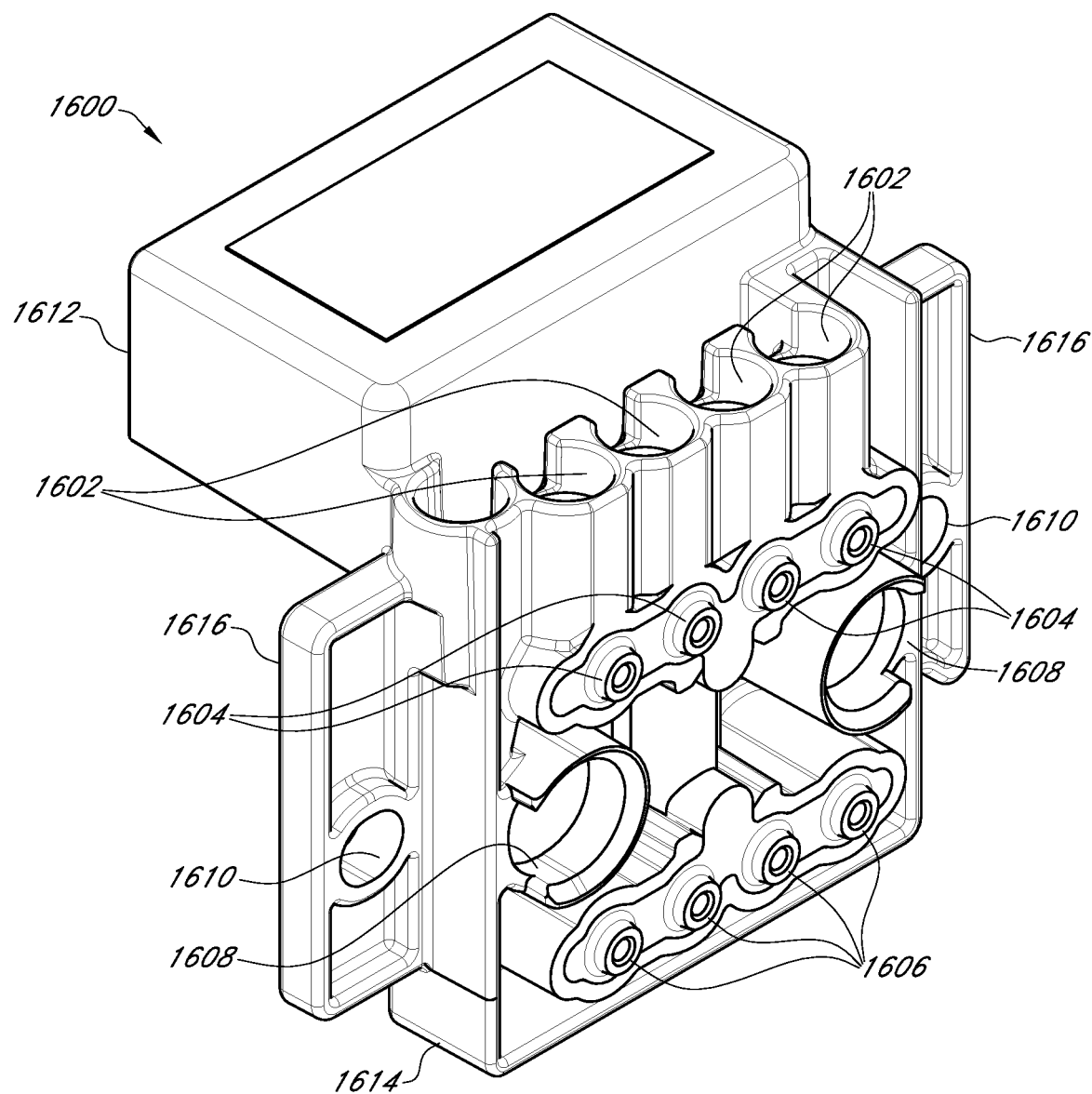
FIG. 12, FIG. 13, and FIG. 14 include illustrations of an example fluidic coupler.
Figure 13:
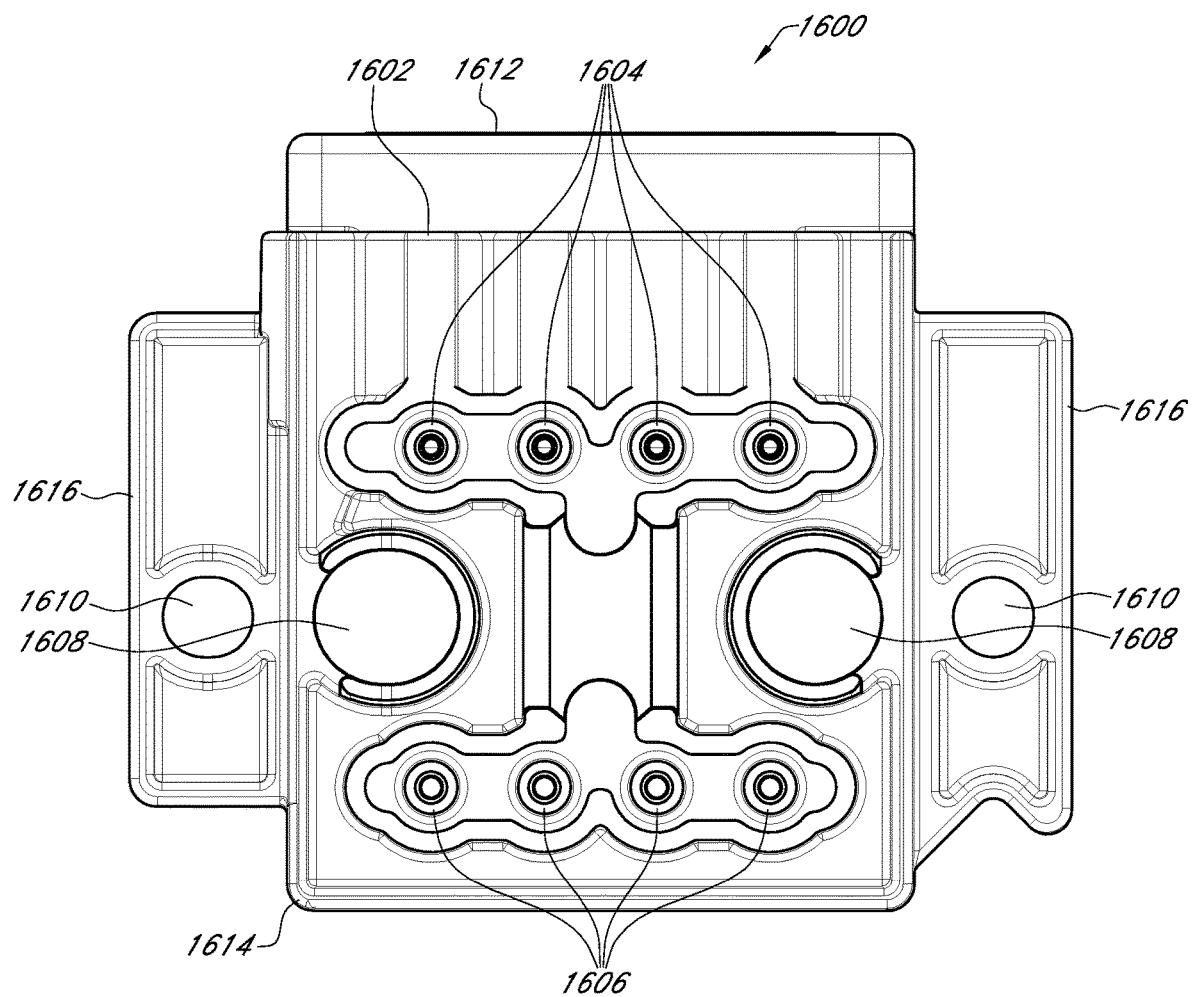
Figure 14:
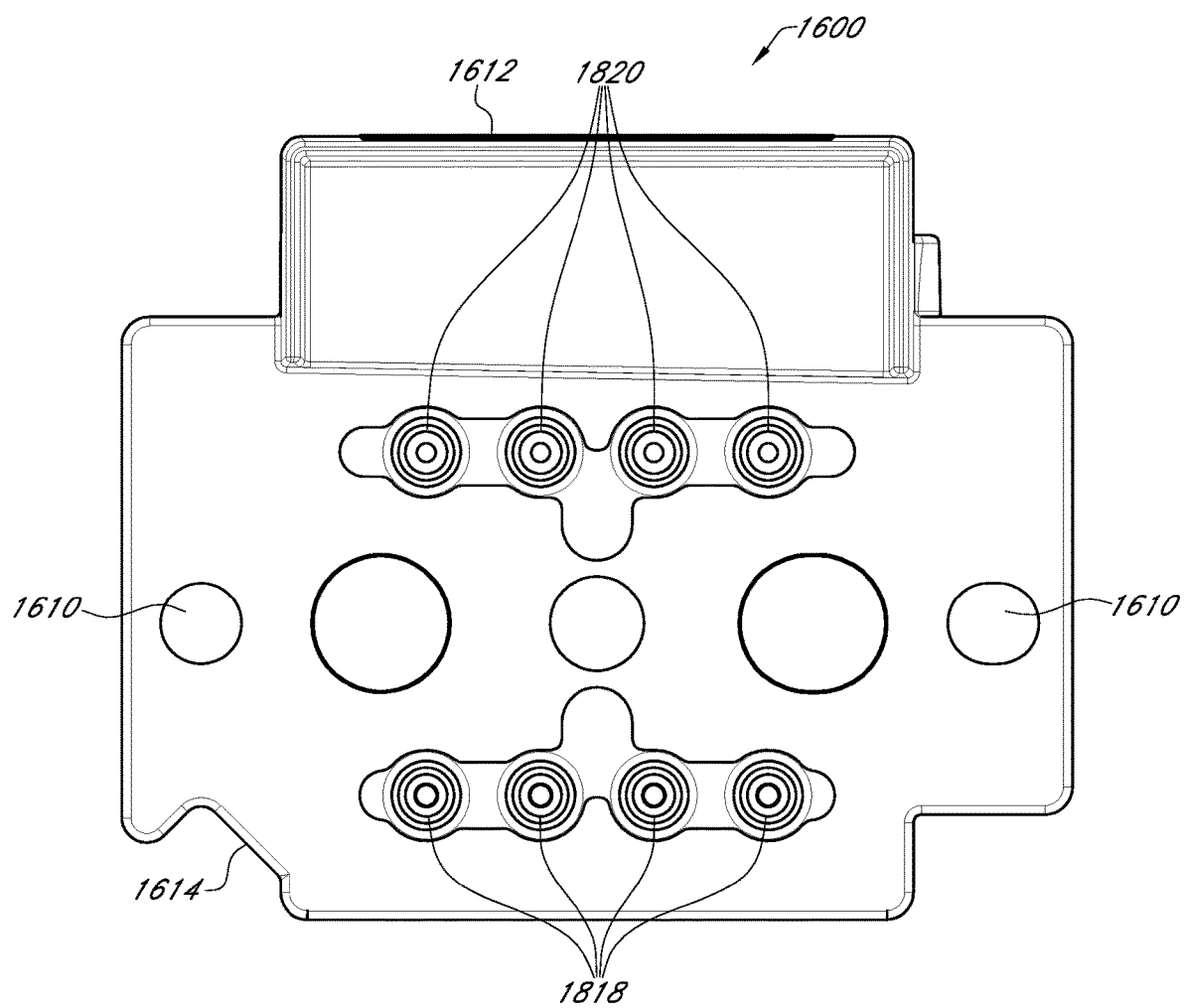

FIG. 12, FIG. 13, and FIG. 14 include illustrations of an example fluidic coupler 1600. The fluidic coupler 1600 includes a body 1614 defining fluidic pathways between sets of ports. Further, the fluidic coupler 1600 can include a connector section 1612 to engage a mechanical assembly and assist with positioning the fluidic coupler 1600 relative to the mechanical assembly. In another example, the fluidic coupler 1600 can include wings 1616 defining reference holes 1610 to engage guide rods of a mechanical assembly, further assisting with positioning the fluidic coupler 1600 relative to a sensor device.

The body 1614 of the fluidic coupler 1600 can define openings 1602 that are in fluidic communication with a first set of ports 1604. The openings 1602 can be sized to receive an end of a pipette tip and allow pipetting of a fluid composition into the opening 1602. The openings 1602 are in fluidic communication with a set of ports 1604, which are configured to engage inlets 1408 of a sensor device 1400 (FIG. 10). The fluidic coupler 1600 can further define a second set of ports 1606 that can engage and provide fluidic communication with outlets 1410 of the sensor device 1400 (FIG. 10).

As illustrated in FIG. 14, the system can further include a third set of ports 1818 that are in fluidic communication with the second set of ports 1606. The third set of ports 1818 can engage with a fluidic manifold of a mechanical assembly, such as the fluidic manifold 2540 illustrated in FIG. 22 and FIG. 23. Optionally, the fluidic coupler 1600 can include a fourth set of ports 1820, which can connect with a fluidic manifold or can be blocked depending upon the configuration of the mechanical assembly.

The ports 1604, 1606, 1818 or 1820 can be formed of a resilient material, such as a rubber or elastomeric polymer. In an example, the ports can be formed as an overmold using the resilient material.

Returning to FIG. 12, the body 1614 of the fluidic coupler 1600 can further include guide features 1608 complementary to guide features 1414 of the sensor device 1400 (FIG. 10).

Figure 15:
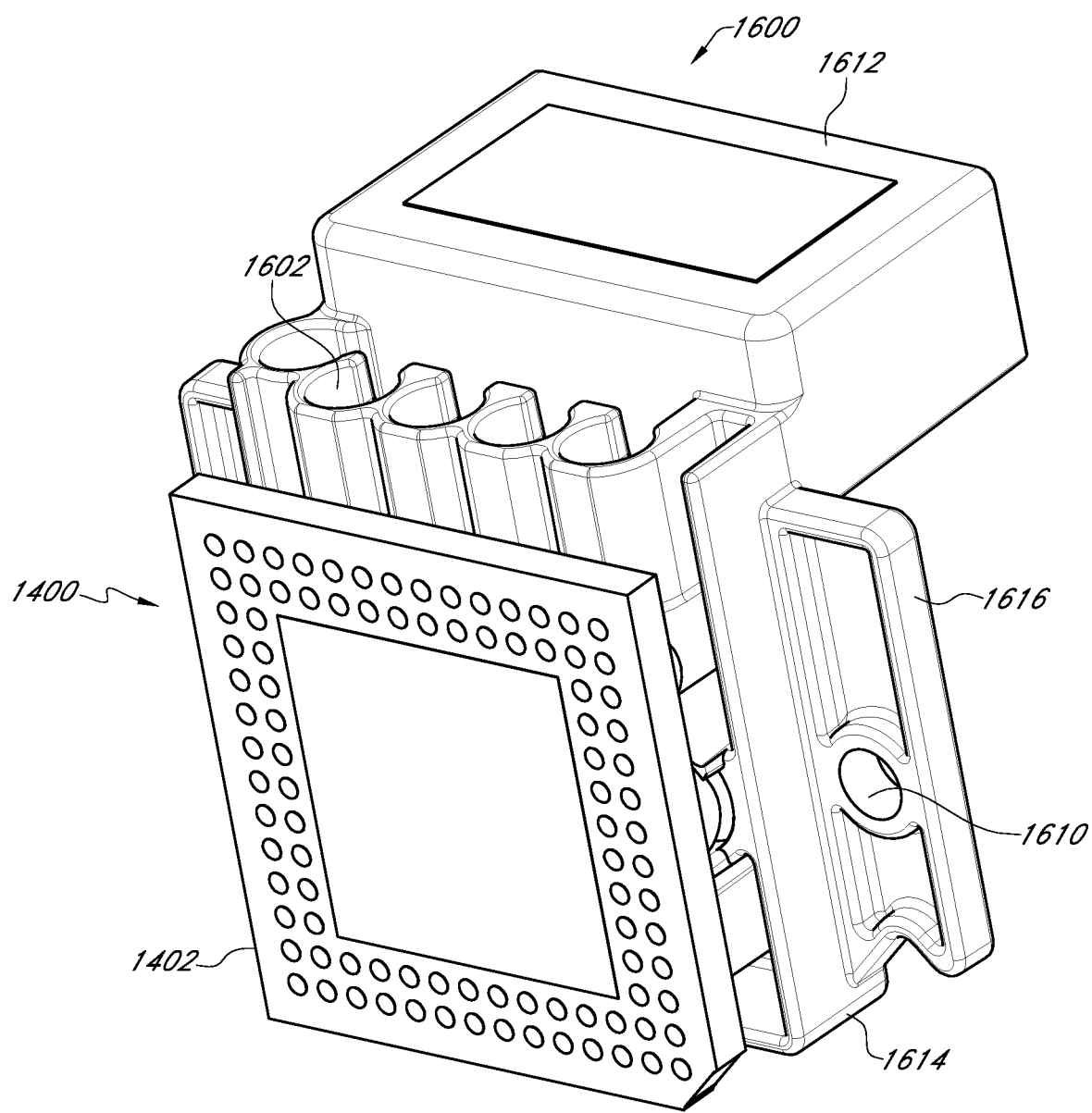
FIG. 15 and FIG. 16 include illustrations of an example interconnection between a sensor device and a fluidic coupler.
Figure 16:
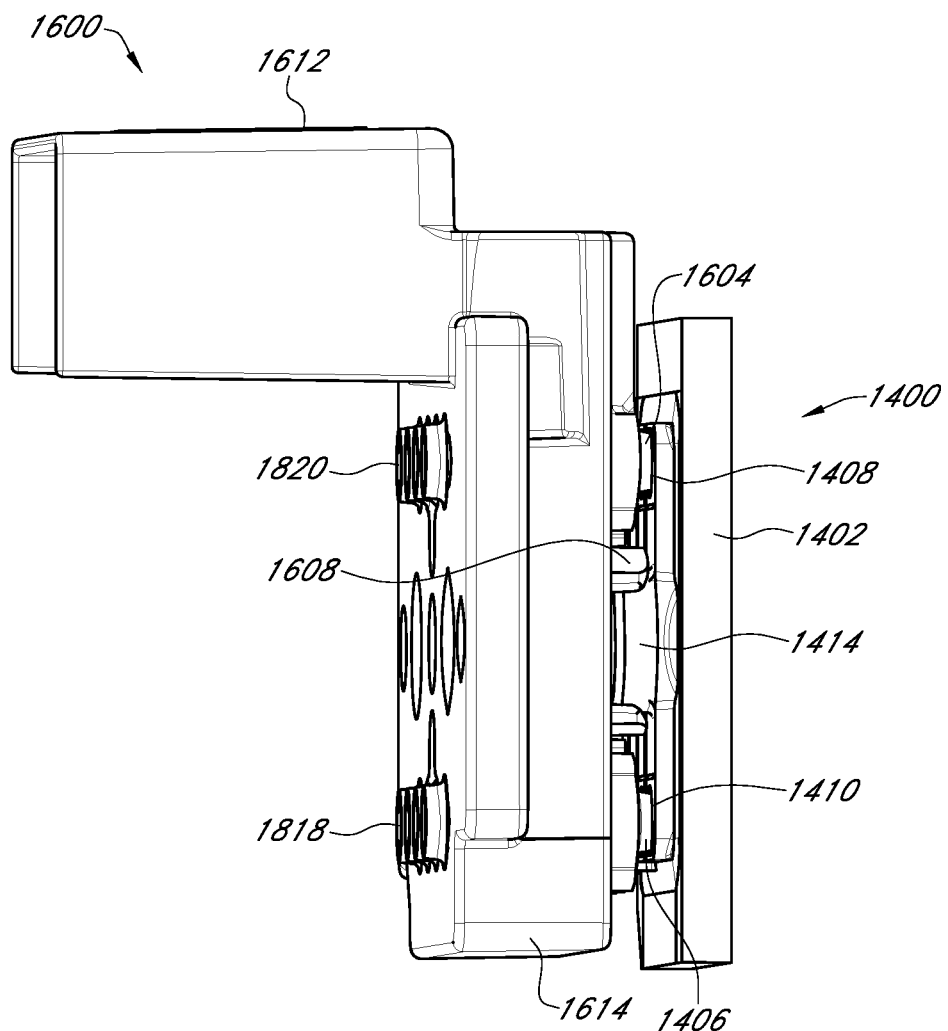

As illustrated in FIG. 15 and FIG. 16, the fluidic coupler 1600 can engage the sensor device 1400. The body 1614 of the fluidic coupler 1600 can be aligned with the substrate 1402 of the sensor device 1400 to allow the first set of ports 1604 of the fluidic coupler 1600 to be in fluid communication with the inlets 1408 of the sensor device 1400. Further, the second set of ports 1606 can be in fluidic communication with the outlets 1410 of the sensor device 1400. For example, the guide structures 1414 and 1608 can engage to align the ports with the inlets and outlets. Optionally, a third set of ports 1818 can be in fluid communication with a manifold. In a further example, a set of fluid ports 1820, optionally in fluid communication with the second set of port 1608, can be in fluid communication with a fluidic manifold.

Accordingly, fluid compositions can be pipetted into the openings 1602 in fluid communication with the first set of ports 1604, which provide the fluidic composition to the flow cell 1406 of the sensor device 1400 via the inlets 1408 of the flow cell 1406. After processing, the remainder of the fluidic composition can be drawn out of the outlet 1410 of the sensor device 1400 through the second set of ports 1606 and the third set of ports 1818 into a fluid manifold.

Figure 17:
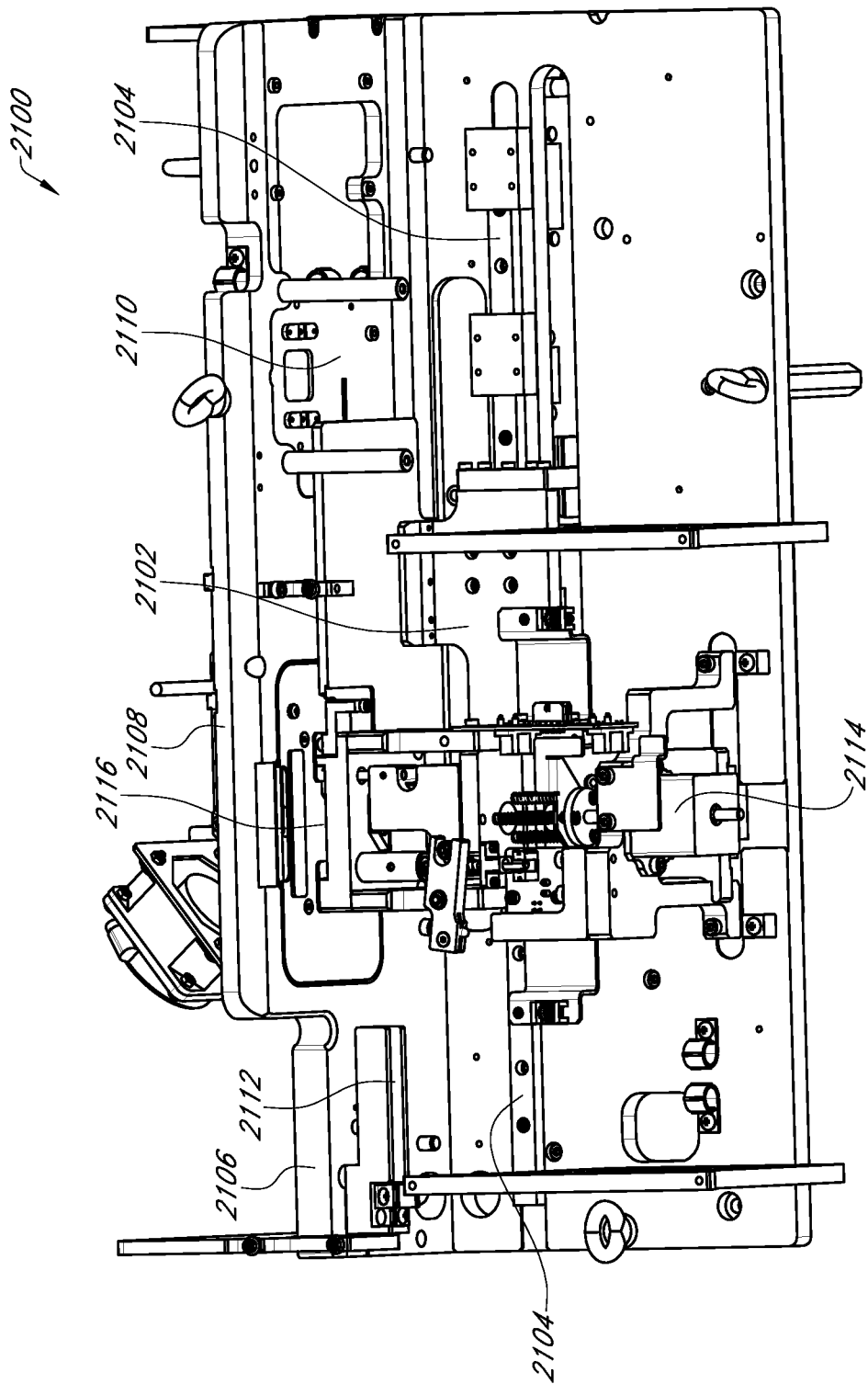
FIG. 17 and FIG. 18 include illustrations of an example mechanical system to interact with a sensor device.
Figure 18:
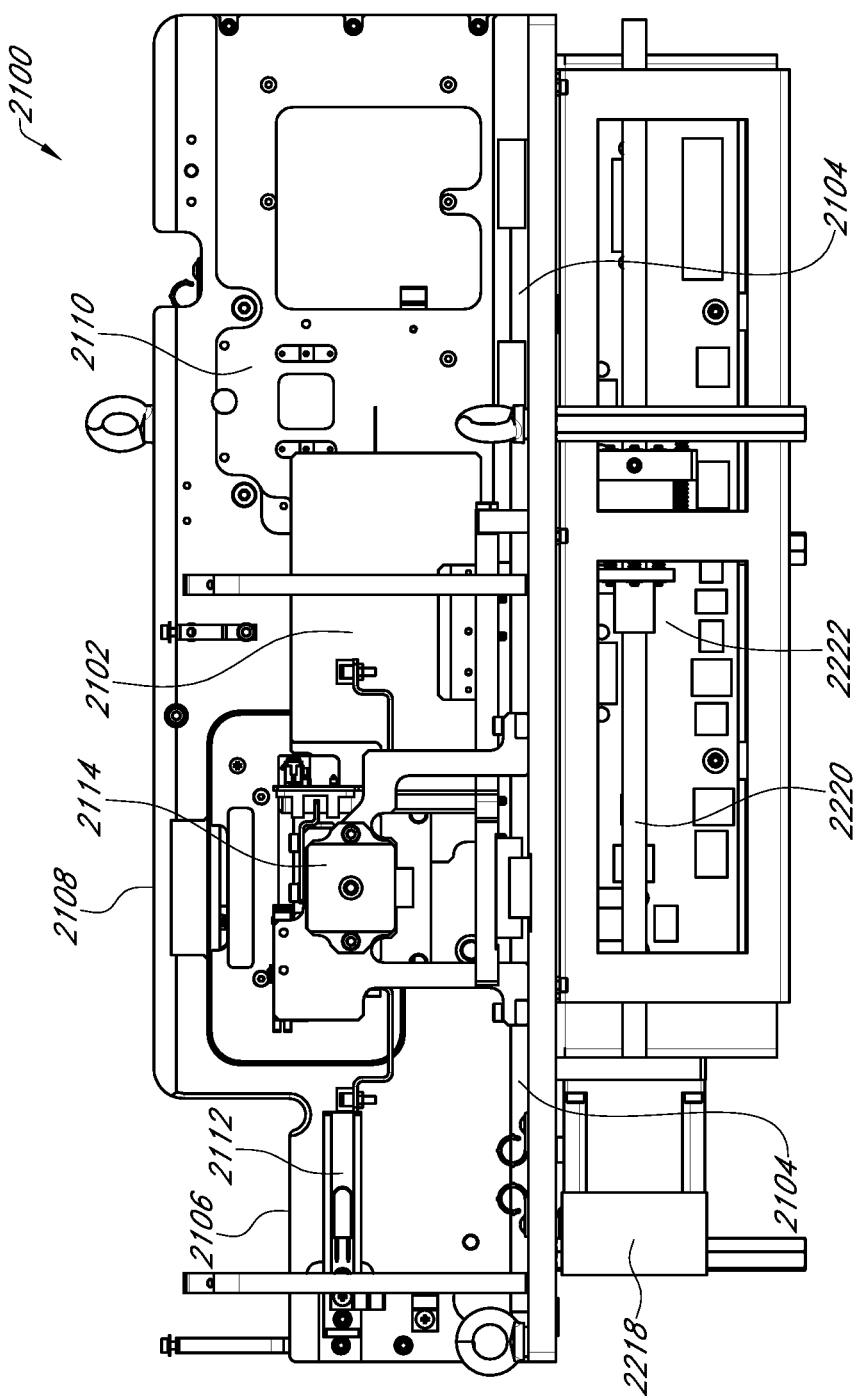

FIG. 17 and FIG. 18 include illustrations of an example mechanical system 2100 for moving a sensor device between various stations within the system. For example, a slide mechanism 2102 can move along a rail 2104 to guide a sensor device (e.g., sensor device 1400 in FIG. 10) between stations 2106, 2108, and 2110. For example, a sensor device can be inserted into the slide mechanism 2102 at station 2106. In an example, the sensor device can be inserted in a vertical orientation in which the inlet and outlet are directed to a side in contrast to upward. A sensor 2112 can detect the presence of the sensor device and allow the slide mechanism 2102 to move when the sensor device is present. For example, the slide mechanism 2102 can move the sensor device to station 2108 where the sensor device can be loaded with samples, such as through a magnetic loading method described above in relation to FIG. 5. In particular, a fluidic coupler can be inserted into space 2116 provided by the mechanical assembly 2114, which can press the fluidic coupler against the sensor device and engage the fluidic coupler with a manifold. When the magnetic loading technique is complete, the mechanical assembly 2114 can detach from the fluidic coupler, and the slide 2102 can move the sensor device to a subsequent station 2110, such as a fluidic station providing reagents and other conditions for sequencing.

As illustrated in FIG. 18, a drive 2218, such as a screw drive, can include a screw 2220 that engages a clutch 2222 to move the slide 2102 and thus the sensor device between the stations 2106, 2108, and 2110. For example, the sensor device can move through the stations 2106, 2108, and 2110 as part of a first sequencing run, and then back to station 2108 to denature and reprime, followed by moving to station 2110 for a second sequencing run.

Figure 19:
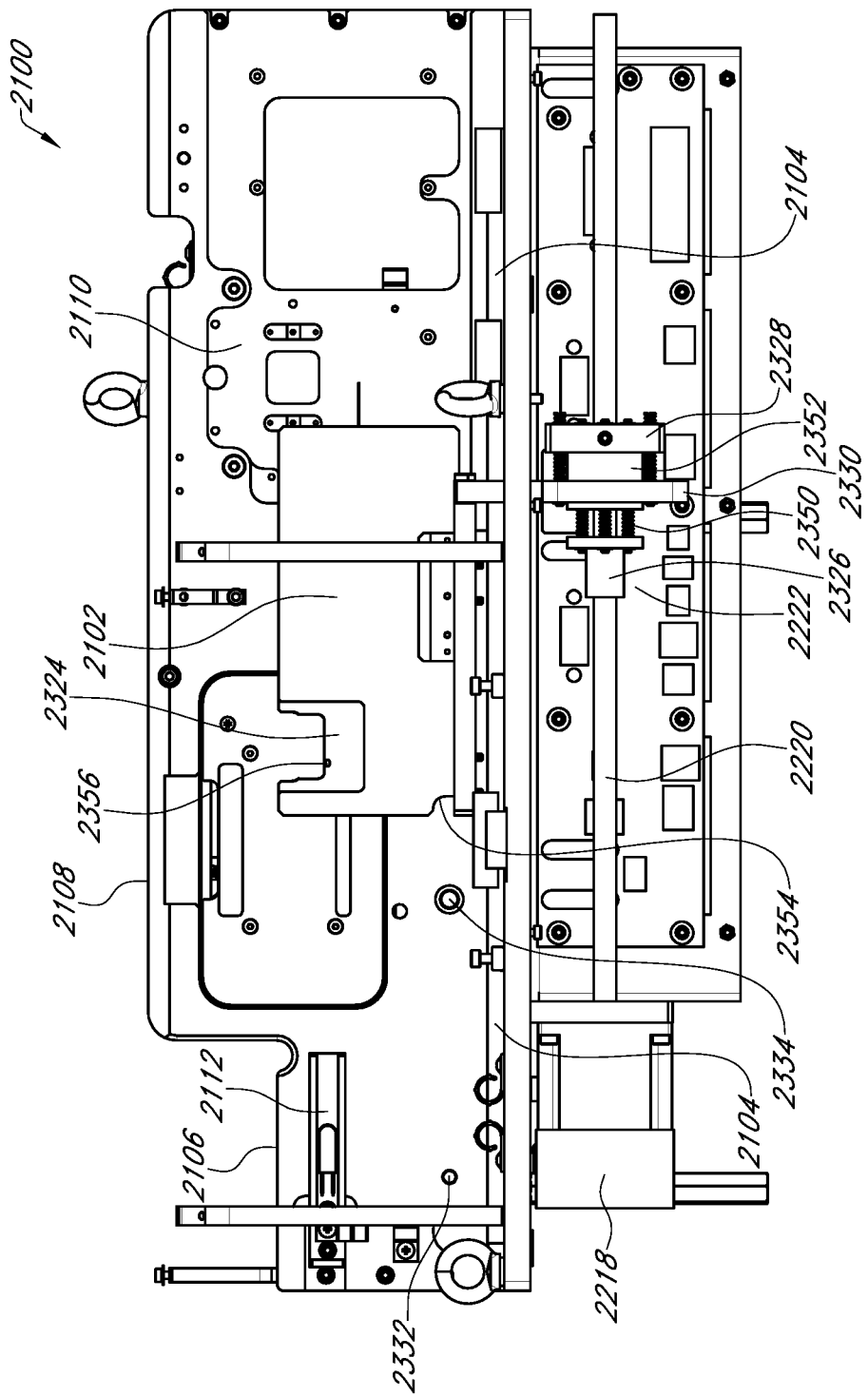
FIG. 19 and FIG. 20 include illustrations of example slide mechanism for use with the mechanical system.
Figure 20:
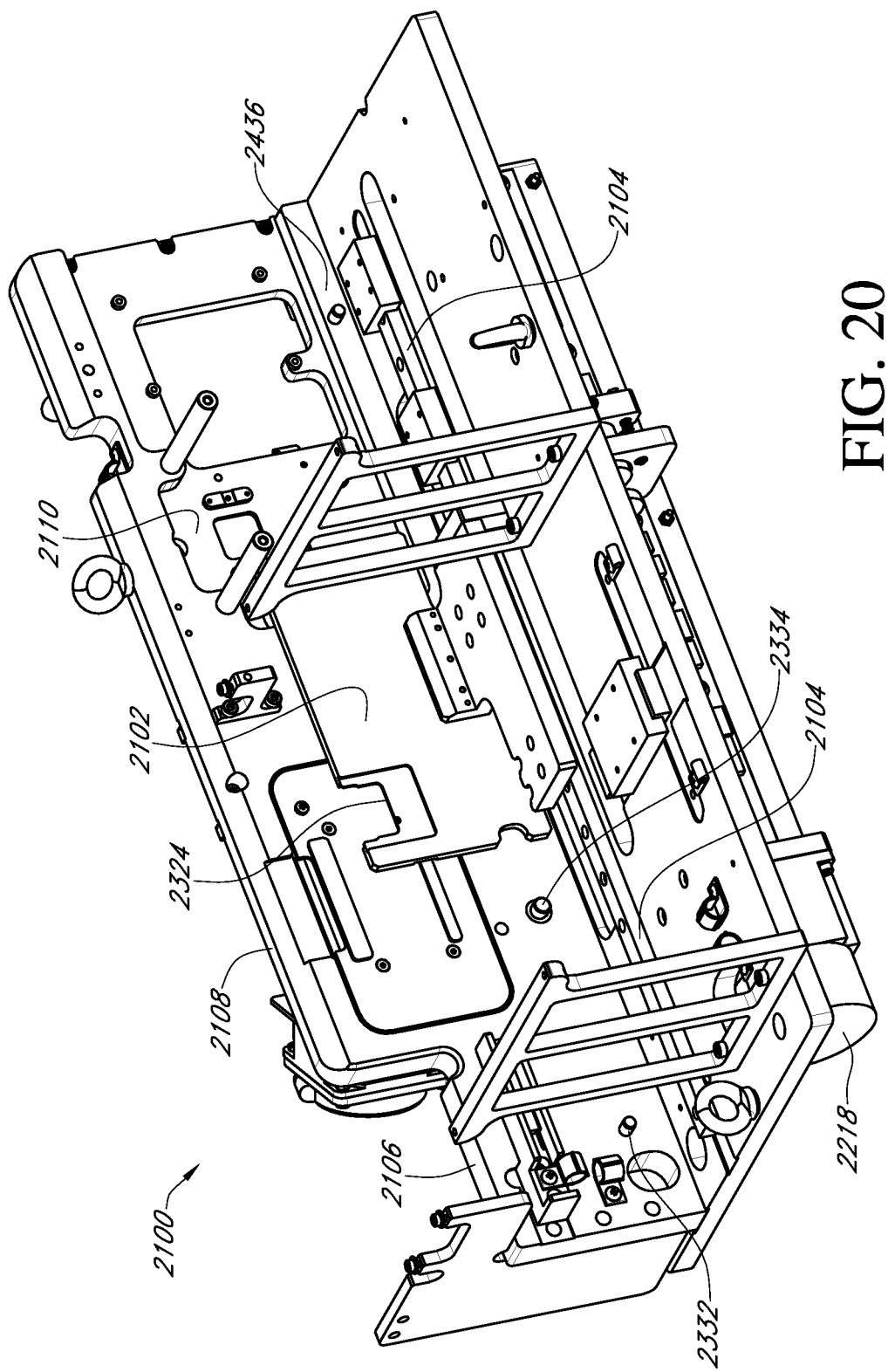

As illustrated in FIG. 19, the slide 2102 can be positioned at station 2106 in which a stop post 2332 engages the slide 2102 at feature 2354. Further, the slide 2102 can move forward from station 2106 to station 2108 at which a solenoid stop post 2334 can be engaged, and the slide moved backwards (left as illustrated) to engage the solenoid stop 2334 with the feature 2354. In addition, the slide 2102 can be moved along the rail 2104 to engage a forward stop 2436, illustrated in FIG. 20, aligning the slide and sensor receptacle 2324 with the station 2110. To return the slide 2102 back to station 2106, the solenoid stop post 2334 can be disengaged to permit the slide 2102 to pass.

When a sensor device is inserted into the receptacle 2324 at station 2106, a sensor 2112 can sense the presence of the sensor device in the receptacle 2324 through opening 2356. For example, the sensor device 2112 can be an optical sensor that optically detects the presence of the sensor device within the receptacle 2324 through the opening 2356.

The clutch 2222 can be used to provide both a backwards force (illustrated as toward the left) against stops 2324 or 2334 and a forward force (illustrated as toward the right) against the stop 2436. For example, the clutch system 2222 includes a nut 2326 to engage the screw 2220 of the screw drive mechanism 2218. The nut 2326 is engaged with a coupling 2328 having a central bore that allows the screw 2220 to pass through the coupling 2328. The coupling 2328 is attached to the nut 2326 using pin and spring system 2350. The pins are movably connected to the nut so that when the springs of the pin and spring system 2350 compress, the pins move through the nut 2326.

The coupling 2328 is also connected to a connector plate 2330 using pin and spring systems 2352. The pins of the pin and spring system 2352 can be configured to move through the connector plate 2330 when the springs of the pin and springs system 2352 are compressed. Alternatively or in addition, the pins of the pin and spring system 2352 can be configured to move through the coupling 2328.

The connector plate 2330 is coupled to the slide 2102 moving back and forth in response to a rotation of the screw 2220. When the slide 2102 is moved backwards (illustrated as left in FIG. 18) against the stop 2332 or 2334, the springs of the pin and spring system 2352 can compress, and the pins can move through either the connector plate 2330 or the coupling 2328. As such, rotation of the screw 2220 provides a known force backwards against the rods 2332 or 2334, providing for precise positioning of the sensor device within the receptacle 2324. In a further example, as the slide 2102 is moved forward to engage the stop 2436, the slide 2102 stops moving. Additional rotation of the screw 2220 moves the nut further forward (illustrated as right in FIG. 18). The springs of the pin and springs system 2350 compress, and the pins of the pin and spring system 2350 move through the nut 2326, providing a known force of the slide 2102 against the forward stop 2436. Such a force and positioning provides precise location of the sensor device receptacle 2324 and sensor device at station 2110.

Figure 21:
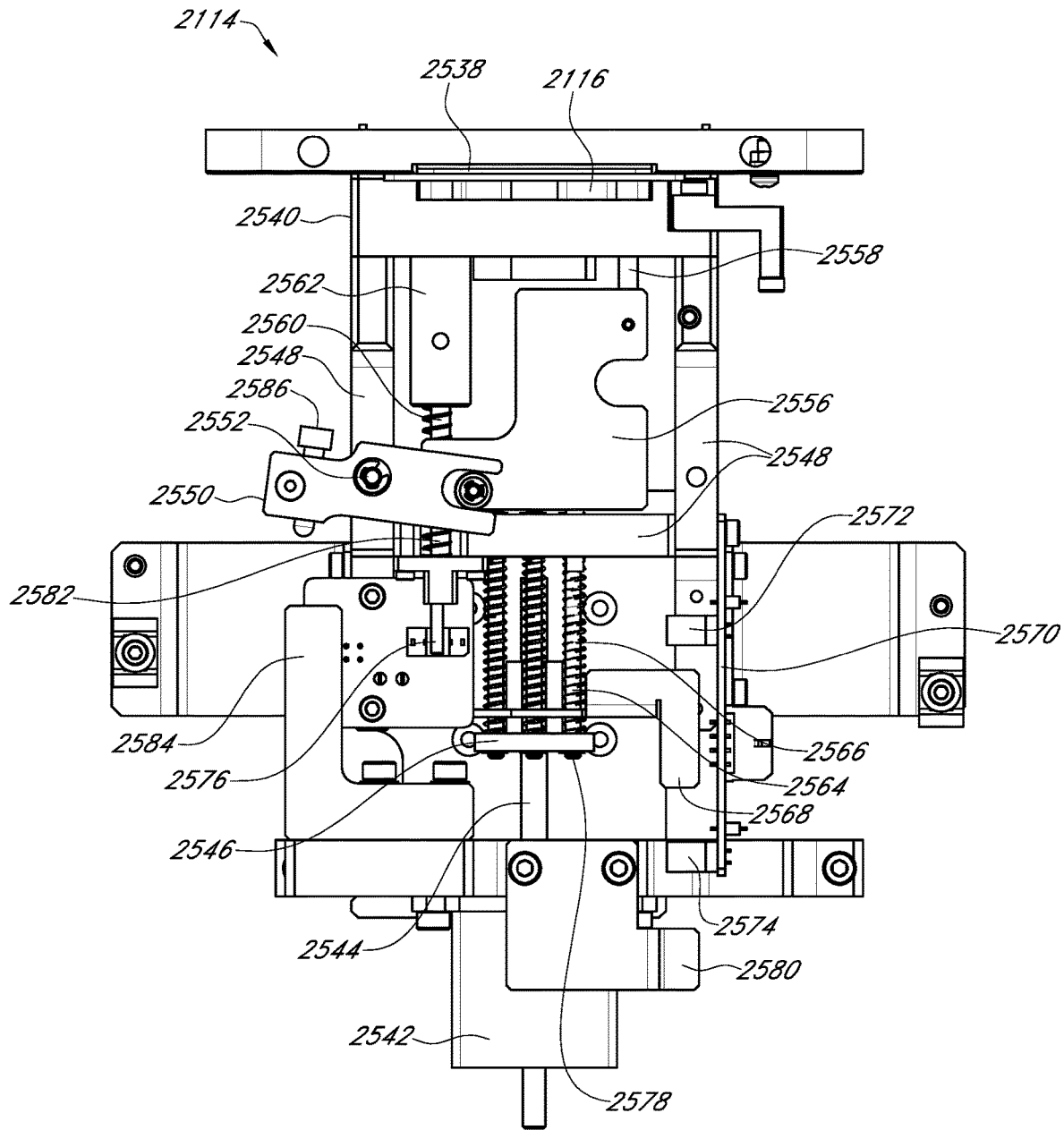
FIG. 21 includes an illustration of an example mechanical assembly to provide fluidic connection between the fluidic coupler and the sensor device.

FIG. 21 includes an illustration of an example mechanical assembly 2114 to provide a fluidic coupling between the sensor device and a fluidic coupler. When the slide is in position, a space 2538 is provided for the sensor device. Further, a space 2116 is provided for a fluidic coupler. When engaged by the mechanical assembly 2114, a fluidic coupler is pressed in fluid communication with the sensor device and with the manifold 2540. The drive mechanism 2542 utilizing, for example, a screw drive with a screw 2544, can move a frame 2548 of the mechanical assembly 2114 forward (illustrated as up in FIG. 21) and backwards (illustrated is down in FIG. 21) utilizing clutch system having a nut 2546 and coupled to the frame 2548 by pins 2564 and springs 2566. The pins 2564 can be movably coupled with the nut 2546 such that the heads 2578 of the pins 2564 are positioned against the nut 2546 until the manifold 2540 is pressed against a fluidic coupler. Additional movement of the nut 2546 forward causes the pins 2564 to move through the nut 2546, allowing the springs 2566 to compress.

The frame components 2548 can move together forward and back in response to the movement of the nut 2546. A lever 2550 is rotatably coupled to the frame 2548 at fastener 2552. When the assembly is in a rearward position, an adjustment screw 2586 attached to the lever 2550 engages a stop 2584, pivoting an opposite side of the lever 2550 rearward (downward as illustrated). As the nut 2546 moves forward, the adjustment screw 2586 gradually disengages from the stop 2584, and the opposite side of the lever 2550 is pivoted forward, for example, motivated by a spring 2582. The pivoting of the lever 2550 moves a guide plate 2556 forward relative to the frame 2548 that is also moving forward (upward as illustrated). The guide plate 2556 is connected to guide rods 2558 and 2560 that move forward with the guide plate 2556 to engage reference holes of a fluidic coupler. The guide rod 2560 can be further guided by a guide 2562 that engages a portion of the manifold 2540. As the guide rod 2560 moves forward, it can disengage from a sensor 2576, indicating that the guide rod 2560 is engaging the reference hole of the fluidic coupler.

When the manifold 2540 and the guide rods 2558 and 2560 engage the fluidic coupler, the nut 2546 can continue forward while the frame 2546 remains stationary. The pins 2564 can move through the nut 2546 and the springs 2566 compress, providing a known force against the fluidic coupler and against the sensor device in fluid communication with the fluidic coupler. Such force provides a desirable leak-free fluidic coupling between the sensor device and the fluidic coupler.

A circuit board 2570 including sensors 2572 and 2574 can be connected to the movable frame 2548 and can move with the frame 2548. A flag 2568 can be connected to the nut 2546. From the rearward position to a second position in which the manifold 2540 and frame 2548 connect with the fluidic coupler, the position of the flag 2568 remains constant relative to the position sensor 2572. Once the manifold 2540 is positioned against the fluidic coupler and a sensor device, the nut 2546 moves forward relative to the frame 2548. Thus, the flag 2568 moves forward towards the sensor 2572. When the flag 2568 is detected by the sensor 2572, the forward drive of the nut 2546 can be stopped. As such, a known compression of the springs 2566 is achieved, and a known force is applied against the frame 2548, manifold 2540, and fluidic coupler.

As the nut 2546 is moved rearward from the forward position, the flag 2568 disengages from the sensor 2572 until the pins 2564 at their head 2578 are secured against the nut 2546. As the nut 2546 continues to move backwards, the frame 2548 and manifold 2540 are drawn rearward along with the sensor circuit board 2570. The adjustable screw 2586 engages the stop 2584, withdrawing the guide rods 2558 and 2560 from the reference holes of the fluidic coupler. As the guide rods are withdrawn from the fluidic coupler, the reference rod 2560 engages the sensor 2576 indicating it has been withdrawal from the reference hole of the fluidic coupler. The sensor 2574 continues to move backwards with the sensor circuit board 2570 attached to the frame 2548 until the sensor 2574 engages a flag 2580 indicating that the nut 2546 is in the rearward most position. The fluidic coupler is disengaged from the mechanical assembly 2114 and can be removed. Further, the slide mechanism 2102 can move the sensor device to the next station 2110.

Figure 22:
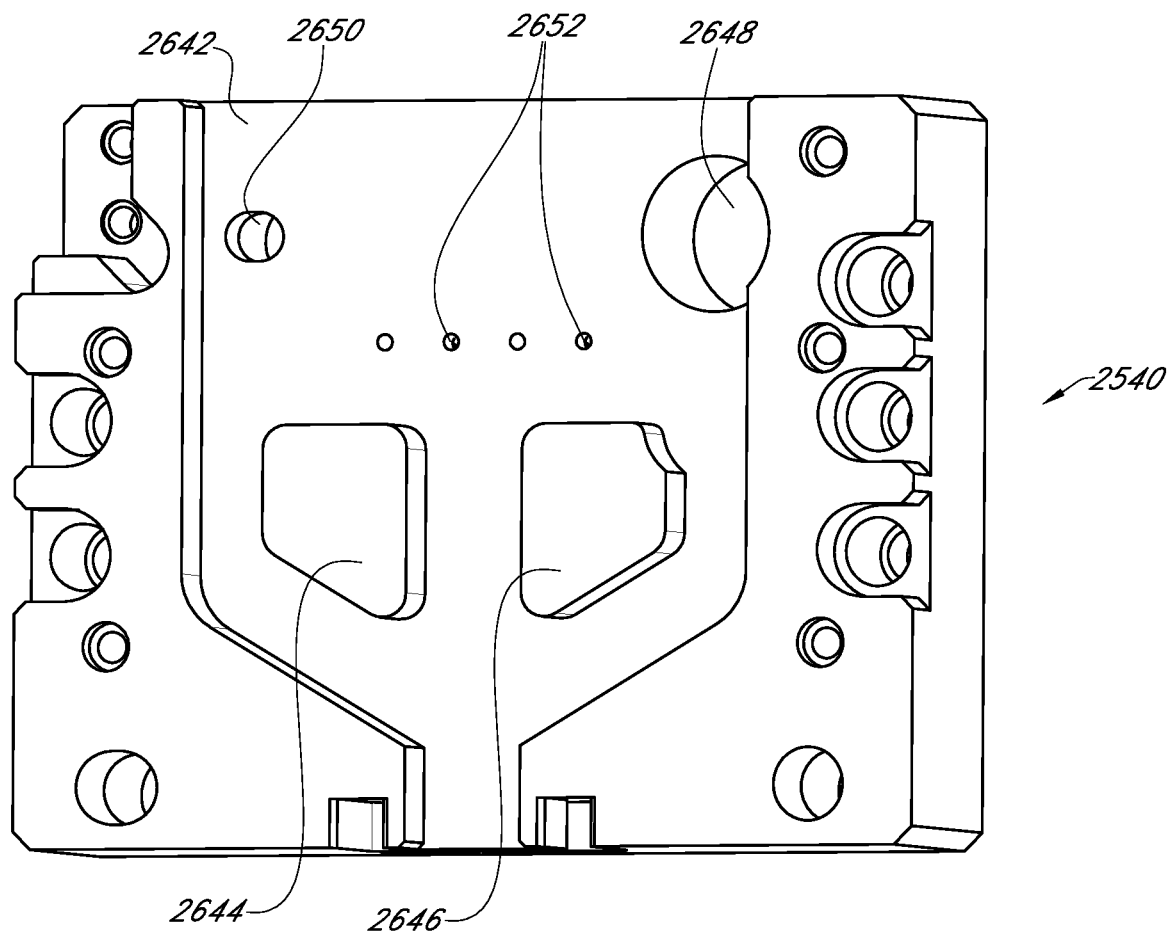
FIG. 22 and FIG. 23 include illustrations of example fluidic manifold.
Figure 23:
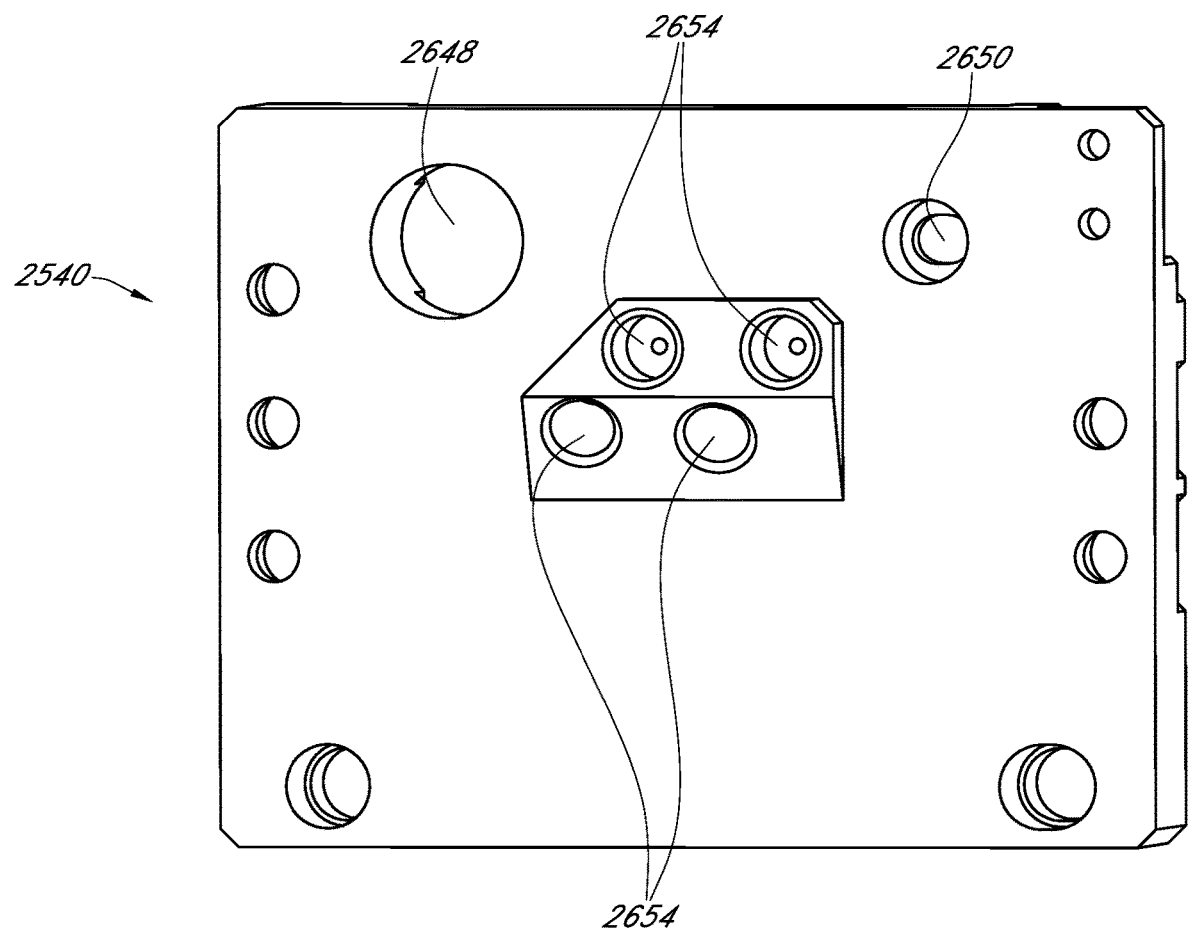

FIG. 22 and FIG. 23 include illustrations of an example manifold 2540 for use with the mechanical assembly 2114.

The manifold 2540 can include at a front surface a slot 2642 to receive the fluidic coupler. The slot 2642 along with rest structures 2644 and 2646 can set a vertical position of a fluidic coupler, such as the fluidic coupler 1600 illustrated in FIG. 16. The connector section 1612 of the fluidic coupler 1600 can extend over the manifold 2540 towards the rear surface of the manifold. The manifold 2540 can further include reference holes 2650 and 2648 that align with the reference holes 1610 of the fluidic coupler 1600. The reference hole 2650 can be sized to receive the guide rod 2558. The reference hole 2648 can be sized to receive the guide rod 2560 and optionally the guide 2562.

In particular, the manifold 2540 includes a set of fluid openings 2652 to engage the third ports 1818 of the fluidic coupler 1600 (illustrated in FIG. 14). The set of openings 2652 are in fluid communication with a set of ports 2654 disposed on a rearward surface of the fluid manifold 2540. Such ports 2654 can be connected to a vacuum to allow fluid to be drawn through the ports 2654, the openings 2652, the third set of ports 1818 of a fluidic coupler 1600, and the second set of ports 1606 of a fluidic coupler 1600. Optionally, an additional set of fluid openings and flow ports can be provided to connect with the fourth set of fluid ports 1820 of the fluidic coupler 1600.

Figure 24:
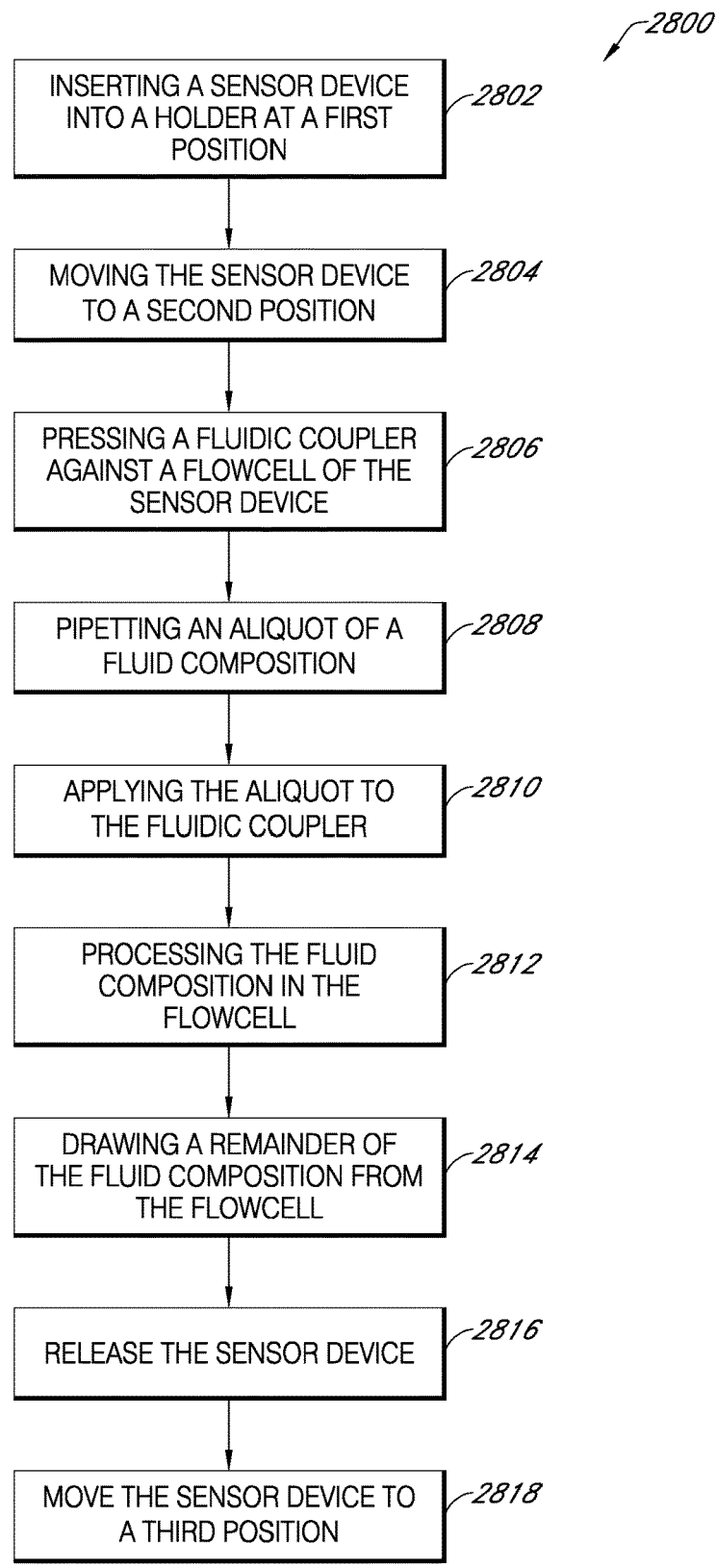
FIG. 24 includes a block flow diagram of an example method for interacting with a sensor device using the mechanical system.
Figure 25:
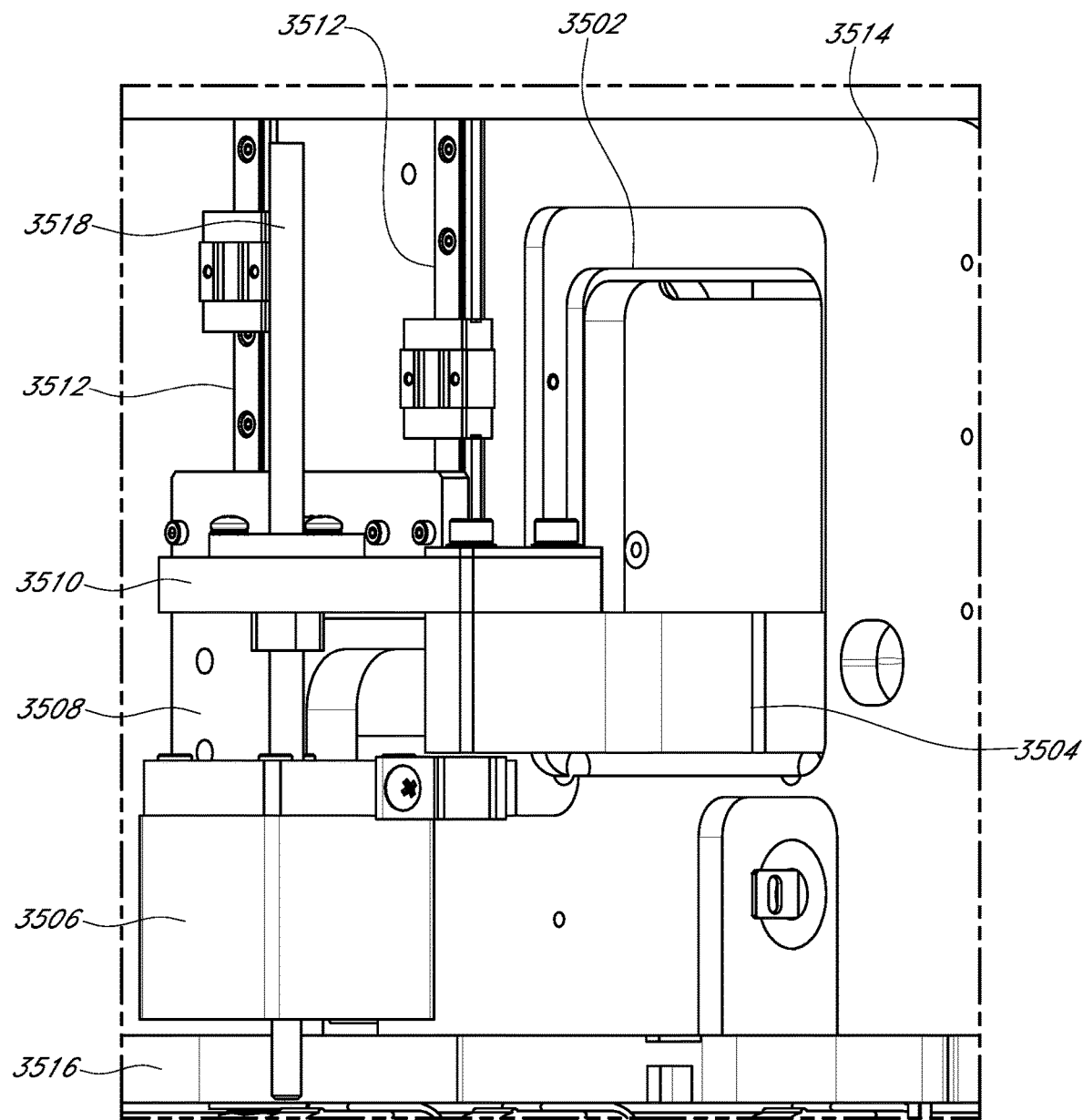
FIG. 25, FIG. 26, FIG. 27, and FIG. 28 include illustrations of an example loading device.

FIG. 24 includes a block flow diagram illustrating a method 2800 for fluidically engaging a sensor device. For example, as illustrated at block 2802, a sensor device can be inserted into a holder or receptacle of the slide when the slide is in a first position. Optionally, a detector can determine whether the sensor device is properly positioned within the holder or receptacle prior to allowing movement of the slide to a second position.

As illustrated at block 2804, the sensor device and slide can be moved to a second position. In an example system, the second position can represent a position in which a sample is loaded onto the sensor device. For example, a fluidic coupler can be pressed against a flow cell of the sensor device, as illustrated at block 2806. The fluidic coupler can include openings that allow fluid compositions to be pipetted into the openings and through ports of the fluidic coupler that are engaged with inlets of the flow cell of the sensor device.

For example, a pipette can draw an aliquot of a fluid composition, as illustrated at block 2808. The aliquot can be applied to the openings of the fluidic coupler, as illustrated at block 2810. The aliquot can pass through the opening of the fluidic coupler, through the first set of ports, and through the inlet of the sensor device and into the flow cells of the sensor device.

In an example, the fluid composition can be processed within the flow cell, as illustrated at block 2812. For example, a magnetic loading technique can be applied to load samples within wells of the sensor device.

As illustrated at block 2814, the remainder of the fluid composition can be drawn from the flow cells of the sensor device. For example, a vacuum attached to the manifold pressed against the fluidic coupler and in fluid communication with the outlets of the flow cells can draw the remainder of the fluid composition from the flow cells. The process of pipetting an aliquot of fluid composition, applying the aliquot, processing the fluid composition, and drawing the remainder of the fluid composition can be repeated, for example, to apply additional samples or wash the flow cell.

Once the process of loading is complete, the sensor device can be released from the mechanical assembly, as illustrated at block 2816. For example, the mechanical assembly can be drawn to a rearward position, releasing the sensor device and the fluidic coupler, and permitting the sensor device to move to a subsequent station.

The slide and sensor device can move to a third position, as illustrated at block 2818. For example, sensor device can be moved to a sequencing zone of the system. For resequencing, the sensor device can be moved to a loading position and the process steps 2810-2818 can be repeated.

Magnetic Loading

Templating can be performed using various methods. Example embodiments include "Systems and Methods for Preparing a Sequencing Device," US 2020/0072826A1, or "Methods and Compositions for Manipulating Nucleic Acids," US 2019/0255505A1, each of which is incorporated herein by reference.

Such methods of loading may be implemented in hardware having a horizontal or vertical configuration. For example, the hardware can hold a substrate on to which beads are being deposited horizontally. In another example, the hardware can hold the substrate vertically in which the plane of the substrate is approximately parallel to gravity. As used herein, vertical refers to an orientation in which a plane of a major surface of a substrate is closer to being parallel with gravity than perpendicular to gravity. In an example illustrated in FIG. 25, FIG. 26, FIG. 27, and FIG. 28, a magnetic loading system 3500 includes a plate 3502 and a magnet holder 3504 that guides magnets along the plate 3502. In the illustrated example, the plate 3502 is secured to a vertical structure 3514 that is secured to a horizontal structure 3516. The magnet holder 3504 can move magnets up and down along the plate 3502 to facilitate loading of beads supports, such as sequencing beads, into wells of a substrate disposed on opposite side of the plate 3502.

In a particular example, a drive mechanism 3506 can facilitate movement of the magnet holder 3504 up and down along the plate 3502. For example, the drive mechanism 3506 can rotate a threaded screw 3518 to drive a connector plate 3510 up and down along the screw 3518. The connector plate 3510 is connected to the magnet holder 3504. Optionally, the connector plate 3510 can be coupled with a guide plate 3508. The guide plate 3508 can slide along rails 3512, providing stability to the movement of the connector plate 3510 and the magnetic holder 3504.

Figure 26:
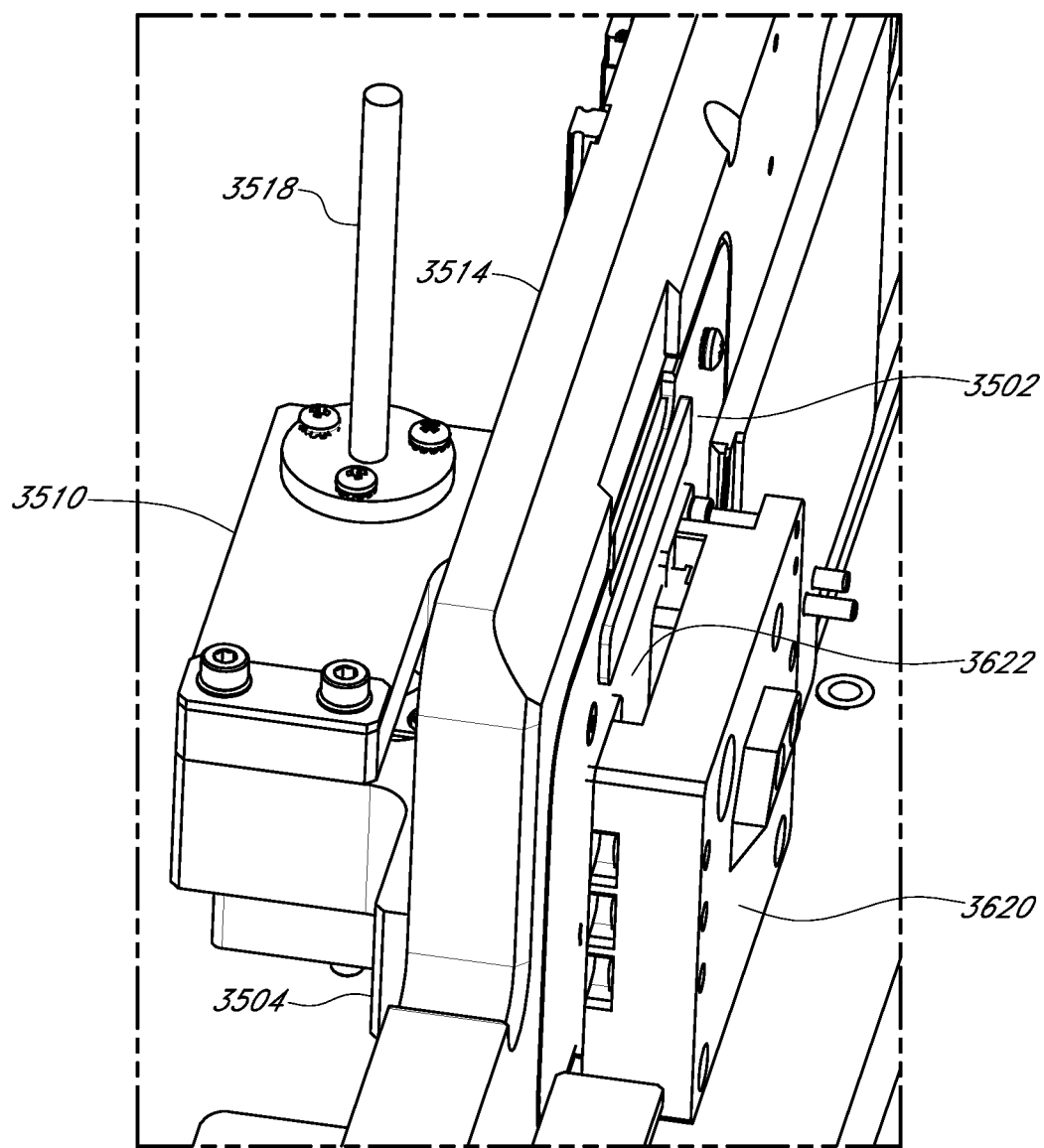

As illustrated in FIG. 26, a substrate holder 3620 (e.g., the manifold of FIG. 26 or FIG. 27) provides space 3622 for a substrate or sensor device, such as a microchip with a flow cell, to be inserted and held against the plate 3502. As the magnets attached to the holder 3504 moved up and down along the vertical surface of the plate 3502, bead supports attached to magnetic beads in solution are deposited into wells of the substrate. In an example, the substrate is a sequencing chip having a flow cell in which the solution is disposed.

Figure 27:
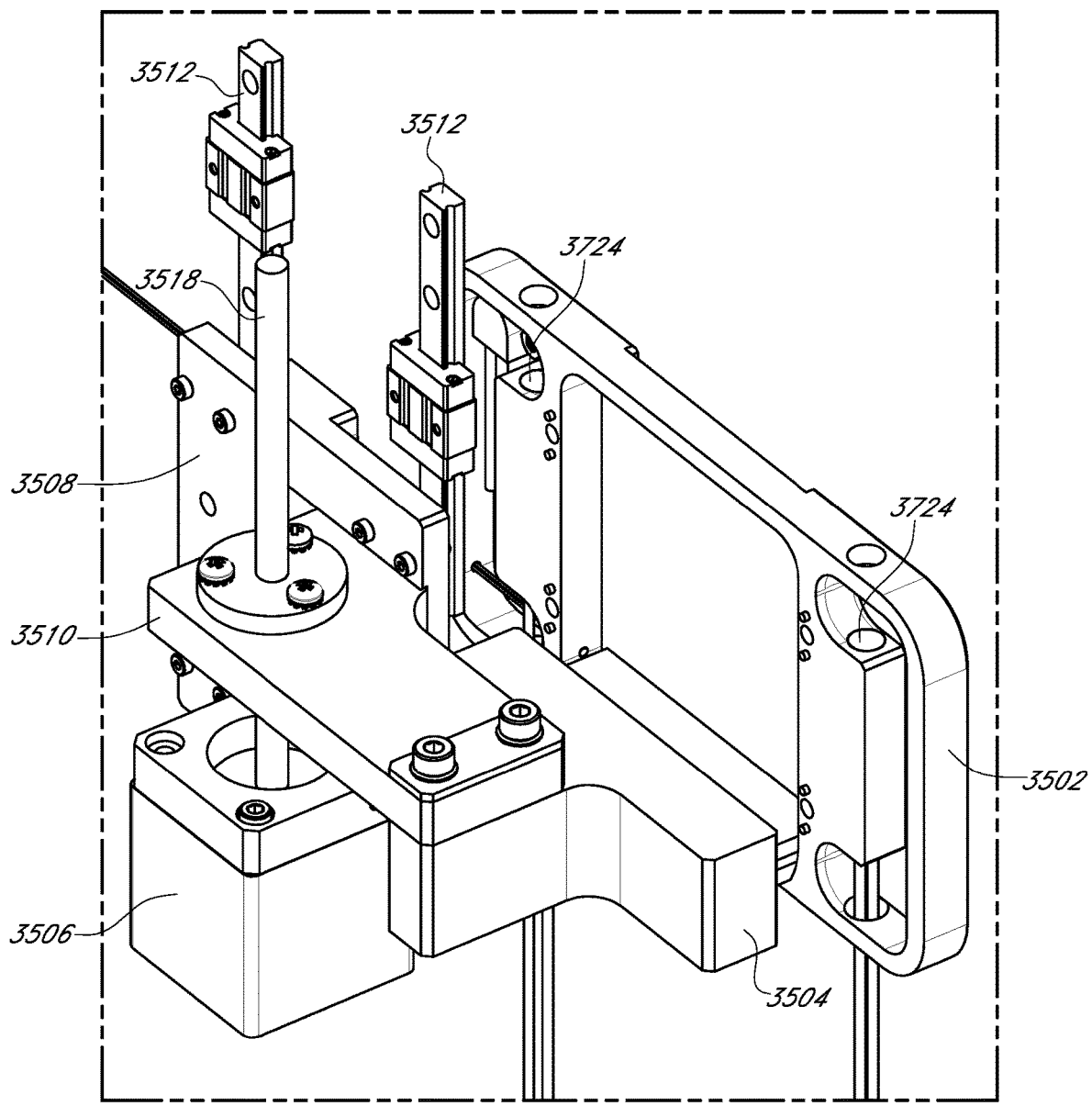

As illustrated in FIG. 27, the plate 3502 can optionally include recesses to receive heaters 3724. The heaters 3724 can be utilized to control the temperature of the plate 3502 and optionally the substrate positioned adjacent to the surface of the plate 3502. Alternatively, the heaters 3724 can be utilized to facilitate melt off of double-stranded nucleic acids or control a temperature for amplification.

Figure 28:
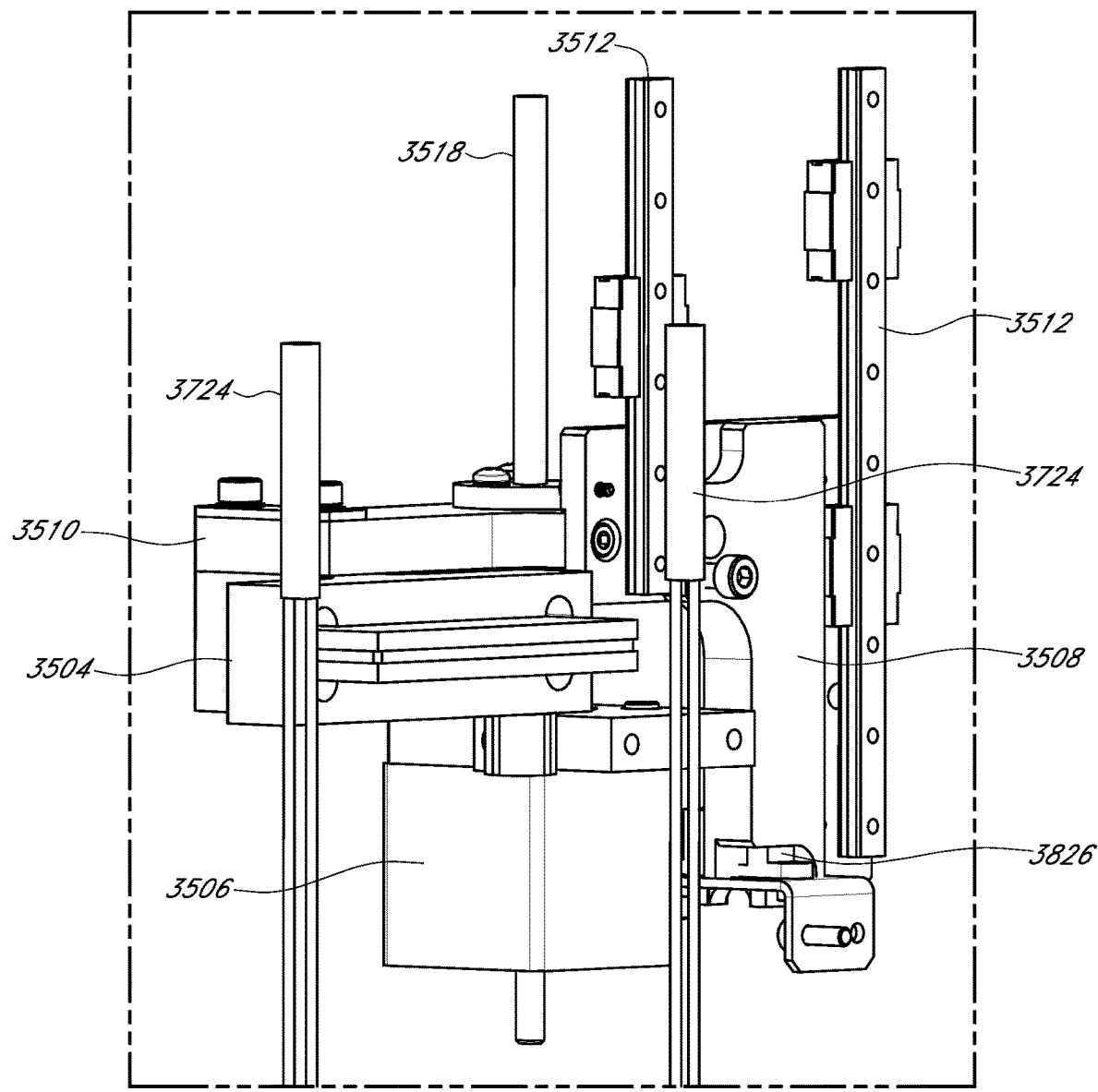

The magnetic holder 3504 can include one or more magnets. For example, as illustrated in FIG. 28, the magnetic holder 3504 can include a magnet 3828 and a magnet 3830. The magnets 3828 or 3830 can be separated by air. Alternatively, the magnets can be separated by a paramagnetic material or insulative material.

In an example, the magnets are configured such that different polls of the magnets are positioned against the plate 3502. For example, the magnet 3828 may be configured to have a north pole positioned adjacent the plate 3502, and the magnet 3830 can be configured to have a south pole adjacent to the plate 3502. Alternatively, the south pole of the magnet 3828 and the north pole of the magnet 3830 can be positioned adjacent to the plate 3502. In a further alternative, the same pole of each magnet can be positioned adjacent the plate 3502.

The system can further include a sensor 3826 that detects a position of the magnets, for example, a lower boundary. As illustrated in FIG. 28, the guide plate 3508 can interfere with an optical sensor 3826 when the magnets are in their lower position. Alternatively, other sensors can be used to determine the position of the plates and associated magnets.

Following loading beads into wells of a sensor device or microchip, polynucleotides on the sequencing beads can be amplified to form monoclonal populations of polynucleotide on the sequencing beads. The monoclonal populations of polynucleotides can be sequenced using, for example, ion-based sequencing techniques.

Figure 29:
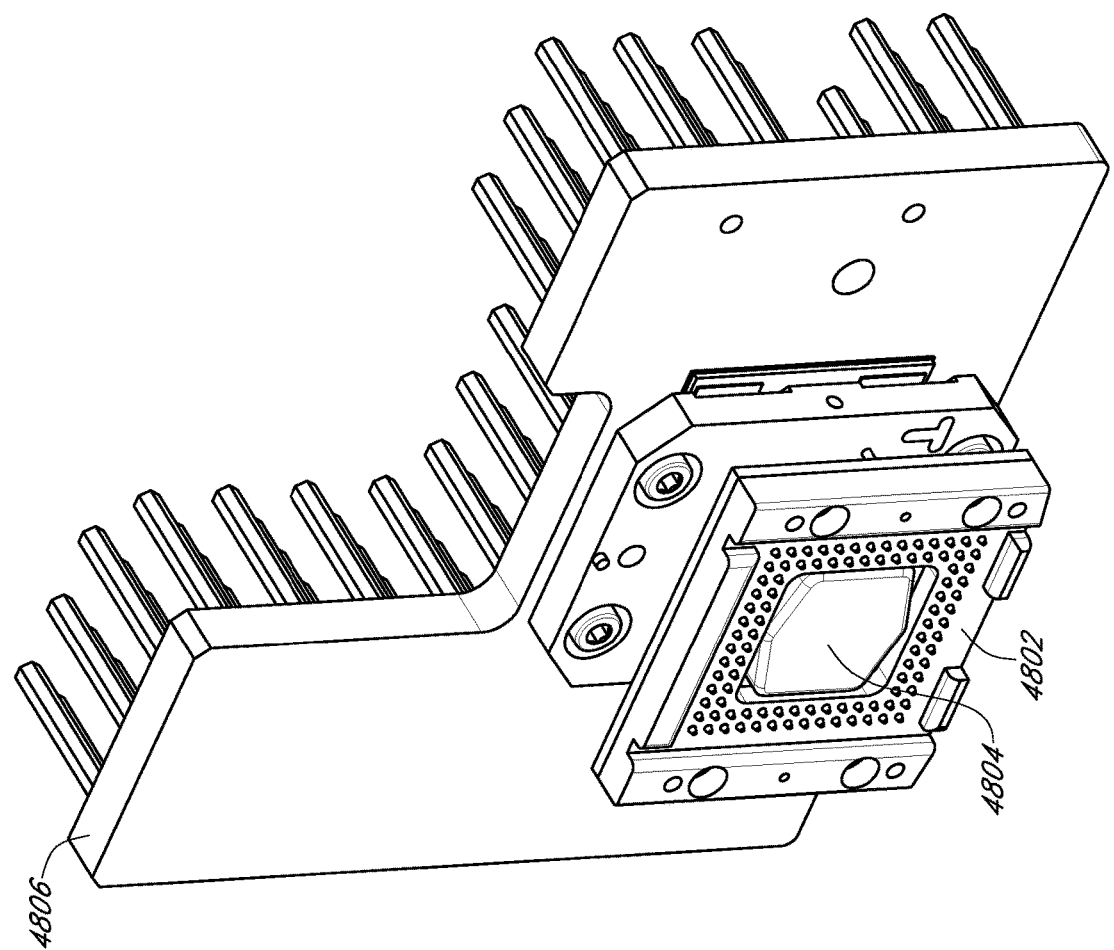
FIG. 29 includes an illustration of an example electronic interface.

FIG. 29 includes an illustration of an exemplary electronic interface 4802 for interfacing with the sensor device. For example, the electronic interface 4802 can include pins to interact with an electronic interface of the sensor device. Optionally, the interface 4802 can include a mechanism 4804 to disengage the sensor device from the electronic interface 4802. For example, when a fluidic manifold is pressed against the sensor device, mechanism 4804 can depress. Example fluidic manifolds include those of "FLUIDICS SYSTEM FOR SEQUENTIAL DELIVERY OF REAGENTS," U.S. Pat. No. 8,846,378 or "DEVICE, SYSTEM AND METHOD FOR FLUID DELIVERY FOR SEQUENCING," PCT Application No. PCT/US2020/035086, which are incorporated herein by reference. When the fluidic manifold is disconnected from the sensor device, the mechanism 4804 can push the sensor device away from the electronic interface 4802. Optionally, the system can further include mechanisms for controlling temperature, such as a heatsink 4806. The heatsink 4806 can include fins. Alternatively, the heatsink 4806 can be liquid cooled heatsink.

In particular, the fluidic system and the electronic interface are used to detect nucleotide incorporations during a sequencing-by-synthesis reaction. The data is collected and provided to a sequencing instrument server system.

Sequencer Software

In some embodiments, a nucleic acid sequencing instrument maybe interfaced with a server system for control of various components of the sequencing instrument and processing of data output from sequencing runs on the sequencing instrument. The server system software may include a web application, databases and analysis pipeline and support connections from a sequencing instrument (e.g., FIG. 6). The server system software may provide the following major functionalities and application program interfaces (APIs):

1. APIs for user authentication, reagent tracking, run information and run tracking/logging. Supported instruments may include the sequencing instrument and extraction instrument.
2. APIs for a LIMS (Laboratory Information Management System) for creation of samples, libraries, plan run and retrieve the run status of the plan.
3. Support for management of samples and run data.
4. Support for assay configuration and execution of the analysis pipeline for data analysis and reporting.
5. Interface to a software update server for software updates and maintenance.
6. Supports configuration to connect to an annotation and reporting system, such as Ion Reporter from Thermo Fisher Scientific, deployed in a cloud-based system or a local system, and establishes secure and authenticated connection with the cloud-based system to transfer mapped or unmapped BAM files.
7. Supports configuration to connect to a resource system in a cloud computing environment, such as the Thermo Fisher Cloud, and establishes secure and authenticated connection with the cloud resource system to download software and system contents and to send telemetry data.

Figure 30:
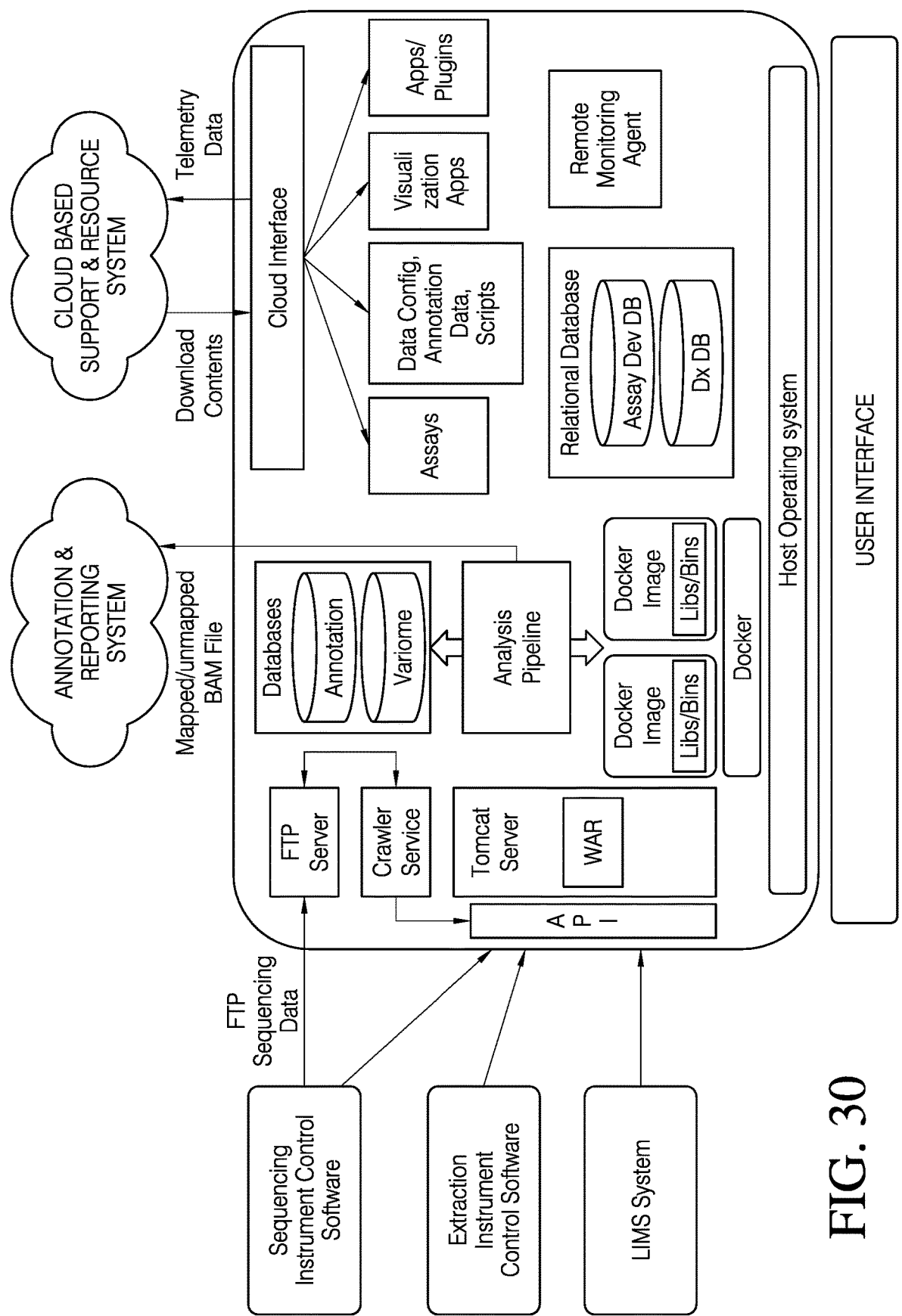
FIG. 30 includes a schematic diagram of server system components.

FIG. 30 shows a schematic diagram of the server system components. In some embodiments, the basic software architecture may comprise a web interface, remote monitoring agent, databases, APIs to the instruments, analysis pipeline, containerization of the analysis pipeline (using Docker, for example), connectivity to an annotations and reporting system (e.g. Ion Reporter from Thermo Fisher Scientific) and a cloud-based support and resource system (e.g. Thermo Fisher Cloud). The cloud-based support and resource system, or cloud-based resource system, may be implemented in a cloud computing and storage system. The cloud-based support and resource system stores content including assay definition files. A server of the cloud computing and storage system may download contents, such as assay definition files, to the local server system. The cloud-based support and resource system may receive telemetry data from the local server system. Server system, local server system and user's server system are used interchangeably herein.

In some embodiments, a user interface (UI) may be implemented via web application software. The UI may provide sample management pages. The sample management UI pages allow the user to enter sample information into the system. Sample information includes unique sample identifier (ID), sample name and sample preparation reagent tracking information. Validation logic is built into the sample management flow that locks the sample preparation step to the pre-defined assay workflow. The UI may provide assay management pages. Assay management UI pages allow the user to view assays, and create assays. The assays lock the workflows to pre-defined parameters for each step of the process. Validation logic may be built in to ensure the assay configuration. The UI may provide run plan and monitor pages. The run plan and monitor UI pages allow the user to plan for a run and monitor the run in progress. The UI may provide output data pages. The output data UI pages allow the user to view the analysis results along with quality control (QC) metric evaluation, log and audit trail of the results generated. The UI may provide configuration pages. The configuration UI pages allow users to view and configure the system.

In some embodiments, application programming interfaces (APIs) may be provided through a Java platform. For example, the Java platform may include a Tomcat server that may be used to build a Web ARchive (WAR) file for web-based applications.

Code modules for various steps of the analysis pipeline may be referred to as actors in the context of a Kepler workflow engine. For example, a code module for an analysis step may implemented by Java program binary code included in an actor jar. A Kepler workflow engine defines processing components of a workflow as "actors" and chains the steps for execution by a processor of the algorithm or analysis pipeline. (https://kepler-project.org). For example, a Kepler workflow engine may be used to configure the workflow of the analysis pipeline in FIG. 49.

The server system may include one or more databases. For example, the server system may include a relational database for storing sample data, run data and system/user configuration. The relational database may include two separate databases: assay development database and Dx database. The assay development database may store sample data, run data and system/user configuration for RUO, or assay development, mode of operation. The Dx database may store sample data, run data and system/user configuration for the IVD, or Dx, mode of operation.

The server system may include an annotations database, AnnotationDB, for storing annotation source data. For example, the annotations database may be implemented as NoSQL, or non-relational, database, e.g. a MongoDB database. Each annotation source may be stored as a JSON (JavaScript Object Notation) string with meta information indicating source name and version. Each annotation source may contain a list of annotations keyed to annotation IDs. The server system may include a variome database, VariomeDB, for storing variant information. For example, the variome database may be implemented as a NoSQL, or non-relational, database, e.g. a MongoDB database. The VariomeDB may store a collection of variant call results on a particular sample. For example, a JSON formatted record may contain meta information for identifying the sample.

For example, the AnnotationDB database may store one or more of the following annotation sources:
1. RefGene Model: hg19_refgene_63, version 63
2. RefGene Functional Canonical Transcripts Scores: hg19_refgeneScores_4, version 4
3. dbSNP: dbsnp_138, version 138
4. Canonical RefSeq Transcripts: hg19_refgene_63, version 63
5. 5000Exomes: hg_esp6500_1, version 1
6. ClinVar: clinvar_1, version 1
7. DGV: dgv_20130723, version 20130723
8. OMIM: omim_03022014, version 03022014

Other annotation sources may be included. Other versions of the above annotation sources may be included. The annotation source may provide public annotation information content or proprietary annotation information content.

For each call in Variome database, and each annotation source may be queried for annotations matching the variant and matching annotations may be stored as key-value pairs in Variome database with the variant. Annotated variants may be included in a results file, e.g. an annotated VCF file, for the user. VCF files are tab-separated text files used for storing gene sequence variants. In some embodiments, the annotation methods for use with the present teachings may include one or more features described in U.S. Pat. Appl. Publ. No. 2016/0026753, published Jan. 28, 2016, incorporated by reference herein in its entirety.

In some embodiments, the server system may include an analysis pipeline to process sequencing data generated during a sequencing run for an assay performed by a sequencing instrument. The sequencer transfers sequencing data files and experiment log files to the server system memory, for example in raw .dat files, already processed .dat files producing block wise 1.wells files, and thumbnail data. The analysis pipeline accesses the data files from memory and starts data analysis for the run.

In some embodiments, a Docker container and Docker images may be used for packaging the analysis pipeline and operating system specific binaries. The Docker is a tool used to create, deploy, and run applications by using containers. Containers enable an application with all the parts it needs, such as libraries and other dependencies, to be bundled as one package. This allows applications software to use the same Linux kernel as the host system. The Docker image files may be packaged with libraries and binaries needed by the analysis pipeline code. The Docker may be used to adapt an application or algorithm to a new or different version of an operating system (OS) to create a Docker image of the application that is compatible with the OS version.

In some embodiments, the server system may include a crawler service for data transfer from the sequencing instrument to the analysis pipeline. The crawler is an event-based service that may be developed using JAVA NIO watcher API (application programming interface). NIO (Non-blocking I/O) is a collection of Java programming language APIs that offer features for intensive input/output (I/O) operations. The crawler may monitor the FTP directory configured for the sequencing instrument to transfer run data from the sequencing instrument to the analysis pipeline.

Figure 31:
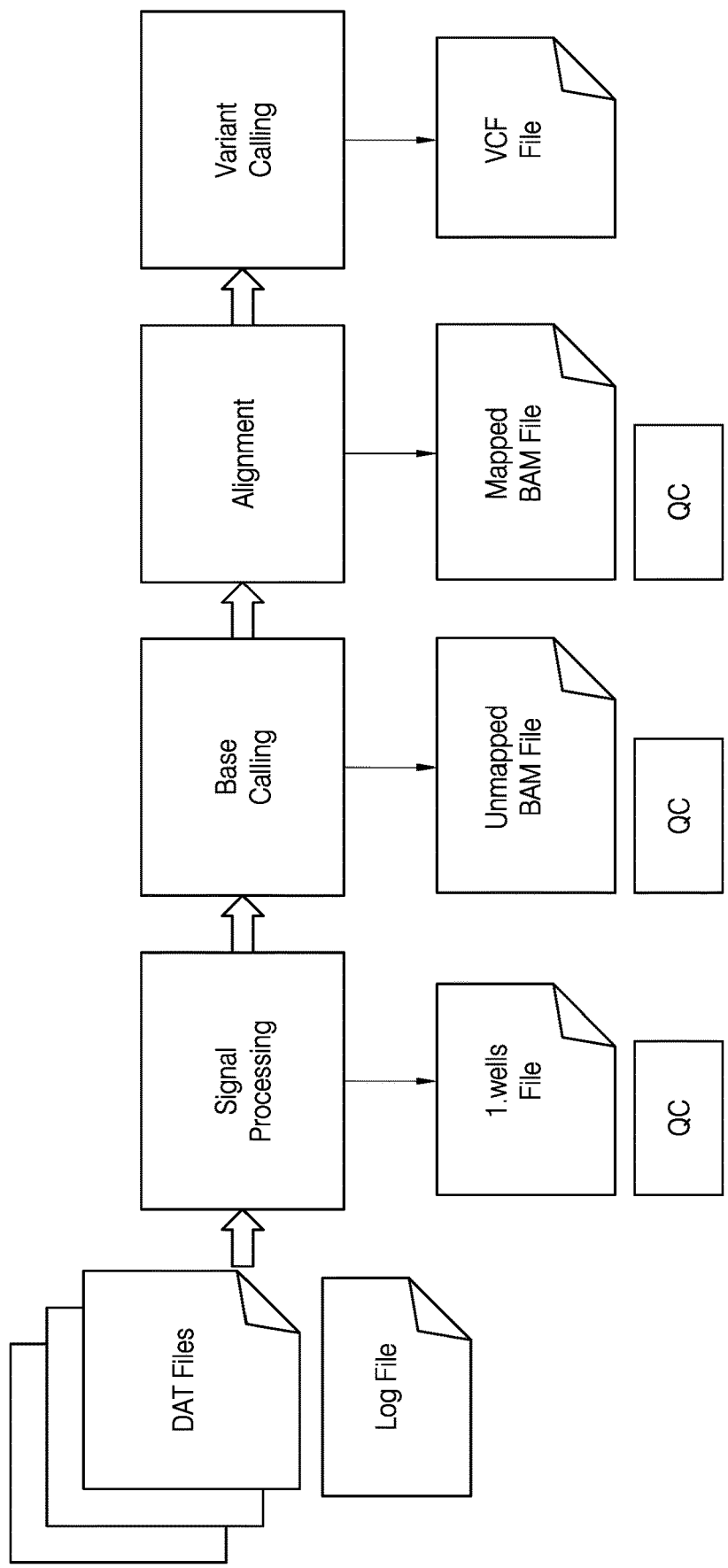
FIG. 31 includes a block diagram of the analysis pipeline.

FIG. 31 is a block diagram of the analysis pipeline, in accordance with an embodiment. The sequencing instrument generates raw data files (DAT, or .dat, files) during a sequencing run for an assay. Signal processing may be applied to raw data to generate incorporation signal measurement data for files, such as the 1.wells files, which are transferred to the server FTP location along with the log information of the run. The signal processing step may derive background signals corresponding to wells. The background signals may be subtracted from the measured signals for the corresponding wells. The remaining signals may be fit by an incorporation signal model to estimate the incorporation at each nucleotide flow for each well. The output from the above signal processing is a signal measurement per well and per flow, that may be stored in a file, such as a 1.wells file.

In some embodiments, the base calling step may perform phase estimations, normalization, and runs a solver algorithm to identify best partial sequence fit and make base calls. The base sequences for the sequence reads are stored in unmapped BAM files. The base calling step may generate total number of reads, total number of bases and average read length as QC measures to indicate the base call quality. The base calls may be made by analyzing any suitable signal characteristics (e.g., signal amplitude or intensity). The signal processing and base calling for use with the present teachings may include one or more features described in U.S. Pat. Appl. Publ. No. 2013/0090860 published Apr. 11, 2013, U.S. Pat. Appl. Publ. No. 2014/0051584 published Feb. 20, 2014, and U.S. Pat. Appl. Publ. No. 2012/0109598 published May 3, 2012, each incorporated by reference herein in its entirety.

Once the base sequence for the sequence read is determined, the sequence reads may be provided to the alignment step, for example, in an unmapped BAM file. The alignment step maps the sequence reads to a reference genome to determine aligned sequence reads and associated mapping quality parameters. The alignment step may generate a percent of mappable reads as QC measure to indicate alignment quality. The alignment results may be stored in a mapped BAM file. Methods for aligning sequence reads for use with the present teachings may include one or more features described in U.S. Pat. Appl. Publ. No. 2012/0197623, published Aug. 2, 2012, incorporated by reference herein in its entirety.

The BAM file format structure is described in "Sequence Alignment/Map Format Specification," Sep. 12, 2014 (https://github.com/samtools/hts-specs). As described herein, a "BAM file" refers to a file compatible with the BAM format. As described herein, an "unmapped" BAM file refers to a BAM file that does not contain aligned sequence read information and mapping quality parameters and a "mapped" BAM file refers to a BAM file that contains aligned sequence read information and mapping quality parameters.

In some embodiments the variant calling step may include detecting single-nucleotide polymorphisms (SNPs), insertions and deletions (InDels), multi-nucleotide polymorphisms (MNPs) and complex block substitution events. In various embodiments, a variant caller can be configured to communicate variants called for a sample genome as a *.vcf, *.gff, or *.hdf data file. The called variant information can be communicated using any file format as long as the called variant information can be parsed or extracted for analysis. The variant detection methods for use with the present teachings may include one or more features described in U.S. Pat. Appl. Publ. No. 2013/0345066, published Dec. 26, 2013, U.S. Pat. Appl. Publ. No. 2014/0296080, published Oct. 2, 2014, and U.S. Pat. Appl. Publ. No. 2014/0052381, published Feb. 20, 2014, and U.S. Pat. No. 9,953,130 issued Apr. 24, 2018, each of which is incorporated by reference herein in its entirety. In some embodiments, the variant calling step may be applied to molecular tagged nucleic acid sequence data. Variant detection methods for molecular tagged nucleic acid sequence data may include one or more features described in U.S. Pat. Appl. Publ. No. 2018/0336316, published Nov. 22, 2018, incorporated by reference herein in its entirety.

In some embodiments, the analysis pipeline may include a fusion analysis pipeline for fusion detection. Fusion detection methods may include one or more features described in U.S. Pat. Appl. Publ. No. 2016/0019340, published Jan. 21, 2016, incorporated by reference herein in its entirety. In some embodiments, the fusion analysis pipeline may be applied to molecular tagged nucleic acid sequence data. Fusion detection methods for molecular tagged nucleic acid sequence data may include one or more features described in U.S. Pat. Appl. Publ. No. 2019/0087539, published Mar. 21, 2019, incorporated by reference herein in its entirety.

In some embodiments, the analysis pipeline may include a copy number variants analysis pipeline for detection of copy number variations. Methods for detection of copy number variation may include one or more features described in U.S. Pat. Appl. Publ. No. 2014/0256571, published Sep. 11, 2014, U.S. Pat. Appl. Publ. No. 2012/0046877, published Feb. 23, 2012, and U.S. Pat. Appl. Publ. No. US2016/0103957, published Apr. 14, 2016, each of which is incorporated by reference herein in its entirety.

In some embodiments, the server system software may support an encapsulated assay configuration that includes assay name, assay type, panel, hotspot file if any, reference name, control names if any, quality control QC thresholds, assay description if any, data analysis parameters and values, instrument run script names and other configurations that define the assay. The entire set of the information is called an assay definition. The assay configuration content and corresponding workflows may be delivered to the user as modular software components in an assay definition file (ADF). The server system software may import an assay definition file that contains the assay configuration. The import process may be initiated by zip file import which includes an encrypted Debian file and triggers an installation process. The user interface may provide a page for the user to select an ADF for import. An application store in the cloud-based support and resource system may store ADFs supporting various assays, panels, and workflows available for selection by the user for download to the user's local server system.

An assay definition file (ADF) is an encapsulated file that defines configurations for the molecular test or assay, including assay name, technology platform configuration (for example, next generation sequencing (NGS), chip type, chemistry type), workflow steps (sample prep, instrument scripts, analytics, reporting), analysis algorithms, regulatory labels (for example, research use only (RUO), in vitro diagnostics (IVD), Central Europe in vitro diagnostics (CE-IVD, internal use only (IUO), etc.), targeted markers (panel), reference genome version, consumables, controls, QC thresholds, reporting genes and variants. The ADFs provide a modular approach to building assay capabilities for the local sequencing instrument. The assay software may be provided by the ADF separately from the platform software of the sequencing instrument.

The advantages of using the ADF for assay configuration include the following:
Encapsulation of the assay workflow and analysis
Single click for installation
No revalidation required after software update for assay configuration because of the modular structure of the software by the Docker implementation allowing separation from the platform software
Multi-tiered encryption for secure delivery
Streamlined support of assay configurations for original equipment manufacturers (OEM)
Streamlined customization of reporting
Support of regional regulatory requirements
Plug-n-play format supports technology agnostic workflows
Enables rapid expansion of molecular test menu and assay adoption by laboratories In some embodiments, the assay definition file (ADF) may include software code modules for one or more of the following steps 1) library preparation; 2) templating; 3) sequencing; 4) analysis; 5) variant interpretation; and 6) report generation. For the workflow steps of library preparation and templating, the ADF may include scripts for preparing libraries, templating, and enrichment of templated beads. For the workflow steps of sequencing and analysis the ADF may include Docker image packages of algorithm binary code and parameters for the analysis pipeline described with respect to FIG. 50. For the workflow step of variant interpretation, the ADF may include a list of annotation sources that may be used for analyzing and annotating variants. For the workflow step of report generation, the ADF may include report templates and image files for use when a generating a report.

The ADF may include for the instrument scripts for control of workflow steps on the sequencing instrument. For example, scripts may include parameters controlling the amount of pipetting and robotic control. The instrument scripts may be customized for the particular assay.

For example, for the sequencing and analysis steps, the ADF may include a Docker image of the end to end analysis pipeline. The Docker image may include OS specific libraries and binaries for the algorithms each step of analysis pipeline. The algorithm binaries may include steps of the analysis pipeline including signal processing, base calling, alignment, and variant calling, such as those described with respect to FIG. 50. In another example, the ADF Debian file may package certain code modules for a particular assay, such as code modules for signal processing, base calling and RNACounts.

The ADF may include scripts for configuration of reagent kits. These scripts support calculation of the consumables needed for a sequencing run. The configurations scripts included in the ADF may include one or more of the following:
Barcode set and chip
Library kit and consumables, including capability to associate sample control configuration, (e.g. sample inline control) and its QC parameters
Templating kit and consumables, including capability to associate internal controls and QC parameters
Sequencing kit, including capability to associate internal controls and QC parameters The ADF may include one or more reference genome files. Examples of reference genomes include hg19 and GRCH38. The reference genome file may be packaged in the main ADF with the workflow information. Alternatively, the reference genome file may be packaged in a separate ADF that is supplementary to the main ADF.

The ADF may include code modules for workflows of fusion panels and fusion target region panels. The ADF may include fusion target region reference files and hotspot files for analysis.

The ADF may include assay parameters at various points of the workflow that may be configured by the user. The configurable parameters may be displayed in the user interface for adjustment by the user. New parameters may be added at any actor level. The configurable parameters may be passed to the analysis pipeline. Input formats for the configurable assay parameters may include one or more single string text, Boolean, multiline text, floating point, radio buttons, drop downs, and file uploads. For example, the file uploads may use file formats such as .properties and .json.

The ADF may include QC parameters used for quality control and assay performance thresholds at various points in the workflow. For example, types of QC parameters include run QC parameters, sample QC parameters, internal control QC parameters and assay specific QC parameters. A QC parameter may be defined by one or more of a data type (e.g. integer, floating point), lower bound, upper bound and default value.

The ADF may include specified data tab columns for results presentation that are selected from the database for a given assay. The selected data tab columns support configuration of the user interface display of results and the columns to be included in the PDF reports for the assay. The ADF may include image files for results presentation for a given assay. The ADF may include support for multiple languages for the PDF reports. The ADF may include a download file list for any files to be generated by the analysis pipeline for a given assay. The file list for the sample or run may be displayed at the user interface. The ADF may include a gene list. The gene list may be used to display the known list of genes for a given cancer type at the user interface and in a PDF report.

The ADF may include a set of plugins to be used for a given assay. The ADF may specify a set of plugins and their versions. If the ADF does not specify a version of a plugin, the latest version of the plugin installed on the server system may be used for the given assay.

The ADF may include a new workflow template to support custom assay creation. The new workflow template may include a set of assay chevron steps. Parameters for the steps may be displayed.

The ADF may include a list of annotation sources and sets to support the configuration of new annotation sets. The ADF may include filter chains to be applied to variants detected by the analysis pipeline of a given assay. The ADF may include rulesets for annotation of variants.

The ADFs can be configured to support a number of different types of assays. Examples include, but are not limited to, oncology related assays (e.g., Oncomine assays from Thermo Fisher Scientific), immuno-oncology related assays (e.g., T-cell receptor (TCR), microsatellite instability (MSI) and tumor mutation load (TML)), infectious diseases related assays (e.g. microbiome), reproductive health related assays and exome related assays. The ADF can also be configured for a custom assay.

Figure 32:
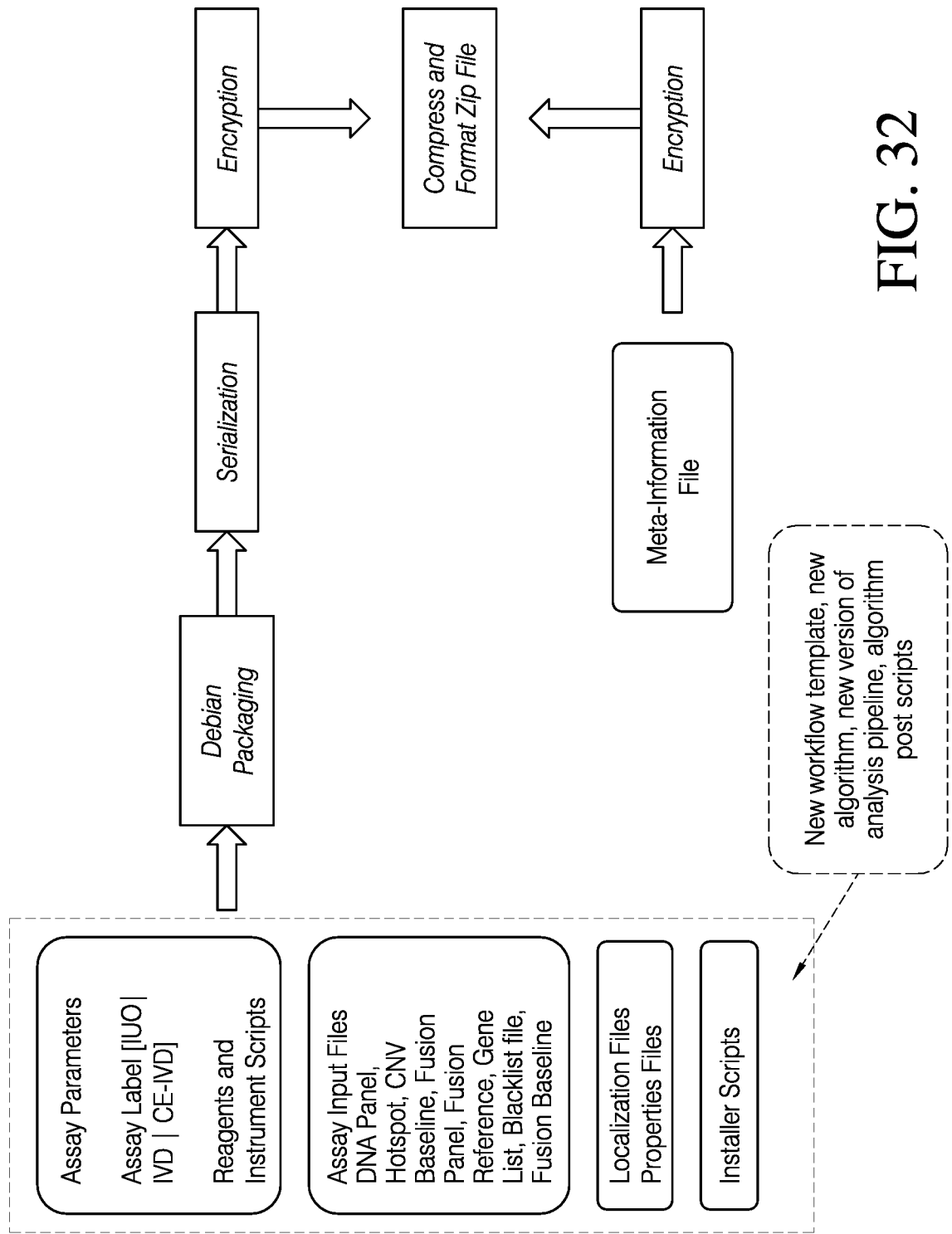
FIG. 32 includes a schematic diagram of generating an assay definition file.

FIG. 32 is a schematic diagram of generating an assay definition file, in accordance with an embodiment. The assay definition may be generated by build.sh, debscripts and makedeb.sh that initiate file copying and database population of assay information to form a Debian file. The assay definition content may include assay parameters, BED files (Browser Extensible Data file—BED file—defines chromosome positions or regions), panel files, gene lists, hotspot files (a BED or a VCF file that defines regions in the gene that typically contain variants), and seed data containing allowable reagents. The assay definition content may contain localized versions of an assay name, description and report messages that support assay information display in different languages. The assay definition file may support the packaging of a new analysis pipeline. The ADF may include an optional post processing script which may be executed for variant calling, fusion calling and CNV calling based on the type of assay. The ADF may include an optional Docker container image of updates to the binaries for a specific analysis pipeline. The Docker container image may be packaged with the ADF to ensure that platform changes such as operating system or third-party library do not impact the results of the assays or functioning of the system.

The Debian file may be serialized to prevent unauthorized modifications. The serialized assay definition may be further encrypted using Advanced Encryption Standard (AES), a symmetric-key algorithm. A text file containing assay meta-information may also be encrypted using AES and the same encryption key. The encrypted assay definition file, together with the encrypted meta-information file may be compressed into zip format. Other encryption formats may also be applied to the serialized assay definition information. For example, the meta-information may include one or more of the following:
Analysis pipeline version,
Reference genome path for the reference genome file location,
Assay unique name—the assay's internal name for checking the unique occurrence in the system,
Docker image name—to be used for launching analysis and installing assay dependent file references,
Any dependency package names needed for analysis pipeline launch.

Figure 33:
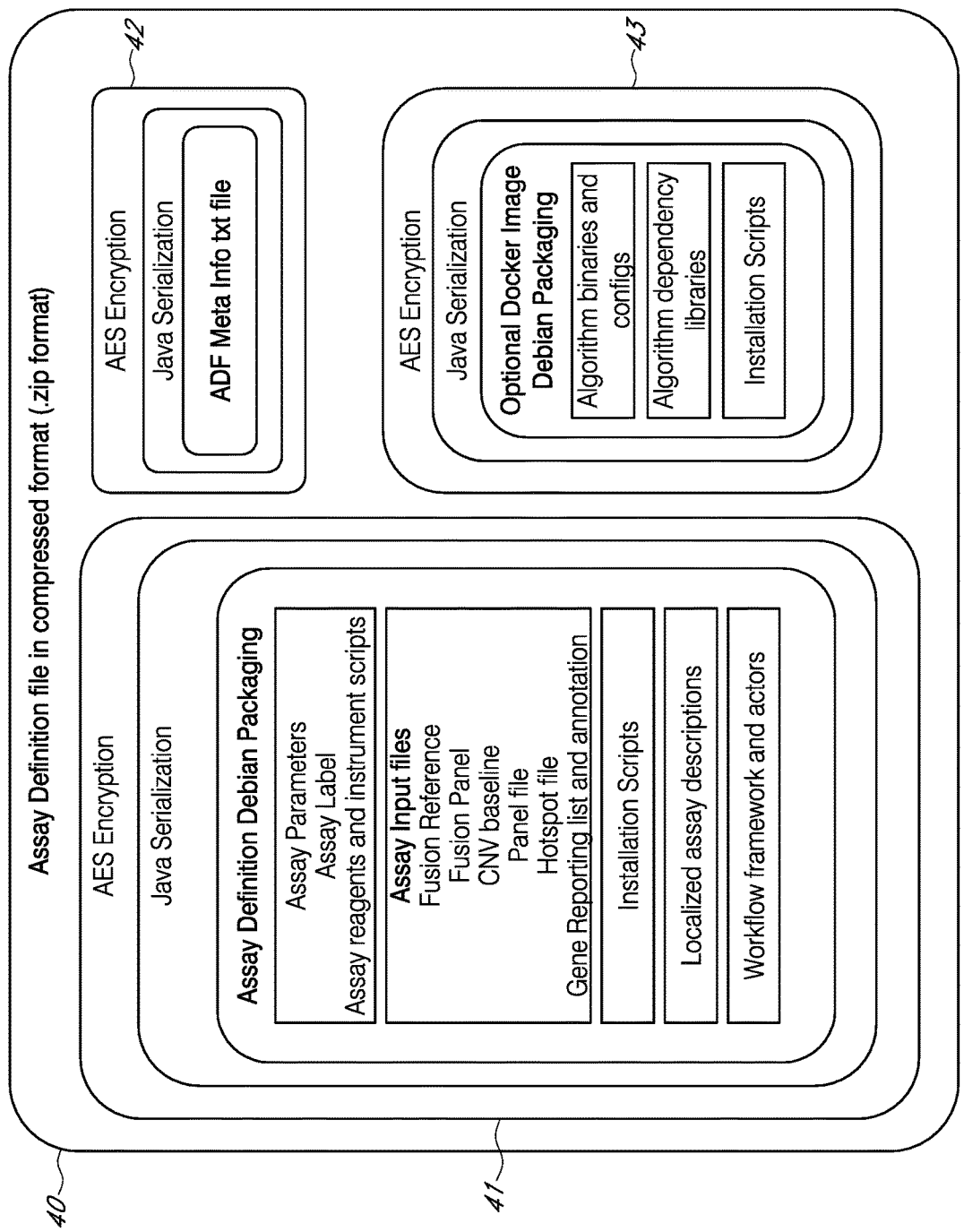
FIG. 33 includes a schematic diagram of an example of the assay definition file packaging.

FIG. 33 is a schematic diagram of an example of the assay definition file packaging. The compressed assay definition file in zipped format 40 may include the serialized and encrypted assay definition Debian packaging 41, the serialized and encrypted meta-information text file 42, and serialized and encrypted optional Docker image Debian packaging 43. The server system may decrypt both the meta-information text file 42 and the assay definition serialized file 41 before installing the assay definition Debian file.

The server system and modular software components may be configured to control multiple functional modes, including an RUO, or AD, mode and an IVD, or Dx, mode. Referring to FIG. 1, the Tomcat Server may be configured to include a Web ARchive (WAR) file for the RUO mode and a WAR file for the IVD mode. The server system may be configured to include a RUO variome database for the variants detected by RUO assays and an IVD variome database for the variants detected by IVD assays. The server system may be configured to include separate analysis pipelines and associated Kepler workflow engines for the RUO mode and the IVD mode. The RUO Docker image files for the RUO assays may be configured as separate files from the IVD Docker image files for the IVD assays. The relational databases may be configured to have separate databases: an assay development (AD) database for the RUO mode and a Dx database for the IVD mode. A server system that initially supports only a RUO mode may be configured to support RUO and IVD modes by a software update.

ADFs may be generated separately for RUO mode assays and IVD mode assays. The RUO mode ADFs may include assay definitions for assays used in research. The RUO mode ADFs may be developed by a third party. The IVD mode ADFs include assay definitions for assays compliant with regional regulatory requirements for diagnostic use.

Assays

The automated sequencing instrument can be adapted for use with a variety of targeted assays. Example, targeted assays can utilize chemistries, such as Ion Ampliseq, Ion Ampliseq HD, among other chemistries. For example, the automated sequencing instrument can be adapted for use with assays such as RNA-seq, Diff-Seq, or S1-seq, among other library preparation assays. Other example assays include Oncomine Cancer Assays, e.g., OCAv3, Oncomine Focus Assays, or an Oncomine TCR Beta-LR assay, among others.

The assays can be used with nucleic acids sourced from swabs, blood, FFPE tissue samples, cfDNA, among other sources. The nucleic acids can be in the form of DNA or RNA, optionally converted to CDNA.

The assays can have a number of primer pairs, for example, in a range of 10 to 24000. In an example, the number of primer pairs can be in a range of 100 to 1000, such as a range of 100 to 500 or a range of 150 to 300. In another example, the number of primer pairs is in a range of 300 to 5000, such as a range of 400 to 4000.

The assays can produce libraries having an average amplicon size in a range of 50 to 500, such as a range of 50 to 200 or a range of 75 to 125. In another example, the amplicon size can be in a range of 200 to 500, such as 200 to 400 or 200 to 300.

The assays can be performed in a single pool or can utilize multiple pools. For example, an assay can use a single DNA pool. In another example, an assay utilizes two DNA pools. In a further example, an assay utilizes two RNA pools. In a particular example, an assay utilizes two DNA pools and two RNA pools.

Figure 34:
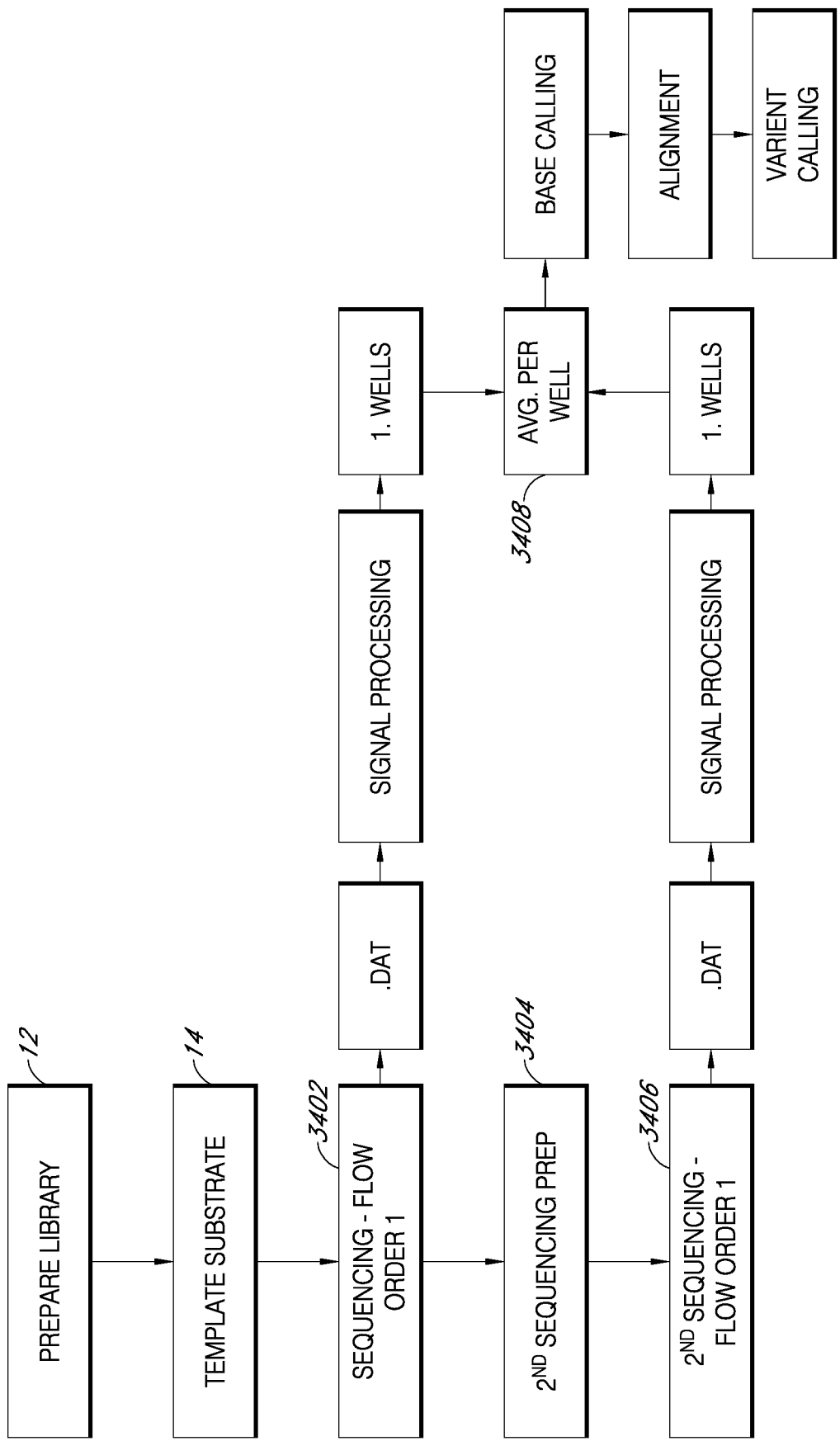
FIG. 34 includes a block diagram of an analysis pipeline for signal data generated by two sequencing steps using the same flow order, in accordance with an embodiment.

FIG. 34 is a block diagram of an analysis pipeline for signal data generated by two sequencing steps using the same flow order, in accordance with an embodiment. The prepare library block 12 and template substrate block 14 are described with respect to FIG. 1. The first sequencing block 3402 is a first application of sequence block 16, described with respect to FIG. 1. After the first sequencing block 3402, the second sequencing preparation block 3404 is applied. The second sequencing preparation block 3404 represents applying the denature block 18 after the substrate is moved to the templating zone from the sequencing zone, the re-prime block 20, the re-enzyme block 22 and moving the substrate to the sequencing zone from the templating zone, as described with respect to FIG. 1. The second sequencing block 3406 is a second application of sequence block 16 described with respect to FIG. 1. The first sequencing block 3402 and the second sequencing block 3406 each generate a raw data file, such as a .DAT file, for the respective sequencing application. The signal processing steps described with respect to FIG. 31 may be applied independently to each raw data file to generate incorporation signal measurement data for files, such as the 1.wells files. The signal processing applied to each of the raw data files may provide first and second sets of signals, each set including a signal measurement per well and per flow. The first and second sets of signals may be stored in respective files, such as respective 1.wells files.

At block 3408, the signal measurement per well and per flow of the first set may be averaged with the signal measurement for the corresponding well and flow of the second set to generate an average signal measurement per well and per flow. In some embodiments, the averaging block 3408 may calculate a weighted average. The weights for the weighted average may apply weights to the signal measurements based on the signal-to-noise ratio (SNR), so that the signal with a higher SNR has a greater weight. In some embodiments, the averaging block 3408 is applied only to those wells where valid library beads are detected for both sequencing blocks 3402 and 3406. For example, if a library bead is detected in a particular well after the first sequencing block 3402, but not after the second sequencing block 3406, only the signal measurements resulting from the first sequencing block 3402 may be retained for base calling.

Base calling may be applied to the average signal measurements to provide the base sequence for a sequence read, as described with respect to FIG. 31. The alignment step may be applied to the sequence reads and the variant calling step may be applied to the aligned sequence reads, as described with respect to FIG. 31.

Figure 35:
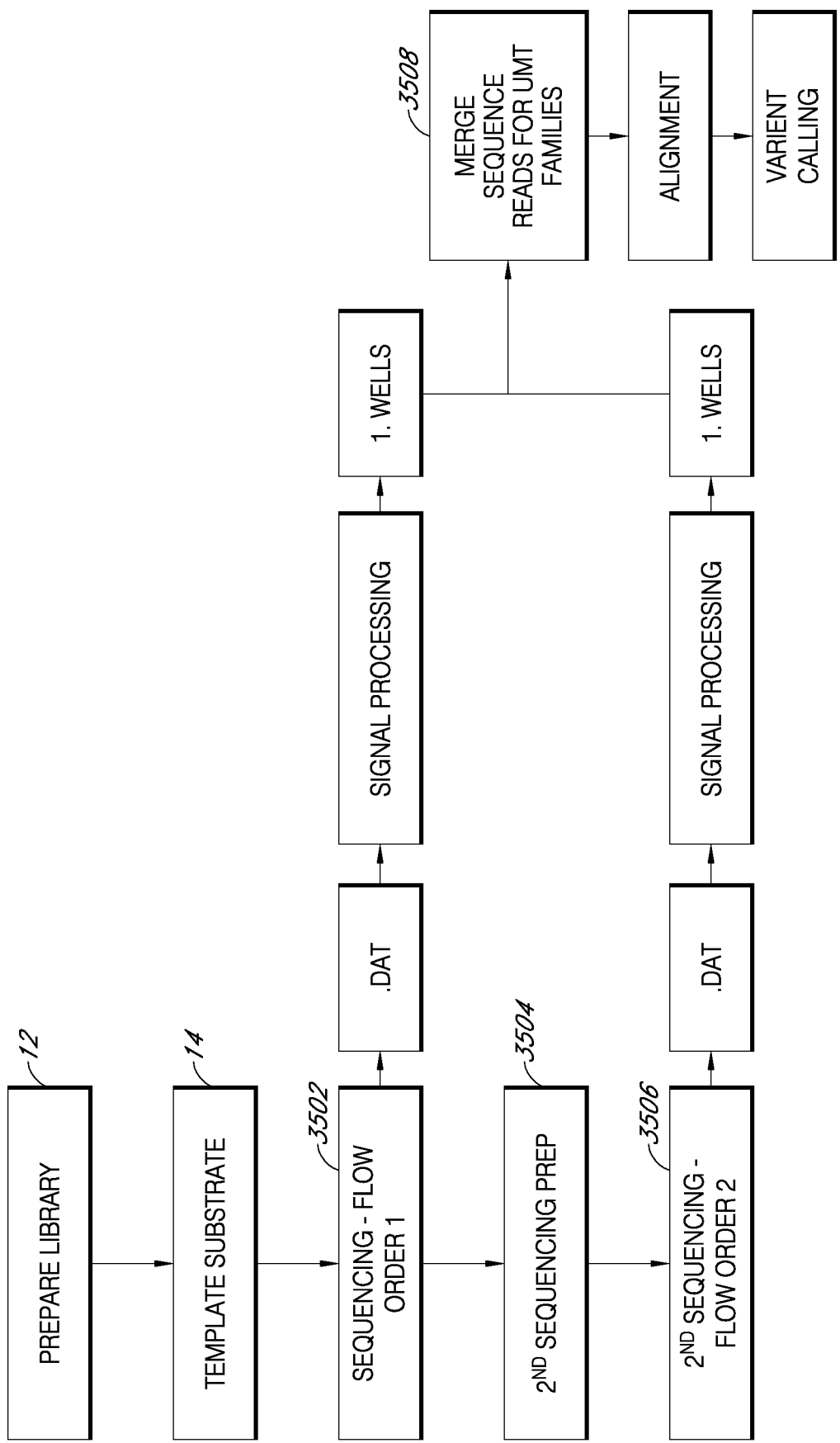
FIG. 35 includes a block diagram of an analysis pipeline for signal data generated by two sequencing steps using different flow orders for sequencing amplicons having molecular tags, in accordance with an embodiment.

FIG. 35 is a block diagram of an analysis pipeline for signal data generated by two sequencing steps using different flow orders for sequencing amplicons having molecular tags, in accordance with an embodiment. Molecular tagging of nucleic acid sequences is useful for identifying the nucleic acid sequence reads that originate from the same polynucleotide molecule and classifying them into a family based on their unique molecular tag (UMT) sequence. Methods for generating molecular tagged nucleic acid sequence data may include one or more features described in U.S. Pat. Appl. Publ. No. 2016/0362748, published Dec. 15, 2016, incorporated by reference herein in its entirety.

The prepare library block 12 and template substrate block 14 are described with respect to FIG. 1. The first sequencing block 3502 is a first application of sequence block 16, described with respect to FIG. 1, using a first flow order. After the first sequencing block 3502, the second sequencing preparation block 3504 is applied. The second sequencing preparation block 3504 represents applying the denature block 18 after the substrate is moved to the templating zone from the sequencing zone, the re-prime block 20, the re-enzyme block 22 and moving the substrate to the sequencing zone from the templating zone, as described with respect to FIG. 1. The second sequencing block 3506 is a second application of sequence block 16, described with respect to FIG. 1, using a second flow order that is different from the first flow order.

The first sequencing block 3502 and the second sequencing block 3506 each generate a raw data file, such as a .DAT file, for the respective sequencing application. The signal processing steps described with respect to FIG. 31 may be applied independently to each raw data file to generate incorporation signal measurement data for files, such as the 1.wells files. The signal processing applied to each of the raw data files may provide first and second sets of signals, each set including a signal measurement per well and per flow. The first and second sets of signals may be stored in respective files, such as respective 1.wells files.

Base calling may be applied to the signal measurements for the first and second sets of signals independently to provide the base sequences for sequence reads, as described with respect to FIG. 31. The base sequences for the sequence reads may be stored in first and second unmapped BAM files. At block 3508, the sequence reads of the first set may be merged with the sequence reads of the second set by grouping reads having the same UMTs. The UMT is used to identify the sequence reads that originate from the same polynucleotide molecule and classify them into a family. A consensus base sequence may be determined for each family of sequence reads. The alignment step may be applied to the consensus base sequences and variant calling step may be applied to the aligned consensus base sequences. Methods for generating the consensus base sequences, alignment and variant detection for molecular tagged nucleic acid sequence data may include one or more features described in U.S. Pat. Appl. Publ. No. 2018/0336316, published Nov. 22, 2018, incorporated by reference herein in its entirety.

EXAMPLES

Example 1

Using the Genexus™ Sequencer, resequencing is performed based on a standard library. A GX5™ chip, Genexus™ coupler, and Genexus™ Templating Strips 3-GX5™ and 4 are used in accordance with standard instructions. A first sequencing run is performed following standard protocols. After the first sequencing run, the chip is automatically returned to the templating station, a melt-off process is performed by raising the temperature of the chip and solutions within the flow cell of the chip, and the template sequences are reprimed. A second sequencing run is performed by automatically moving the chip to the sequencing station and following standard sequencing protocols. The data is averaged as described above.

Resequencing resulted in a 2-base increase in AQ20 RL and a 0.11% increase in raw read accuracy.

Example 2

The procedure of Example 1 is repeated using libraries prepared from Oncomine™ Comprehensive Assay v3 GX, Oncomine™ Precision Assay GX, and CarrierSeg™ Assay adapted for the Genexus Sequencer.

Resequencing provided at least a 9% increase in aligned reads for the library derived from the Oncomine™ Comprehensive Assay v3 GX, at least a 6% increase in aligned reads for the library derived from the Oncomine™ Precision Assay GX, and at least an 11% increase in aligned reads for the library derived from the CarrierSeg™ Assay.

In a first aspect, a method for sequencing a target polynucleotide includes detecting a first series of nucleotide incorporations complementary to at least a portion of the target polynucleotide. The first series of nucleotide incorporations forms a first complementary polynucleotide. The target nucleotide is secured to a substrate disposed in a sequencing zone of an assembly. The method further includes moving the substrate to which the target nucleotide is secured to a templating zone of the assembly; removing the first complementary polynucleotide when the substrate is disposed at the templating zone of the assembly, the target polynucleotide remaining secured to the substrate; following the removing, moving the substrate to which the target polynucleotide is secured to the sequencing zone; and detecting a second series of nucleotide incorporations complementary to at least a portion of the target polynucleotide, the second series of nucleotide incorporations forming a second complementary polynucleotide.

In an example of the first aspect, the second series of nucleotide incorporations is at least 97% the same as the first series of nucleotide incorporations.

In another example of the first aspect and the above examples, the second series of nucleotide incorporations is at least 99% the same as the first series of nucleotide incorporations.

In a further example of the first aspect and the above examples, removing includes denaturing using a change in ionic strength to disassociate the first complementary polynucleotide and the target polynucleotide.

In an additional example of the first aspect and the above examples, removing include melting by increasing a temperature to disassociate the first complementary polynucleotide and the target polynucleotide.

In another example of the first aspect and the above examples, the method further includes adding a primer at least partially complementary to the target polynucleotide following the removing. For example, adding the primer includes adding the primer while the substrate is disposed in the templating zone.

In a further example of the first aspect and the above examples, detecting the first series of nucleotide incorporations is performed using a first flow order of nucleotides and the second series of nucleotide incorporations is performed using a second flow order of nucleotides.

In an additional example of the first aspect and the above examples, the first flow order is different from the second flow order.

In another example of the first aspect and the above examples, the detecting the first series of nucleotide incorporations and the detecting the second series of nucleotide incorporations produces a first and second sets of signals, the method further comprising using the first and second sets of signals to determine a ordered set of base calls. For example, using the first and second sets of signals includes averaging corresponding signals of the first and second sets of signals. In another example, averaging includes weighted averaging.

In further example of the first aspect and the above examples, the substrate includes an array of sensors, the target polynucleotide secured in proximity to a sensor of the array of sensors.

In an additional example of the first aspect and the above examples, the method further includes engaging an adapter to the substrate when the substrate is disposed in the templating zone.

In another example of the first aspect and the above examples, the method further includes engaging a fluidic circuit with the substrate in response to moving the substrate to the sequencing zone.

In a further example of the first aspect and the above examples, the method further includes securing the target polynucleotide to the substrate when the substrate is in the templating zone; and moving the substrate to the sequencing zone prior to detecting the first series of nucleotide incorporations. In a further example, securing the target polynucleotide to the substrate includes forming the target polynucleotide on a polymer particle, depositing a polymer particle into a well of the substrate, and copying the target polynucleotide onto the polymer particle.

In an additional example of the first aspect and the above examples, detecting includes pH-based detection. For example, pH-based detection includes detecting using an ion-sensitive field effect transistor formed in the substrate.

In another example of the first aspect and the above examples, detecting includes fluorescence-based detection.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for sequencing a target polynucleotide, the method comprising:
   detecting a first series of nucleotide incorporations complementary to at least a portion of the target polynucleotide, the first series of nucleotide incorporations forming a first complementary polynucleotide, the target nucleotide secured to a substrate disposed in a sequencing zone of an assembly;
   moving the substrate to which the target nucleotide is secured to a templating zone of the assembly;
   removing the first complementary polynucleotide when the substrate is disposed at the templating zone of the assembly, the target polynucleotide remaining secured to the substrate;
   following the removing, moving the substrate to which the target polynucleotide is secured to the sequencing zone; and
   detecting a second series of nucleotide incorporations complementary to at least a portion of the target polynucleotide, the second series of nucleotide incorporations forming a second complementary polynucleotide.

2. The method of claim 1, wherein the second series of nucleotide incorporations is at least 97% the same as the first series of nucleotide incorporations.

3. The method of claim 1, wherein the second series of nucleotide incorporations is at least 99% the same as the first series of nucleotide incorporations.

4. The method of claim 1, wherein removing includes denaturing using a change in ionic strength to disassociate the first complementary polynucleotide and the target polynucleotide.

5. The method of claim 1, wherein removing includes melting by increasing a temperature to disassociate the first complementary polynucleotide and the target polynucleotide.

6. The method of claim 1, further comprising adding a primer at least partially complementary to the target polynucleotide following the removing.

7. The method of claim 6, wherein adding the primer includes adding the primer while the substrate is disposed in the templating zone.

8. The method of claim 1, wherein detecting the first series of nucleotide incorporations is performed using a first flow order of nucleotides and the second series of nucleotide incorporations is performed using a second flow order of nucleotides.

9. The method of claim 1, wherein the first flow order is different from the second flow order.

10. The method of claim 1, wherein the detecting the first series of nucleotide incorporations and the detecting the second series of nucleotide incorporations produce first and second sets of signals, the method further comprising using the first and second sets of signals to determine a ordered set of base calls.

11. The method of claim 10, wherein using the first and second sets of signals includes averaging corresponding signals of the first and second sets of signals.

12. The method of claim 11, wherein averaging includes weighted averaging.

13. The method of claim 1, wherein the substrate includes an array of sensors, the target polynucleotide secured in proximity to a sensor of the array of sensors.

14. The method of claim 1, further comprising engaging an adapter to the substrate when the substrate is disposed in the templating zone.

15. The method of claim 1, further comprising engaging a fluidic circuit with the substrate in response to moving the substrate to the sequencing zone.

16. The method of claim 1, further comprising:
   securing the target polynucleotide to the substrate when the substrate is in the templating zone; and
   moving the substrate to the sequencing zone prior to detecting the first series of nucleotide incorporations.

17. The method of claim 16, wherein securing the target polynucleotide to the substrate includes:
   forming the target polynucleotide on a polymer particle;
   depositing a polymer particle into a well of the substrate; and
   copying the target polynucleotide onto the polymer particle.

18. The method of claim 1, wherein detecting includes pH-based detection.

19. The method of claim 18, wherein pH-based detection includes detecting using an ion-sensitive field effect transistor formed in the substrate.

20. The method of claim 1, wherein detecting includes fluorescence-based detection.

* * * * *